(12) United States Patent
Sinnott et al.

(10) Patent No.: US 10,499,960 B2
(45) Date of Patent: Dec. 10, 2019

(54) METHOD OF BONE FIXATION

(71) Applicant: IntraFuse, LLC, Logan, UT (US)

(72) Inventors: M. Mary Sinnott, Logan, UT (US); T. Wade Fallin, Hyde Park, UT (US); Mark D. Hayes, Smithfield, UT (US); Robert W. Hoy, Essex Junction, VT (US)

(73) Assignee: IntraFuse, LLC, Logan, UT (US)

( * ) Notice: Subject to any disclaimer, the term of this patent is extended or adjusted under 35 U.S.C. 154(b) by 345 days.

(21) Appl. No.: 15/382,357

(22) Filed: Dec. 16, 2016

(65) Prior Publication Data

US 2017/0112552 A1  Apr. 27, 2017

Related U.S. Application Data

(63) Continuation-in-part of application No. 15/354,634, filed on Nov. 17, 2016, now Pat. No. 10,136,929,
(Continued)

(51) Int. Cl.
*A61B 17/72* (2006.01)
*A61B 17/16* (2006.01)
(Continued)

(52) U.S. Cl.
CPC ...... *A61B 17/7233* (2013.01); *A61B 17/1631* (2013.01); *A61B 17/1717* (2013.01); *A61B 17/1725* (2013.01); *A61B 17/725* (2013.01); *A61B 17/7208* (2013.01); *A61B 17/7225* (2013.01); *A61B 17/7291* (2013.01); *A61B 17/863* (2013.01); *A61B 17/921* (2013.01); *A61B 17/16* (2013.01);
(Continued)

(58) Field of Classification Search
CPC ............ A61B 17/1642; A61B 17/1796; A61B 17/1717; A61B 17/7291; A61B 17/7208; A61B 17/7225; A61B 2017/564
See application file for complete search history.

(56) References Cited

U.S. PATENT DOCUMENTS 2,267,925 A  12/1941  Johnston
3,118,444 A  1/1964  Serrato, Jr.
(Continued)

FOREIGN PATENT DOCUMENTS

WO  WO2006124764 A1  11/2006
WO  WO2008064346 A2  5/2008
(Continued)

OTHER PUBLICATIONS

International Search Report and Written Opinion for International Application No. PCT/US2016/041162 dated Oct. 12, 2016, 18 pp.
(Continued)

*Primary Examiner* — David W Bates
(74) *Attorney, Agent, or Firm* — David Meibos; Maywood IP Law

(57) ABSTRACT

Disclosed are devices and methods for stabilizing first and second bone portions relative to one another. In one example, implants, instruments and methods are provided that can be used with minimal exposure of the fractured bone and along curved path.

18 Claims, 50 Drawing Sheets

Related U.S. Application Data which is a continuation-in-part of application No. 15/285,608, filed on Oct. 5, 2016, now Pat. No. 10,154,863, which is a continuation-in-part of application No. 15/197,879, filed on Jun. 30, 2016, application No. 15/382,357, which is a continuation-in-part of application No. 15/366,445, filed on Dec. 1, 2016.

(60) Provisional application No. 62/268,828, filed on Dec. 17, 2015, provisional application No. 62/191,904, filed on Jul. 13, 2015, provisional application No. 62/238,780, filed on Oct. 8, 2015, provisional application No. 62/266,009, filed on Dec. 11, 2015.

(51) Int. Cl.
  *A61B 17/56* (2006.01)
  *A61B 17/92* (2006.01)
  *A61B 17/17* (2006.01)
  *A61B 17/86* (2006.01)
  *A61B 17/00* (2006.01)

(52) U.S. Cl.
  CPC . *A61B 17/8685* (2013.01); *A61B 2017/00004* (2013.01); *A61B 2017/00946* (2013.01); *A61B 2017/564* (2013.01); *A61B 2017/8655* (2013.01)

(56) References Cited

U.S. PATENT DOCUMENTS

| | | |
|---|---|---|
| 3,456,272 A | 7/1969 | Wendt |
| 3,680,553 A | 8/1972 | Seppo |
| 3,717,146 A | 2/1973 | Halloran |
| 3,760,802 A | 9/1973 | Fischer |
| 3,763,855 A | 10/1973 | McAtee |
| 3,779,239 A | 12/1973 | Fischer |
| 3,805,775 A | 4/1974 | Fischer |
| 4,016,874 A | 4/1977 | Maffei |
| 4,170,990 A | 10/1979 | Baumgart |
| 4,175,555 A | 11/1979 | Herbert |
| 4,212,294 A | 7/1980 | Murphy |
| 4,262,665 A | 4/1981 | Roalstad |
| 4,328,839 A | 5/1982 | Lyons |
| 4,453,539 A | 6/1984 | Raftopoulos |
| 4,457,301 A | 7/1984 | Walker |
| 4,463,753 A | 8/1984 | Gustilo |
| 4,475,545 A | 10/1984 | Ender |
| 4,483,335 A | 11/1984 | Tornier |
| 4,492,226 A | 1/1985 | Belykh |
| 4,590,930 A | 5/1986 | Kurth |
| 4,697,585 A | 10/1987 | Williams |
| 4,706,659 A | 11/1987 | Matthews |
| 4,751,922 A | 6/1988 | DiPietropolo |
| 4,858,602 A | 8/1989 | Seidel |
| 4,947,502 A | 8/1990 | Engelhardt |
| 4,959,064 A | 9/1990 | Engelhardt |
| 5,017,057 A | 5/1991 | Kryger |
| 5,019,079 A | 5/1991 | Ross |
| 5,032,133 A | 7/1991 | Carbone |
| 5,053,035 A | 10/1991 | McLaren |
| 5,061,137 A | 10/1991 | Gourd |
| 5,116,336 A | 5/1992 | Frigg |
| 5,116,378 A | 5/1992 | Carbone |
| 5,259,398 A | 11/1993 | Vrespa |
| 5,281,225 A | 1/1994 | Vicenzi |
| 5,312,255 A | 5/1994 | Bauer |
| 5,334,184 A | 8/1994 | Bimman |
| 5,356,127 A | 10/1994 | Moore |
| 5,374,235 A | 12/1994 | Ahrens |
| 5,397,328 A | 3/1995 | Behrens |
| 5,409,490 A | 4/1995 | Ethridge |
| 5,415,660 A | 5/1995 | Campbell |
| 5,437,674 A | 8/1995 | Worcel |
| 5,480,400 A | 1/1996 | Berger |
| 5,527,316 A | 6/1996 | Stone |
| 5,575,790 A | 11/1996 | Chen |
| 5,603,715 A | 2/1997 | Kessler |
| 5,681,289 A | 10/1997 | Wilcox |
| 5,709,687 A | 1/1998 | Pennig |
| 5,827,289 A | 10/1998 | Reiley |
| 5,871,486 A | 2/1999 | Huebner |
| 5,891,101 A | 4/1999 | Wilcox |
| 5,895,375 A | 4/1999 | Wilcox |
| 5,972,015 A | 10/1999 | Scribner |
| 5,993,450 A | 11/1999 | Worcel |
| 6,030,162 A | 2/2000 | Huebner |
| 6,053,922 A | 4/2000 | Krause |
| 6,162,234 A | 12/2000 | Freedland |
| 6,197,031 B1 | 3/2001 | Barrette |
| 6,224,600 B1 | 5/2001 | Protogirou |
| 6,248,110 B1 | 6/2001 | Reiley |
| 6,280,456 B1 | 8/2001 | Scribner |
| 6,299,615 B1 | 10/2001 | Huebner |
| 6,319,255 B1 | 11/2001 | Grundei |
| 6,322,562 B1 | 11/2001 | Wolter |
| 6,338,732 B1 * | 1/2002 | Yang ............... A61B 17/7216 606/311 |
| 6,368,326 B1 | 4/2002 | Dakin |
| 6,416,517 B2 | 7/2002 | Harder |
| 6,447,514 B1 * | 9/2002 | Stalcup ............ A61B 17/164 606/63 |
| 6,447,515 B1 | 9/2002 | Meldrum |
| 6,447,518 B1 | 9/2002 | Krause |
| 6,517,541 B1 | 2/2003 | Sesic |
| 6,524,313 B1 | 2/2003 | Fassier |
| 6,551,321 B1 | 4/2003 | Burkinshaw |
| 6,554,833 B2 | 4/2003 | Levy |
| 6,605,090 B1 | 8/2003 | Trieu |
| 6,613,052 B1 | 9/2003 | Kinnett |
| 6,623,505 B2 | 9/2003 | Scribner |
| 6,632,235 B2 | 10/2003 | Weikel |
| 6,656,184 B1 | 12/2003 | White |
| 6,736,819 B2 | 5/2004 | Tipirneni |
| 6,749,611 B2 | 6/2004 | Venturini |
| 6,790,210 B1 * | 9/2004 | Cragg ............... A61B 17/1617 606/180 |
| 6,852,115 B2 | 2/2005 | Kinnett |
| 6,875,215 B2 | 4/2005 | Taras |
| 6,899,719 B2 | 5/2005 | Reiley |
| 6,949,100 B1 | 9/2005 | Venturini |
| 6,949,101 B2 | 9/2005 | McCleary |
| 6,955,513 B2 | 10/2005 | Niku |
| 7,041,106 B1 | 5/2006 | Carver |
| 7,044,954 B2 | 5/2006 | Reiley |
| 7,156,861 B2 | 1/2007 | Scribner |
| 7,175,626 B2 | 2/2007 | Neff |
| 7,249,923 B2 | 7/2007 | Niku |
| 7,255,712 B1 | 8/2007 | Steinberg |
| 7,527,611 B2 | 5/2009 | Sweeney |
| 7,527,627 B2 | 5/2009 | Ferrante |
| 7,534,244 B2 | 5/2009 | Ferrante |
| 7,534,245 B2 | 5/2009 | Chappuis |
| 7,588,577 B2 | 9/2009 | Fencl |
| 7,591,823 B2 | 9/2009 | Tipirneni |
| 7,621,912 B2 | 11/2009 | Harms |
| 7,625,395 B2 | 12/2009 | Mückter |
| 7,632,277 B2 | 12/2009 | Woll |
| 7,666,205 B2 | 2/2010 | Weikel |
| 7,682,364 B2 | 3/2010 | Reiley |
| 7,722,611 B2 * | 5/2010 | Cavallazzi ......... A61B 17/1739 606/60 |
| 7,727,263 B2 | 6/2010 | Cragg |
| 7,744,599 B2 | 6/2010 | Cragg |
| 7,766,968 B2 | 8/2010 | Sweeney |
| 7,780,667 B2 | 8/2010 | Watanabe |
| 7,799,053 B2 | 9/2010 | Haid, Jr. |
| 7,819,874 B2 | 10/2010 | Woll |
| 7,842,095 B2 | 11/2010 | Klein |
| 7,846,162 B2 | 12/2010 | Nelson |
| 7,883,509 B2 | 2/2011 | Ferrante |
| 7,901,412 B2 | 3/2011 | Tipirneni |

(56) References Cited

U.S. PATENT DOCUMENTS

| | | |
|---|---|---|
| 7,909,825 B2 | 3/2011 | Saravia |
| 7,914,533 B2 | 3/2011 | Nelson |
| 7,918,853 B2 | 4/2011 | Watanabe |
| 7,931,652 B2 | 4/2011 | Ferrante |
| 7,942,875 B2 | 5/2011 | Nelson |
| 8,007,498 B2 | 8/2011 | Mische |
| 8,012,155 B2 | 9/2011 | Prygoski |
| 8,034,071 B2 | 10/2011 | Scribner |
| 8,062,270 B2 | 11/2011 | Sweeney |
| 8,066,748 B2 | 11/2011 | Lieberman |
| 8,083,742 B2 | 12/2011 | Martin |
| 8,105,326 B2 | 1/2012 | Ferrante |
| 8,109,936 B2 | 2/2012 | Tipirneni |
| 8,128,626 B2 | 3/2012 | Justin |
| 8,128,627 B2 | 3/2012 | Justin |
| 8,147,492 B2 | 4/2012 | Justin |
| 8,162,943 B2 | 4/2012 | Justin |
| 8,167,881 B2 | 5/2012 | Justin |
| 8,187,275 B2 | 5/2012 | Ferrante |
| 8,197,523 B2 | 6/2012 | Bottlang |
| 8,206,389 B2 | 6/2012 | Huebner |
| 8,221,419 B2 | 7/2012 | Frigg |
| 8,246,691 B2 | 8/2012 | Mangiardi |
| 8,287,538 B2 | 10/2012 | Brenzel |
| 8,287,539 B2 | 10/2012 | Nelson |
| 8,287,541 B2 | 10/2012 | Nelson |
| 8,298,234 B2 | 10/2012 | Ferrante |
| 8,303,589 B2 | 11/2012 | Tyber |
| 8,313,488 B2 | 11/2012 | Schlienger |
| 8,317,789 B2 | 11/2012 | LeCronier |
| 8,317,846 B2 | 11/2012 | Bottlang |
| 8,328,806 B2 | 12/2012 | Tyber |
| 8,343,197 B2 | 1/2013 | Gonzalez-Hernandez |
| 8,343,199 B2 | 1/2013 | Tyber |
| 8,382,760 B2 | 2/2013 | Mantovani |
| 8,388,620 B2 | 3/2013 | Brunnarius |
| 8,398,690 B2 | 3/2013 | Bottlang |
| 8,403,938 B2 | 3/2013 | Aeschlimann |
| 8,430,879 B2 | 4/2013 | Stoneburner |
| 8,435,238 B2 | 5/2013 | Dejardin |
| 8,435,272 B2 | 5/2013 | Dougherty |
| 8,439,916 B2 | 5/2013 | Coati |
| 8,439,917 B2 | 5/2013 | Saravia |
| 8,449,574 B2 | 5/2013 | Biedermann |
| 8,460,293 B2 | 6/2013 | Coati |
| 8,496,657 B2 | 7/2013 | Bonutti |
| 8,496,658 B2 | 7/2013 | Stoneburner |
| 8,496,712 B2 | 7/2013 | Reiley |
| 8,507,614 B2 | 8/2013 | Shalaby |
| 8,529,611 B2 | 9/2013 | Champagne |
| 8,545,499 B2 | 10/2013 | Lozier |
| 8,568,413 B2 | 10/2013 | Mazur |
| 8,597,337 B2 | 12/2013 | Champagne |
| 8,608,743 B2 | 12/2013 | Baumgartner |
| 8,617,161 B2 | 12/2013 | Ferrante |
| 8,617,585 B2 | 12/2013 | Boden |
| 8,622,739 B2 | 1/2014 | Karmon |
| 8,632,543 B2 | 1/2014 | Metzinger |
| 8,632,570 B2 | 1/2014 | Biedermann |
| 8,652,141 B2 | 2/2014 | Rush |
| 8,663,224 B2 | 3/2014 | Overes |
| 8,663,326 B2 | 3/2014 | Osman |
| 8,679,120 B2 | 3/2014 | Frigg |
| 8,679,167 B2 | 3/2014 | Tipirneni |
| 8,696,719 B2 | 4/2014 | Lofthouse |
| 8,702,768 B2 | 4/2014 | Tipirneni |
| 8,709,055 B2 | 4/2014 | Beyar |
| 8,721,690 B2 | 5/2014 | Harms |
| 8,734,497 B2 | 5/2014 | Goel |
| 8,740,955 B2 | 6/2014 | Bottlang |
| 8,784,491 B2 | 7/2014 | Biedermann |
| 8,801,722 B2 | 8/2014 | Aeschlimann |
| 8,808,337 B2 | 8/2014 | Sweeney |
| 8,808,338 B2 * | 8/2014 | Martin ............... A61B 17/1717 606/316 |
| 8,821,494 B2 | 9/2014 | Pilgeram |
| 8,828,067 B2 | 9/2014 | Tipirneni |
| 8,834,468 B2 | 9/2014 | Justin |
| 8,840,612 B2 | 9/2014 | Tontz |
| 8,870,836 B2 | 10/2014 | Sweeney |
| 8,888,815 B2 | 11/2014 | Holmes, Jr. |
| 8,900,233 B2 | 12/2014 | Logan |
| 8,939,978 B2 | 1/2015 | Watanabe |
| 8,961,516 B2 | 2/2015 | Nelson |
| 8,979,930 B2 | 3/2015 | Glazer |
| 8,992,615 B2 | 3/2015 | Pitkin |
| 8,998,999 B2 | 4/2015 | Lewis |
| 9,033,984 B2 | 5/2015 | Overes |
| 9,060,820 B2 * | 6/2015 | Nelson ............... A61B 17/7208 |
| 9,072,510 B2 | 7/2015 | Thornes |
| 9,314,286 B2 | 4/2016 | Bottlang |
| 9,421,045 B2 | 8/2016 | Justin |
| 9,498,264 B2 | 11/2016 | Harshman et al. |
| 9,522,019 B2 | 12/2016 | Biedermann |
| 2002/0143335 A1 | 10/2002 | von Hoffman |
| 2002/0198527 A1 | 12/2002 | Muckter |
| 2003/0187447 A1 | 10/2003 | Ferrante |
| 2003/0220641 A1 * | 11/2003 | Thelen ............... A61B 17/1668 606/60 |
| 2003/0229372 A1 | 12/2003 | Reiley |
| 2004/0049192 A1 | 3/2004 | Shimizu |
| 2004/0122455 A1 | 6/2004 | Lin |
| 2004/0127898 A1 | 7/2004 | Adam |
| 2004/0167519 A1 | 8/2004 | Weiner |
| 2005/0055024 A1 | 3/2005 | James |
| 2005/0119662 A1 | 6/2005 | Reiley |
| 2005/0131267 A1 | 6/2005 | Talmadge |
| 2005/0131268 A1 | 6/2005 | Talmadge |
| 2005/0165402 A1 | 7/2005 | Taras |
| 2005/0165405 A1 | 7/2005 | Tsou |
| 2005/0182402 A1 | 8/2005 | Hansson |
| 2005/0209629 A1 | 9/2005 | Kerr |
| 2006/0149265 A1 | 7/2006 | James |
| 2006/0149268 A1 * | 7/2006 | Truckai ............... A61B 17/1615 606/79 |
| 2006/0155281 A1 | 7/2006 | Kaup |
| 2006/0173291 A1 | 8/2006 | Glossop |
| 2006/0235460 A1 | 10/2006 | Reiley |
| 2006/0271061 A1 | 11/2006 | Beyar |
| 2006/0293667 A1 | 12/2006 | Vignery |
| 2007/0005146 A1 | 1/2007 | Heyligers |
| 2007/0016190 A1 | 1/2007 | Martinez |
| 2007/0016204 A1 | 1/2007 | Martinez |
| 2007/0060941 A1 | 3/2007 | Reiley |
| 2007/0083207 A1 | 4/2007 | Ziolo |
| 2007/0276382 A1 | 11/2007 | Mikhail |
| 2008/0004626 A1 | 1/2008 | Glazer |
| 2008/0039941 A1 | 2/2008 | Steinberg |
| 2008/0051825 A1 | 2/2008 | Reiley |
| 2008/0058823 A1 | 3/2008 | Reiley |
| 2008/0058824 A1 | 3/2008 | Reiley |
| 2008/0058828 A1 | 3/2008 | Reiley |
| 2008/0109008 A1 | 5/2008 | Schwager |
| 2008/0125805 A1 | 5/2008 | Mische |
| 2008/0132896 A1 * | 6/2008 | Bowen ............... A61B 17/1604 606/80 |
| 2008/0140078 A1 | 6/2008 | Nelson |
| 2008/0149115 A1 | 6/2008 | Hauck |
| 2008/0188895 A1 | 8/2008 | Cragg |
| 2008/0221620 A1 | 9/2008 | Krause |
| 2008/0234752 A1 | 9/2008 | Dahners |
| 2008/0249574 A1 | 10/2008 | McCombs |
| 2008/0249580 A1 | 10/2008 | Evans |
| 2008/0255555 A1 | 10/2008 | Justis |
| 2008/0269759 A1 | 10/2008 | Reiley |
| 2008/0269795 A1 | 10/2008 | Reiley |
| 2008/0269796 A1 | 10/2008 | Reiley |
| 2009/0005782 A1 | 1/2009 | Chirico |
| 2009/0005821 A1 | 1/2009 | Chirico |
| 2009/0012564 A1 | 1/2009 | Chirico |
| 2009/0018542 A1 | 1/2009 | Saravia |
| 2009/0062868 A1 | 3/2009 | Casutt |
| 2009/0062928 A1 | 3/2009 | Pitkin |
| 2009/0076517 A1 | 3/2009 | Reiley |

(56) References Cited

U.S. PATENT DOCUMENTS

| | | |
|---|---|---|
| 2009/0131991 A1 | 5/2009 | Tipirneni |
| 2009/0143781 A1 | 6/2009 | Mische |
| 2009/0149890 A1 | 6/2009 | Martin |
| 2009/0157078 A1 | 6/2009 | Mikol |
| 2009/0264937 A1 | 10/2009 | Parrott |
| 2010/0016905 A1 | 1/2010 | Greenhalgh |
| 2010/0023057 A1 | 1/2010 | Aeschlimann |
| 2010/0069970 A1 | 3/2010 | Lewis |
| 2010/0076503 A1 | 3/2010 | Beyar |
| 2010/0082036 A1 | 4/2010 | Reiley |
| 2010/0114097 A1 | 5/2010 | Siravo |
| 2010/0114181 A1 | 5/2010 | Lob |
| 2010/0121326 A1 | 5/2010 | Woll |
| 2010/0137862 A1 | 6/2010 | Diao |
| 2010/0145396 A1 | 6/2010 | Thornes |
| 2010/0168755 A1 | 7/2010 | Reiley |
| 2010/0179551 A1 | 7/2010 | Keller |
| 2010/0211076 A1 | 8/2010 | Germain |
| 2010/0228301 A1 | 9/2010 | Greenhalgh |
| 2010/0256731 A1 | 10/2010 | Mangiardi |
| 2010/0274246 A1 | 10/2010 | Beyar |
| 2010/0286692 A1 | 11/2010 | Greenhalgh |
| 2010/0292695 A1 | 11/2010 | May |
| 2010/0312292 A1 | 12/2010 | Tipirneni |
| 2010/0318087 A1 | 12/2010 | Scribner |
| 2011/0009865 A1 | 1/2011 | Orfaly |
| 2011/0009907 A1 | 1/2011 | Klein |
| 2011/0118740 A1 | 5/2011 | Rabiner |
| 2011/0144703 A1 | 6/2011 | Krause |
| 2011/0160728 A1 | 6/2011 | Blitz |
| 2011/0172667 A1 | 7/2011 | Richards |
| 2011/0178520 A1 | 7/2011 | Taylor |
| 2011/0184472 A1 | 7/2011 | Niederberger |
| 2011/0196371 A1 | 8/2011 | Forsell |
| 2011/0196435 A1 | 8/2011 | Forsell |
| 2011/0218585 A1 | 9/2011 | Krinke |
| 2011/0282346 A1 | 11/2011 | Pham |
| 2011/0282398 A1 | 11/2011 | Overes |
| 2011/0295255 A1 | 12/2011 | Roberts |
| 2011/0306975 A1 | 12/2011 | Kaikkonen |
| 2012/0029432 A1 | 2/2012 | Sweeney |
| 2012/0029579 A1 | 2/2012 | Bottlang |
| 2012/0065638 A1 | 3/2012 | Moore |
| 2012/0065692 A1 | 3/2012 | Champagne |
| 2012/0123481 A1 | 5/2012 | Lin |
| 2012/0172936 A1 | 7/2012 | Horrell |
| 2012/0203346 A1 | 8/2012 | Kraus |
| 2012/0209267 A1 | 8/2012 | Lee |
| 2012/0221009 A1 | 8/2012 | Tada |
| 2012/0226362 A1 | 9/2012 | Mische |
| 2012/0232533 A1 | 9/2012 | Veldman |
| 2012/0232597 A1 | 9/2012 | Saidha |
| 2012/0239037 A1 | 9/2012 | Justin |
| 2012/0239038 A1 | 9/2012 | Saravia |
| 2012/0289961 A1 | 11/2012 | Frigg |
| 2013/0035689 A1 | 2/2013 | Nanavati |
| 2013/0041412 A1 | 2/2013 | Moumene |
| 2013/0079829 A1 | 3/2013 | Globerman |
| 2013/0123857 A1 | 5/2013 | Biedermann |
| 2013/0131678 A1 | 5/2013 | Dahners |
| 2013/0184765 A1 | 7/2013 | Beyar |
| 2013/0190762 A1 | 7/2013 | Frankle |
| 2013/0190871 A1* | 7/2013 | Markarian ......... A61B 17/0401 623/13.13 |
| 2013/0218214 A1 | 8/2013 | Beyar |
| 2013/0226180 A1 | 8/2013 | Lee |
| 2013/0231665 A1 | 9/2013 | Saravia |
| 2013/0231666 A1 | 9/2013 | Lee |
| 2013/0237813 A1 | 9/2013 | Beyar |
| 2013/0267953 A1 | 10/2013 | Brenzel |
| 2013/0296863 A1 | 11/2013 | Globerman |
| 2013/0296952 A1 | 11/2013 | Globerman |
| 2013/0297035 A1 | 11/2013 | Reiley |
| 2013/0317556 A1 | 11/2013 | Goldzak |
| 2013/0325007 A1 | 12/2013 | Beyar |
| 2013/0325077 A1 | 12/2013 | Champagne |
| 2013/0340240 A1 | 12/2013 | Irawan |
| 2014/0031823 A1 | 1/2014 | Mazur |
| 2014/0039495 A1 | 2/2014 | Bonutti |
| 2014/0058390 A1 | 2/2014 | Taylor |
| 2014/0058391 A1 | 2/2014 | Appenzeller |
| 2014/0058432 A1 | 2/2014 | Scribner |
| 2014/0074252 A1 | 3/2014 | Baumgartner |
| 2014/0106306 A1 | 4/2014 | Karmon |
| 2014/0114312 A1 | 4/2014 | Krause |
| 2014/0128870 A1 | 5/2014 | Brenzel |
| 2014/0131909 A1 | 5/2014 | Osman |
| 2014/0163557 A1 | 6/2014 | Beyar |
| 2014/0163624 A1 | 6/2014 | Siegal |
| 2014/0180428 A1 | 6/2014 | McCormick |
| 2014/0188113 A1 | 7/2014 | Overes |
| 2014/0194877 A1 | 7/2014 | Mangiardi |
| 2014/0207138 A1 | 7/2014 | Justin |
| 2014/0222001 A1 | 8/2014 | Beyar |
| 2014/0222080 A1 | 8/2014 | Biedermann |
| 2014/0222091 A1 | 8/2014 | Champagne |
| 2014/0249529 A1 | 9/2014 | LeCronier |
| 2014/0288651 A1 | 9/2014 | Biedermann |
| 2014/0316469 A1 | 10/2014 | Harms |
| 2014/0336653 A1 | 11/2014 | Bromer |
| 2014/0336663 A1 | 11/2014 | Mayer |
| 2014/0358146 A1 | 12/2014 | Meek |
| 2014/0371747 A1 | 12/2014 | Martin |
| 2015/0005827 A1 | 1/2015 | Lin |
| 2015/0012048 A1 | 1/2015 | Huebner |
| 2015/0039033 A1 | 2/2015 | Biedermann |
| 2015/0045791 A1 | 2/2015 | Mangiardi |
| 2015/0045792 A1 | 2/2015 | Mangiardi |
| 2015/0066097 A1 | 3/2015 | Biedermann |
| 2015/0105830 A1 | 4/2015 | Biedermann |
| 2015/0133937 A1 | 5/2015 | Benedict |
| 2015/0250503 A1 | 9/2015 | Tipirneni |
| 2015/0374411 A1 | 12/2015 | Ehmke |
| 2016/0128742 A9 | 5/2016 | Justin |
| 2016/0317201 A1 | 11/2016 | Justin |

FOREIGN PATENT DOCUMENTS

| | | |
|---|---|---|
| WO | WO2008064347 A2 | 5/2008 |
| WO | WO2008064350 A2 | 5/2008 |
| WO | WO2009009772 A1 | 1/2009 |
| WO | WO2009076086 A1 | 6/2009 |
| WO | WO2009152270 A1 | 12/2009 |
| WO | WO2009152272 A1 | 12/2009 |
| WO | WO2009152273 A1 | 12/2009 |
| WO | WO2010037038 A2 | 4/2010 |
| WO | WO2010062379 A1 | 6/2010 |
| WO | WO2010099239 A3 | 1/2011 |
| WO | WO2011116078 A1 | 9/2011 |
| WO | WO2011154891 A2 | 12/2011 |
| WO | WO2012051137 A1 | 4/2012 |
| WO | WO2012069727 A1 | 5/2012 |
| WO | WO2012089330 A1 | 7/2012 |
| WO | WO2012089331 A1 | 7/2012 |
| WO | WO2012091681 A3 | 8/2012 |
| WO | WO2012107913 A2 | 8/2012 |
| WO | WO2012156915 A2 | 11/2012 |
| WO | WO2013063145 A1 | 5/2013 |
| WO | WO2013074884 A1 | 5/2013 |
| WO | WO2013166328 A1 | 11/2013 |
| WO | WO2014031947 A1 | 2/2014 |
| WO | WO2014031951 A1 | 2/2014 |
| WO | WO2014060576 A1 | 4/2014 |
| WO | WO2014060578 A1 | 4/2014 |
| WO | WO2014151907 A2 | 9/2014 |
| WO | WO2015029042 A1 | 3/2015 |

OTHER PUBLICATIONS

EPIFISA Centromedullary Nail, FH Orthopedics, www.f-h-fr, May 2005, 2 pp.

Dual-Trak Clavicle Screw Surgical Technique, Acumed, www.acumed.net, Sep. 2014, 12 pp.

(56) References Cited

OTHER PUBLICATIONS

Fibual Rod System Surgical Technique, Acumed, www.acumed.net, Apr. 2014, 8 pp.
Polarus Plus Humeral Rod, Acumed, www.acumed.net, Nov. 2008, 12 pp.
Asloum, Y., et al., "Internal Fixation of the Fibula in Ankle Fractures. A Prospective, Randomized and Comparative Study: Plating Versus Nailing", Orthopaedics & Traumatology: Surgery & Research 100(2014) S255-S259.
Rockwood Clavicle Pin, Design Rationale and Surgical Technique, Biomet Orthopedics, www.biomet.com, Aug. 31, 2012, 24 pp.
Distal Radius 3D Fracture Management System Surgical Technique, Conventus Orthopaedics, www.conventusortho.com, 12 pp.
Clavicle Fracture Repair Device, Sonoma Orthopedic Products, Inc., www.sonomaorthopedics.com, 2011, 6 pp.
The Nancy Nail Surgical Technique, DePuy Products, www.jnjgateway.com, 1999, 6 pp.
Hand Innovations Minimally Invasive Dorsal Endoplate Surgical Technique, Hand Innovations, www.handinnovations.com, 14 pp.
Latif, Girgis, et al., "The Effect of Percutaneous Screw Fixation of Lateral Malleolus on Ankle Fracture Healing and Function", Surgical Science, 2013, 4, 365-370, 2013.
Ankle Fracture System Abbreviated Surgical Technique, Sonoma Orthopedic Products, Inc., www.sonomaorthopedics.com, 2015, 20 pp.
Fracture and Fixation Products, ConMed Linvatec,, 7 pp.
Flexible Radial Nail Enclouage Radial Souple, www.evolutisfrance.com, 4 pp.
Olecranon Threaded Compression Rod: O'Rod, Acumed, www.acumed.net, Jul. 2010, 8 pp.
Piccolo Composite Made of Carbon Fibers Reinforced Polymer, CarboFix Orthopedics, Ltd., www.carbo-fix.com, Sep. 2011, 4 pp.
Darden Business Publishing—University of Virginia, UVA-QA-0811, Oct. 20, 2014, 10 pp.
IP-XS Nail Compression Nail System Surgical Technique and Product Information, Smith & Nephew GmBH, www.smith-nephew.de, Apr. 2004, 24 pp.
Trigen Intertan Intertrochanteric Antegrade Nail Surgical Technique, Smith & Nehew, Inc., www.smith-newphew.com, 2012, 46 pp.
S.S.T. Small Bone Locking Nail Fibula Nail Surgical Technique, Biomet, Inc., www.bioment.com, 12 pp.
MetaFLEX Percutaneous Flexible IM Nail System for Metacarpal and Metatarsal Fractures, Small Bone Innovtions, www.totalsmallbone.com, Apr. 2007, 2 pp.
Improved Healing of Clavicle Fractures using an Implantable Pre-Curved Intramedullary Rod, Upstate Medical University, www.upstate.edu, 1 pp.
The Titanium Flexible Humeral Nail System, Synthes (USA), Jul. 1999, 4 pp.
The Next Generation in Foot & Ankle Repair and Reconstruction Technology, Arthrex, www.arthrex.com, 2016, 76 pp.
Trim-It Drill Pin Fixation, , 1 pp.
Micronail II Intramedullary Distal Radius System Surgical Technique, Wright Medical Technology, Inc., www.wmt.com, Jun. 15, 2014, 20 pp.
Wrist Fracture Nail, Sonoma Orthopedic Products, Inc. www.sonomaorthopedics.com, 2013, 15 pp.

\* cited by examiner

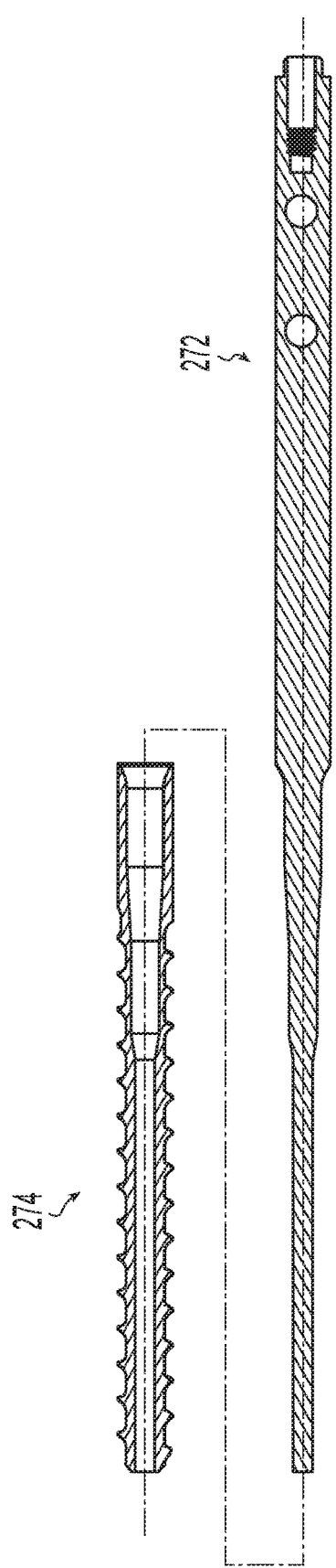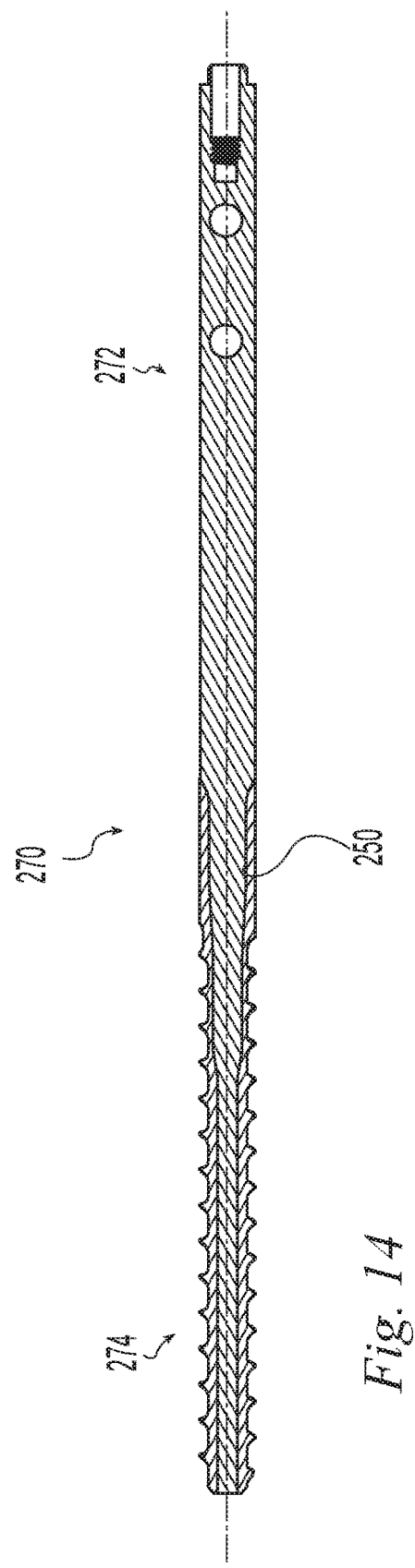
Fig. 14
Fig. 15

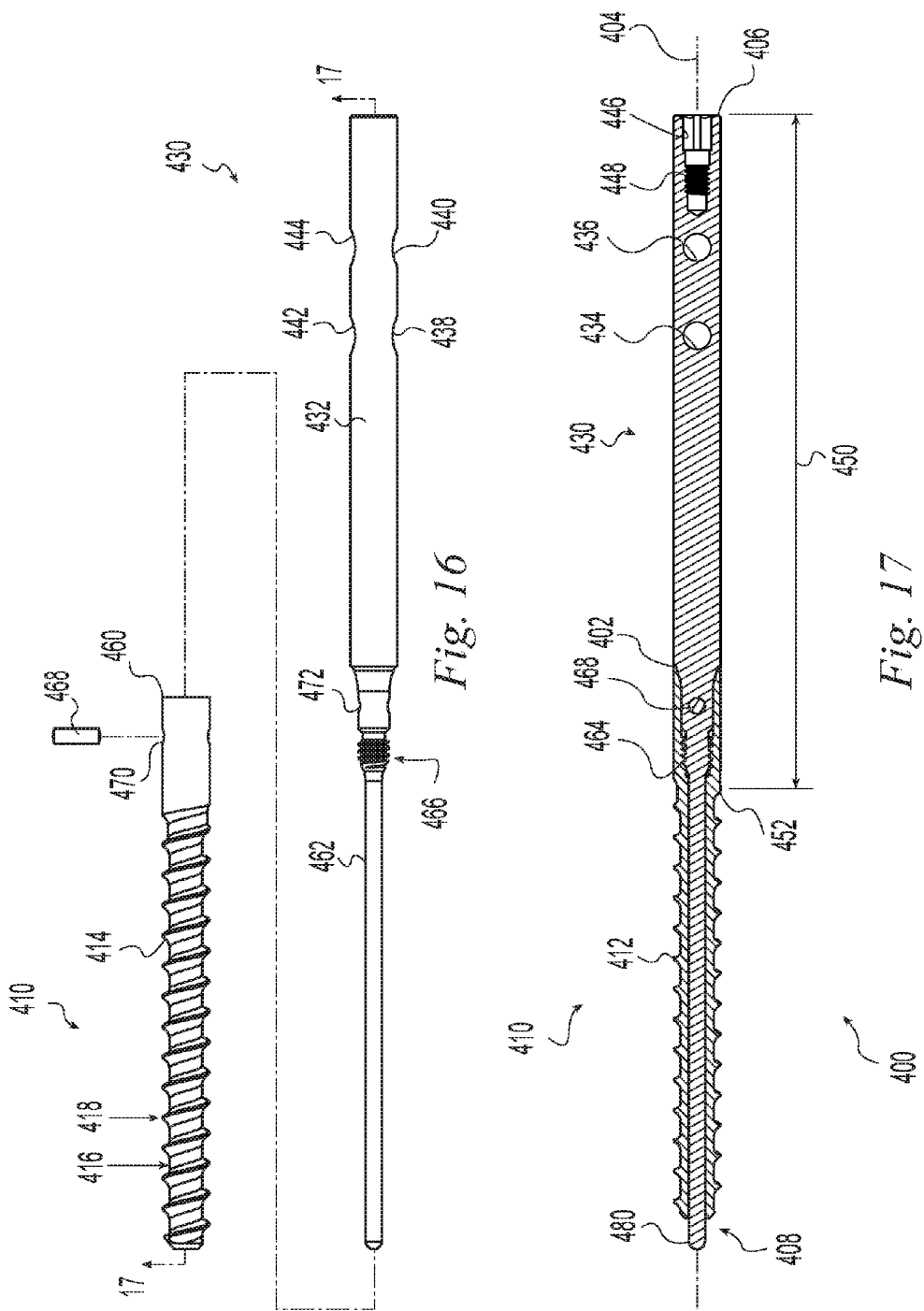

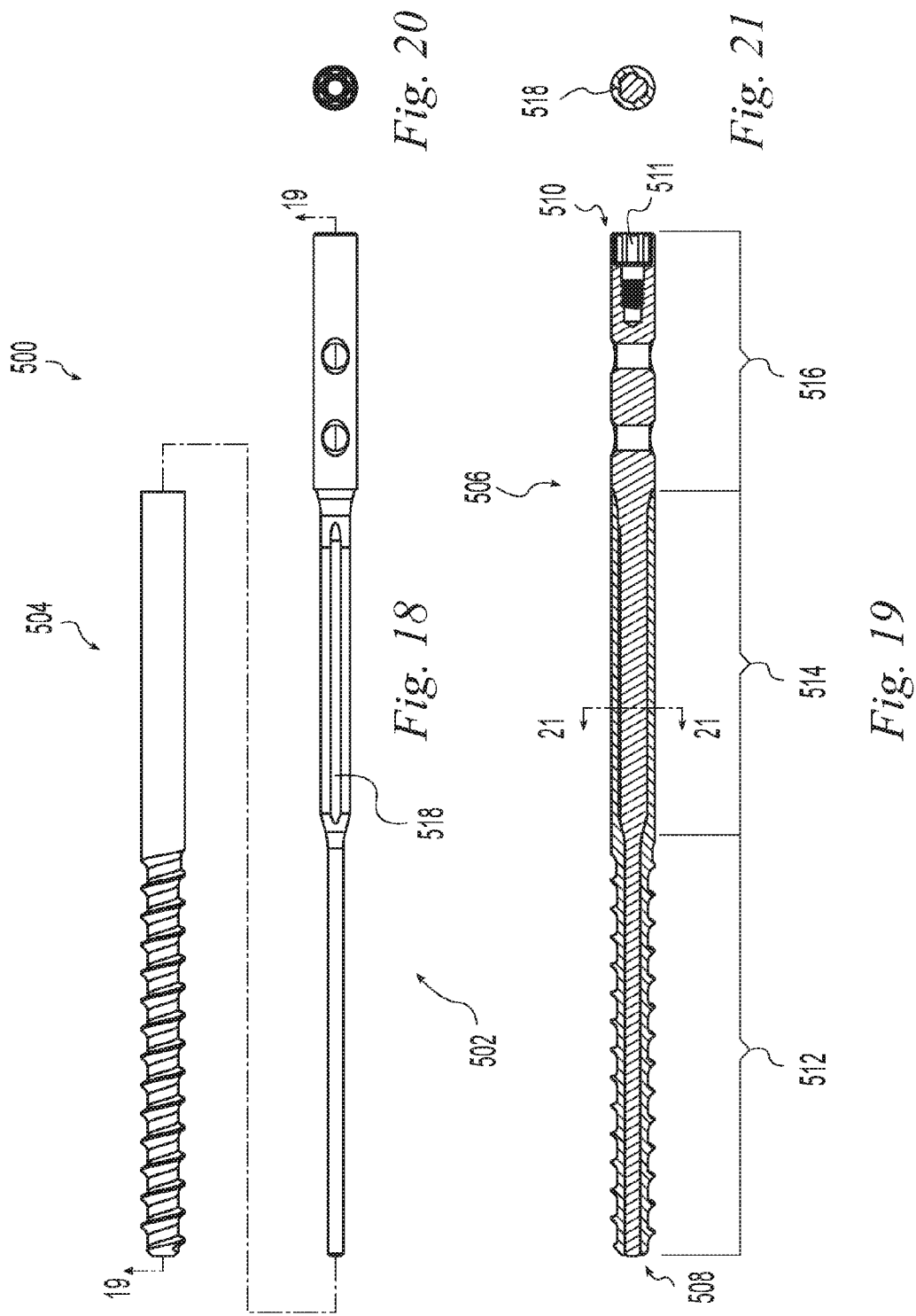

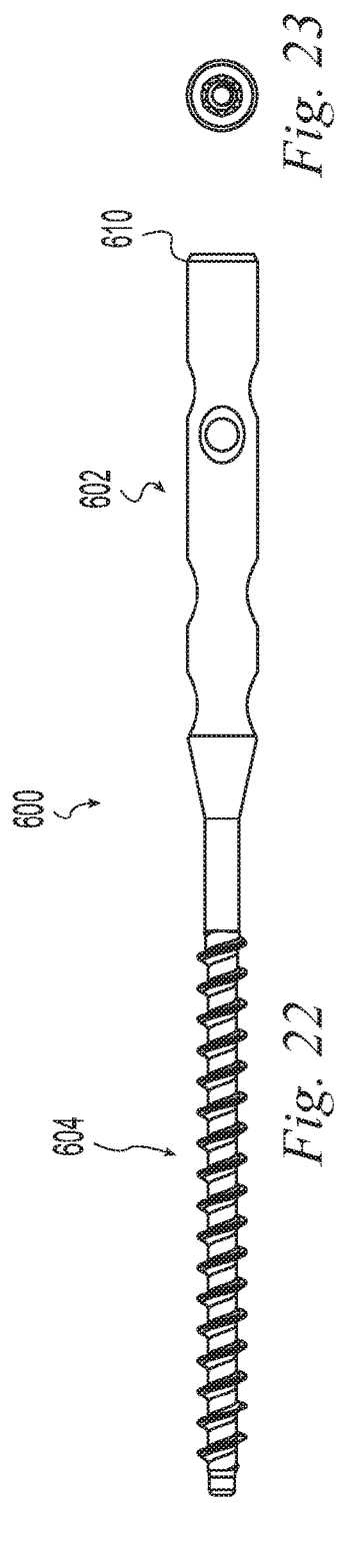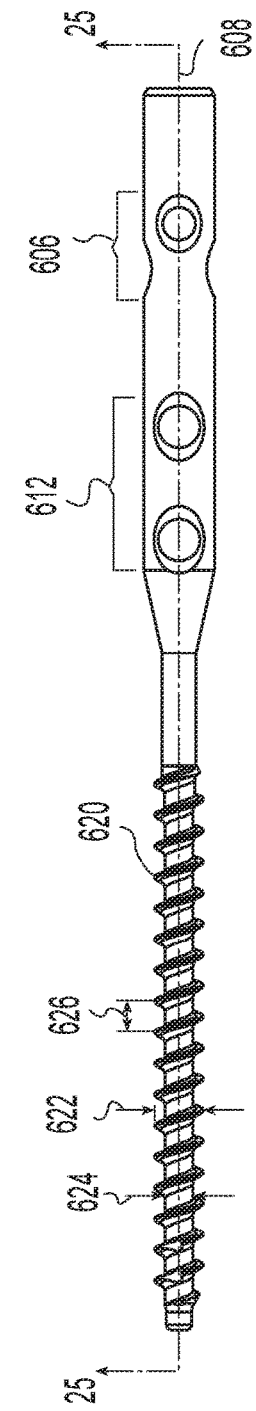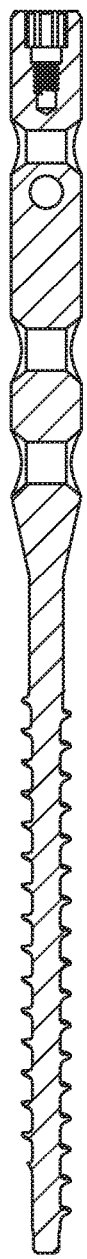

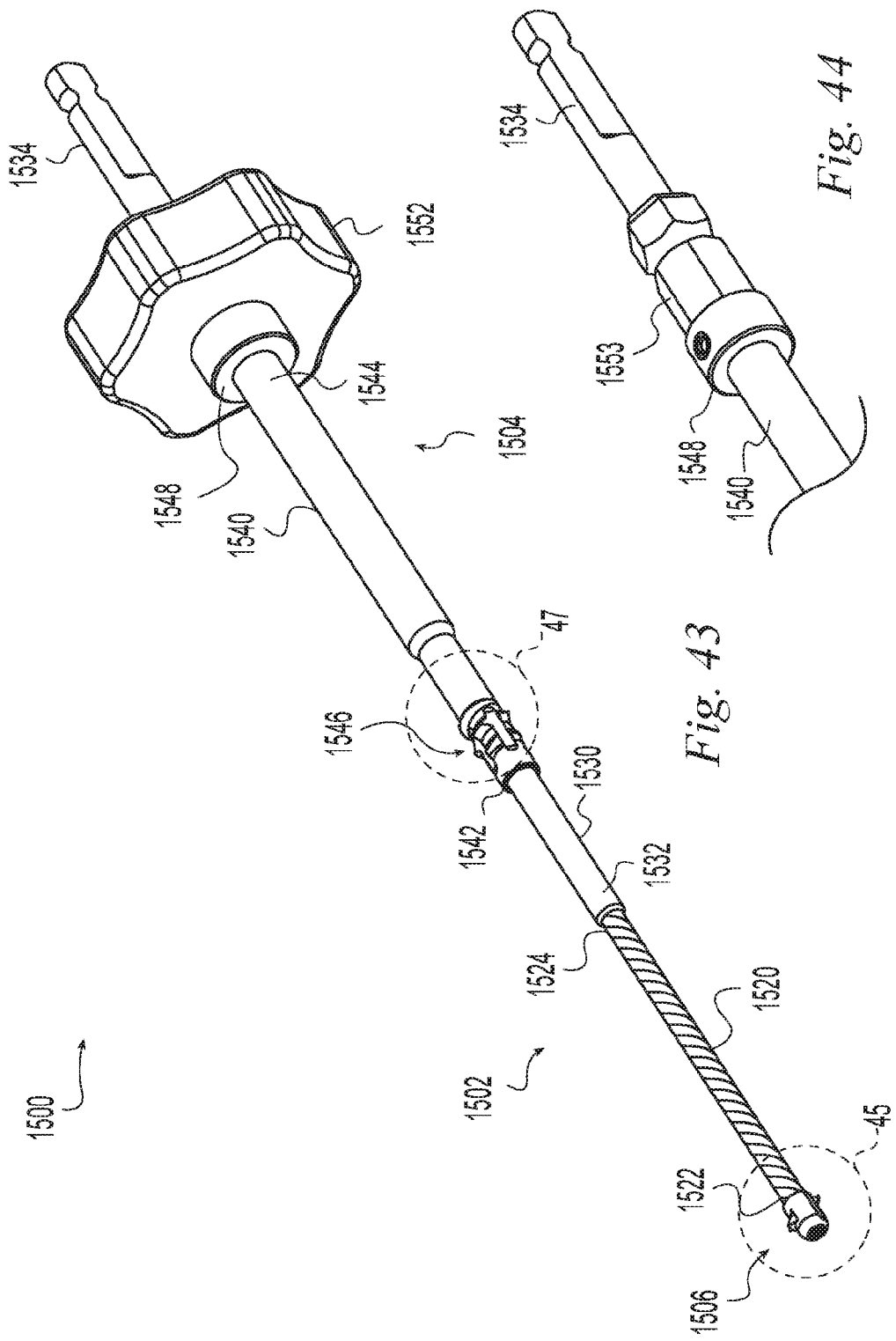

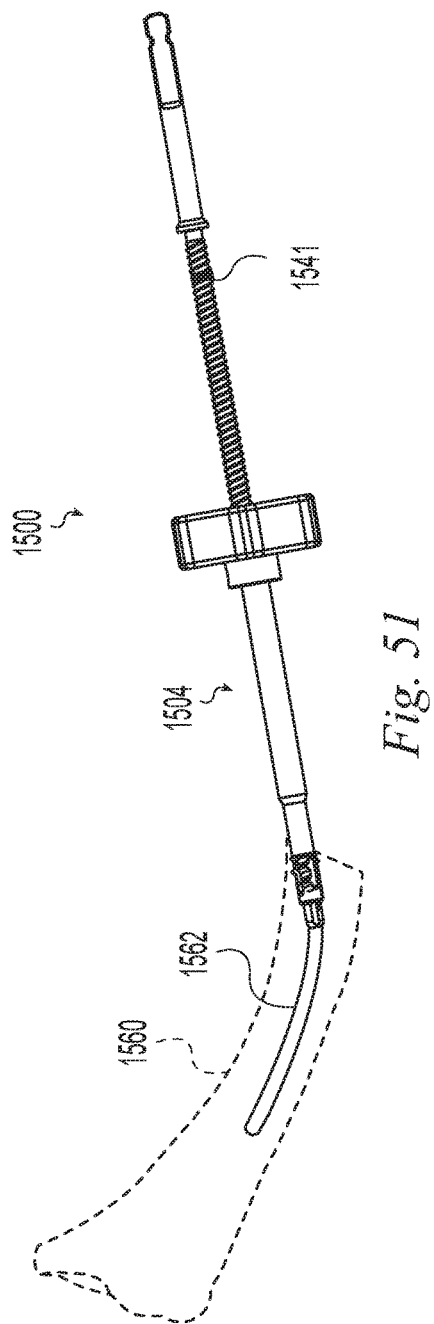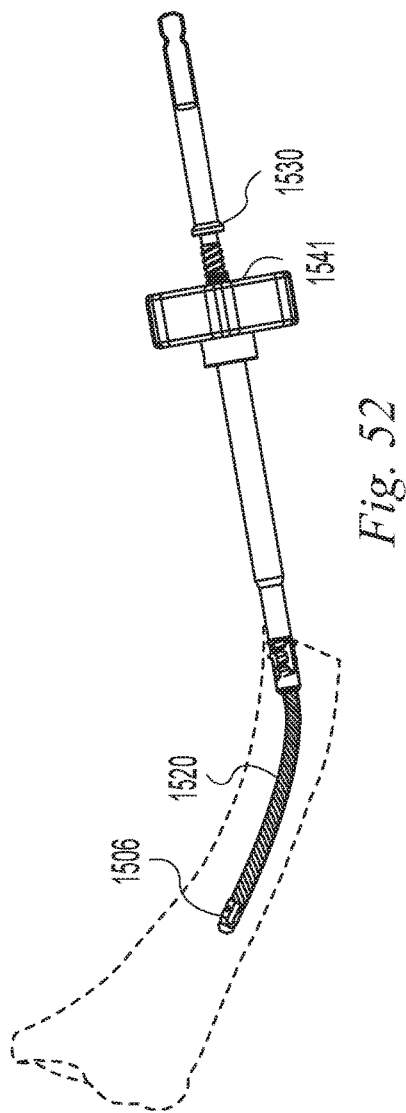
Fig. 51
Fig. 52

METHOD OF BONE FIXATION

CROSS-REFERENCE TO RELATED APPLICATIONS

This application claims the benefit of U.S. Provisional Application 62/268,828, filed Dec. 17, 2015, hereby incorporated by reference.

This application also is a continuation-in-part of U.S. patent application Ser. No. 15/354,634, filed Nov. 17, 2016, which is a continuation-in-part of U.S. patent application Ser. No. 15/285,608, filed Oct. 5, 2016, which is a continuation-in-part of U.S. patent application Ser. No. 15/197,879, filed Jun. 30, 2016, which claims the benefit of U.S. Provisional Application No. 62/191,904, filed Jul. 13, 2015, and U.S. Provisional Application No. 62/238,780, filed Oct. 8, 2015, all of which are hereby incorporated by reference.

This application also is a continuation-in-part of U.S. patent application Ser. No. 15/366,445, filed Dec. 1, 2016, which claims the benefit of U.S. Provisional Application No. 62/266,009, filed Dec. 11, 2015, all of which are hereby incorporated by reference.

FIELD OF THE INVENTION

Examples of the invention relate generally to methods and devices for the surgical treatment of bone and, more particularly, to the stabilization of bones with an intramedullary device.

BACKGROUND

Orthopedic medicine provides a wide array of implants that can be engaged with a bone such as for example to replace a portion of the bone or immobilize a fracture. It is common to utilize threaded components to engage the bone and to form a thread in a bone to receive the threaded components. Prior art surgical instruments are limited to forming a thread along straight paths in bones. However, it would be advantageous to form a thread along a curved path in a bone such as for example to maximize the length of engagement with the bone or to follow a curved portion of the bone such as for example an intramedullary canal. There is a need in the art for implants, instruments and methods that can be used with minimal exposure of the fractured bone and along curved paths.

SUMMARY

Examples of the invention provide devices and methods for stabilizing first and second bone portions relative to one another.

BRIEF DESCRIPTION OF THE DRAWINGS

Various examples of the invention will be discussed with reference to the appended drawings. These drawings depict only illustrative examples of the invention and are not to be considered limiting of its scope.

FIG. 14 is a cross sectional view of a bone implant according to one example of the invention;
FIG. 15 is an exploded cross sectional view of the bone implant of FIG. 14;
FIG. 16 is an exploded side view of a bone implant according to one example of the invention;
FIG. 17 is an assembled sectional view taken along line 17-16 of FIG. 16;
FIG. 18 is an exploded side view of a bone implant according to one example of the invention;
FIG. 19 is an assembled sectional view taken along line 19-19 of FIG. 18;
FIG. 20 is an end view of the bone implant of FIG. 18;
FIG. 21 is a cross sectional view taken along line 21-21 of FIG. 19;
FIG. 22 is a top view of a bone implant according to one example of the invention;
FIG. 23 is an end view of the bone implant of FIG. 22;
FIG. 24 is a front view of the bone implant of FIG. 22;
FIG. 2.5 is a cross sectional view taken along line 25-25 of FIG. 24;
FIG. 43 is a perspective view of a flexible tap according to one example of the invention;
FIG. 44 is a perspective view showing an alternative configuration of the shaft of the flexible tap of FIG. 43.

FIGS. 51 and 52 are plan views illustrating a method of forming a helical thread in a bone using the flexible tap of FIG. 43 according to one example of the invention;

DESCRIPTION OF THE ILLUSTRATIVE EXAMPLES

Figure 1:
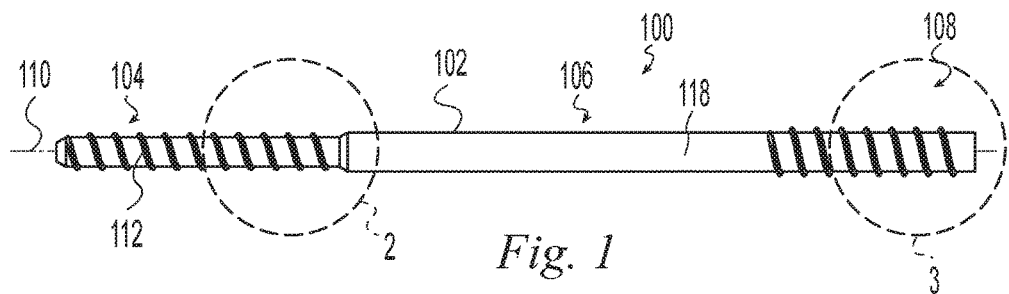
FIG. 1 is a side elevation view of a screw according to one example of the invention.
Figure 2:
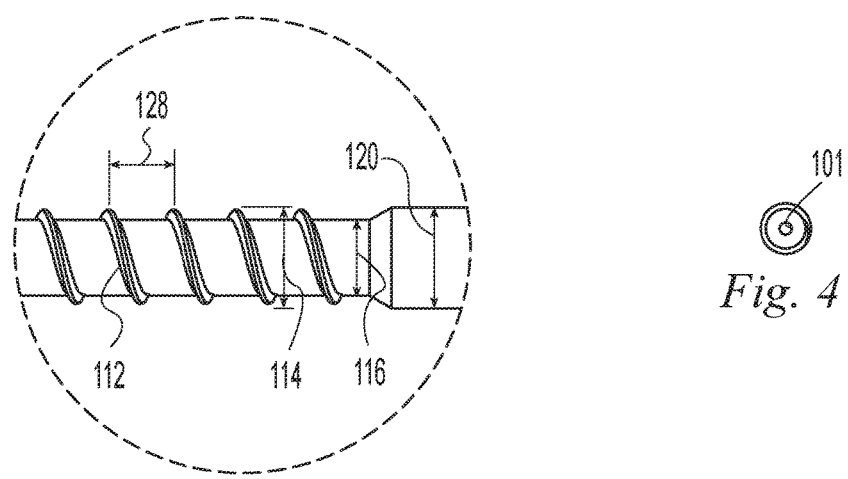
FIG. 2 is a detail view of the screw of FIG. 1.
Figure 4:
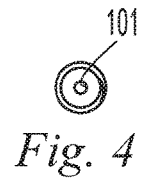
FIG. 4 is an end view of the screw of FIG. 1.
Figure 3:
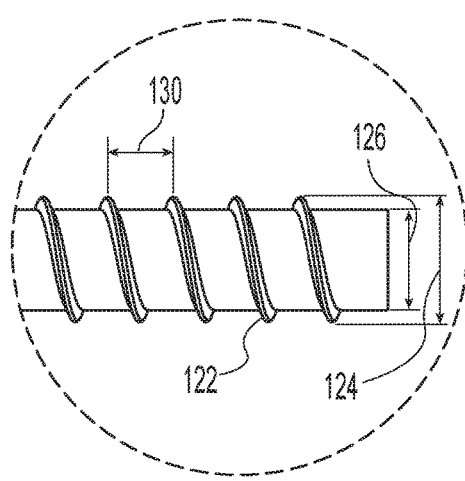
FIG. 3 is a detail view of the screw of FIG. 1.

Examples of the invention relate generally to methods and devices for the surgical treatment of bone and, more particularly, to the stabilization of bones with an intramedullary device. The term "transverse" is used herein to mean to cross at an angle; i.e. not parallel. The term includes, but is not limited to, right angles.

FIGS. 1-4 depict a bone implant 100 according to one example of the invention having an elongate body 102 with a distal portion 104, a mid-portion 106 and a proximal portion 108 spaced longitudinally relative to a longitudinal axis 110. The distal portion 104 includes a helical thread 112 having a major diameter 114, a minor diameter 116, and a pitch 128. The mid-portion 106 has a non-threaded outer surface 118 with an outer diameter 120. In the illustrative example of FIGS. 1-4, the mid-portion outer diameter 120 is equal to or greater than the thread major diameter 114. The distal threaded portion 104 is operable to bend as it is threaded into a bone to follow a curved path. For example, the bending stiffness of the distal threaded portion 104 is such that it will bend to follow a curved path in human bone. Such a curved path may be defined, for example, by a curved hole in the bone, a guide wire, or a natural bone feature such as a non-linear intramedullary canal bounded by cortical bone. This is distinct from prior art threaded implants which if started on a curved path in human bone would, when advanced, continue in a straight line and thus deviate from the curved path and form their own, straight, path through the bone. Preferably the bending stiffness of the threaded distal portion 104 is lower than the bending stiffness of the mid-portion 106. The relatively lower bending stiffness of the threaded distal portion 104 causes the threaded distal portion to bend to follow a curved path while the relatively higher bending stiffness of the mid-portion causes the mid-portion to remain straight to stabilize first and second bone portions relative to one another at a bone interface such as at a fracture, osteotomy, or fusion site. The difference in bending stiffness between the threaded distal portion 104 and the mid-portion 106 may be achieved in different ways. For example, the threaded distal portion 104 and the mid-portion 106 may be made of different materials and/or may have different sectional moduli. In the illustrative example of FIGS. 1-4, the threaded distal portion 104 and the mid-portion 106 have different sectional moduli. The threaded distal portion minor diameter 116 is less than the outer diameter 120 of the mid-portion 106 and the threaded distal portion major diameter is less than or equal to the outer diameter 120 of the mid-portion 106. Preferably, the ratio of the bending stiffness of the mid-portion 106 to the bending stiffness of the threaded distal portion 104 is in the range of 1.5:1 to 100:1. More preferably, the ratio is in the range of 2:1 to 20:1. For example, implants according to examples of the present invention and suitable for internal fixation of a clavicle fracture and that fall within these ranges may have a major diameter 114 in the range of 4-6.5 mm, a minor diameter 116 in the range of 2.5-3.5 and a cannulation 101 with a diameter in the range of 1-2 mm. Preferably, the implant 100 is made, at least in part, of a polymer.

Table 1 compares the calculated load required to bend a cantilevered tube of 3 mm outside diameter and 1.5 mm inside diameter around a radius of 50 mm and an arc length of 26 mm for different materials. The titanium and stainless steel alloys are predicted to have a required load approximately 10 times that of the PEEK and PLLA. These loads would be greater than the bone could withstand and a threaded device made of those materials would not follow a curved path in the bone but would instead cause the bone to fail. In the case of the highly cold worked stainless steel, even if the bone could withstand the load, the implant would fail since the minimum bend radius before failure of the implant is greater than 50 mm.

TABLE 1

Load at 50 mm bend radius

| Material | Yield Stress (MPa) | Failure Stress (MPa) | Yield Strain (%) | Failure Strain (%) | Flexural Modulus (MPa) | Load (N) |
|---|---|---|---|---|---|---|
| PEEK ASTM F2026 | 100 | 115 | 2.5% | 20% | 4 | 9.8 |
| PLLA | 90 | 100 | 2.6% | 25% | 3.5 | 8.7 |
| Ti—6Al—4V ELI ASTM F136 | 880 | 990 | 0.8% | 14% | 114 | 91.7 |
| 316LVM Stainless Steel ASTM F899 | 1468 | 1696 | 0.7% | 3% | 197 | Not possible |

Another way to quantify the bending stiffness of the threaded distal portion 104 is by the amount of torque required to turn the threaded distal portion 104 into a curved bone hole having a specified radius of curvature. For example, the threaded distal portion 104 preferably requires a torque less than 20 in-lbs to turn the distal threaded portion 104 into a bone to follow a curved path having a radius of curvature of 50 mm. More preferably the required torque is less than 10 in-lbs. More preferably the required torque is less than 5 in-lbs. More preferably the required torque is approximately 2 in-lbs.

Table 2 compares the measured torque required to advance a threaded tube 25 mm into a 50 mm threaded radius formed in a rigid test block. The tubes were all machined to the same geometry but of different materials. The thread major diameter was 4.25 mm, the minor diameter was 3.0 mm and the inner diameter of the tube was 1.5 mm. A rigid block was prepared having a curved, threaded path. Such a path has a pitch that is wider on the outside of the curve and a pitch that is narrower on the inside of the curve corresponding to the shape of the thread when it is curved.

Multiple samples of each tube were inserted into the block over an arc length of 25 mm. The maximum torque for each revolution was measured and it was found that the torque increased for each revolution. In Table 2, the range is the range of torque values from the first to the last revolution. The average is the average of the torque values for all revolutions. The peak is the highest torque value and in all cases occurred in the last revolution. However, the torque values for each material were relatively constant over the last few revolutions. The titanium and stainless steel alloys had measured torque values approximately 10 times that of the PEEK. These tests were conducted using a threaded block made of tool steel with a strength greater than that of the materials being tested in order to compare the torque values. As pointed out relative to Table 1, the loads generated from the metal implants would be greater than the bone could withstand and a threaded device as described herein made of these metals would not follow a curved path in the bone but would instead cause the bone to fail.

TABLE 2

Torque to thread around rigid 50 mm radius

| Material | Range (in-lbs) | Average (in-lbs) | Peak (in-lbs) |
|---|---|---|---|
| PEEK ASTM F2026 | 0-2.0 | 1.4 | 2.0 |
| Ti—6Al—4V ELI ASTM F136 | 0.7-25 | 16 | 25 |
| 316LVM Stainless Steel ASTM F899 | 0.5-20 | 13 | 20 |

In addition to bending stiffness advantages, having the threaded distal portion major diameter less than or equal to the outer diameter 120 of the mid-portion 106 allows the distal threaded portion 104 to pass through a passage in a bone that will be a sliding or press fit with the mid-portion 106. A bone implant so configured, as shown in the illustrative example of FIGS. 1-4, can have an intramedullary canal filling mid-portion 106 providing solid support to a bone interface and a relatively bendable distal threaded portion 104 following a curved path such as for threading into a distal portion of a curved bone to secure the implant in the bone.

The proximal portion 108 may be identical to the mid-portion 106. Alternatively, the proximal portion may have a positive driver engagement feature (not shown) such as internal or external non-circular surfaces, profiles, or holes. For example, an internal or external slotted, threaded, triangular, square, hexagonal, hexalobular, or other drive feature may be provided. In addition, as shown in the illustrative example of FIGS. 1-4, the proximal portion 108 may include an optional external helical thread 122 able to engage a bone portion to provide proximal fixation of the implant. For example, the proximal thread 122 may have a major diameter 124, a minor diameter 126, and a pitch 130. In the illustrative example of FIGS. 1-4, the mid-portion outer diameter 120 is equal to the proximal thread minor diameter 126 and the distal thread major diameter 114. The proximal portion may alternatively, or in addition, receive a locking member such as a pin or screw transverse to the longitudinal axis to lock a proximal bone portion to the nail. The locking member may be drilled through the proximal portion. Preferably, the proximal portion has one or more transverse holes formed through it for receiving the locking member.

The distal and proximal thread pitches 128, 130 may advantageously be the same or different depending on the application. For example, to stabilize a fracture, the implant 100 may be inserted into a bone across the fracture so that the distal thread 112 is engaged with bone distal to the fracture and the proximal thread 122 is engaged with bone proximal to the fracture. If the bone portions on either side of the fracture are reduced to a desired final position prior to inserting the implant 100, then it is advantageous for the thread pitches 128, 130 to be equal so that insertion of the implant does not change the relative positions of the bone portions. If on the other hand, it is desirable to move the bone portions relative to one another by the action of inserting the implant then it is advantageous for the pitches 128, 130 to be different. For example, to move the bone portions closer together to reduce the fracture, the distal thread pitch 128 may be made greater than the proximal thread pitch 130 so that with the distal thread 112 engaged distally and the proximal thread 122 engaged proximally, further advancing the implant causes the distal bone portion to move proximally relative to the implant faster than the proximal bone portion moves proximally and thus move the bone portions closer together. Alternatively, to move the bone portions further apart to distract the fracture, the distal thread pitch 128 may be made smaller than the proximal thread pitch 130 so that with the distal thread 112 engaged distally and the proximal thread 122 engaged proximally, further advancing the implant causes the distal bone portion to move proximally relative to the implant more slowly than the proximal bone portion moves proximally and thus move the bone portions further apart. Preferably, the bone implant 100 has a through passage, or cannulation 101, coaxial with the longitudinal axis 110 to permit the bone implant 100 to be inserted over a guide wire.

Figure 5:
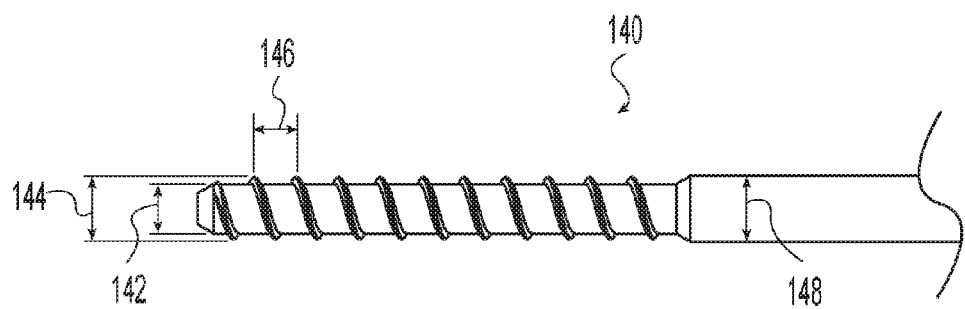
FIGS. 5-7 are side views of a set of differently sized screws like that of FIG. 1.
Figure 6:
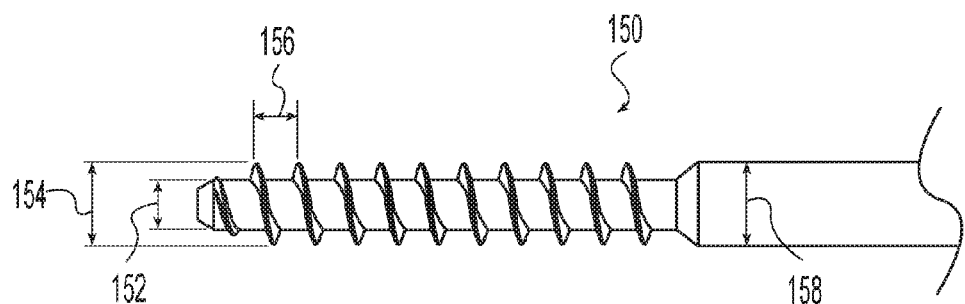
Figure 7:
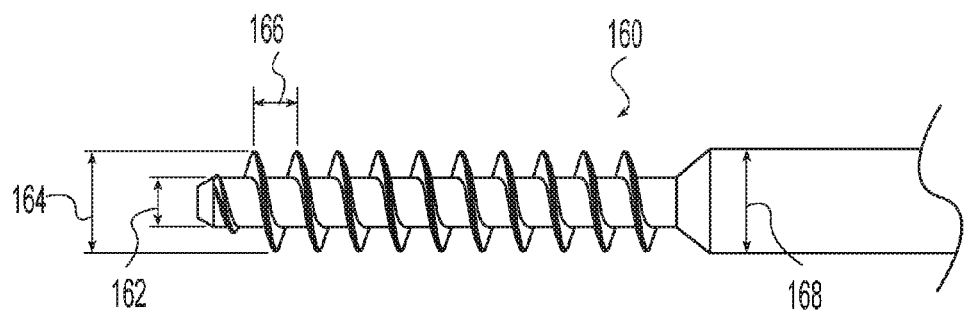

The bone implant 100 of FIGS. 1-4, may advantageously be provided in a set containing a plurality of threaded implants as shown in the illustrative example of FIGS. 5-7. For example, it is advantageous in a surgical procedure to minimize the number of steps and the amount of time needed to complete the procedure. In a bone fixation procedure, a surgeon often makes an initial sizing decision based on medical imaging. During the procedure, it may become expedient to change the predetermined size based on observation of the surgical site or the fit of trial implants or instruments. For example, a surgeon may determine initially that a smaller threaded implant is appropriate. However, during preparation of the site, the surgeon may determine that a larger threaded will better grip the bone or fill, for example, a canal in the bone. The illustrative set of implants shown in FIGS. 5-7 facilitates changing between sizes. Each implant thread 140, 150, 160 in the set has a minor diameter 142, 152, 162, a major diameter 144, 154, 164, and a pitch 146, 156, 166. The minor diameters 142, 152, 162 are equal to one another so that a single diameter drill will provide an initial bore hole appropriate for all the threads in the set. The pitches 146, 156, 166 are equal to one another so that all of the threads in the set will threadably engage a helical thread of the same pitch. The major diameters 144, 154, 164 may increase to provide progressively more bone purchase or, for example, to span increasing larger intramedullary canals. For example, with the set of implants of the illustrative example of FIGS. 5-7, a surgeon may drill a hole equal to the minor diameters 142, 152, 162 and then tap the hole with a tap corresponding to the thread of the smallest major diameter thread 140. The tactile feedback received by the surgeon as the tap is inserted will indicate to the surgeon if the thread major diameter is sufficient to provide a desired level of bone engagement. For example, the surgeon can feel if the tap is engaging the cortical walls of an intramedullary canal or if the tap is in softer cancellous bone. If the surgeon determines that greater engagement is desired, the surgeon can next tap the hole with a tap corresponding to the thread of the next larger major diameter thread 150. Since the minor diameters 142, 152, 162 and thread pitches 146, 156, 166 are the same for all of the implants in the set, the next tap will thread into the previously tapped hole and increase the bone thread major diameter without damaging the bone thread. Once the desired bone engagement is achieved, the surgeon may then insert the desired implant 140, 150, 160. If in tapping the larger major diameter thread, the surgeon determines that the bone is providing too much resistance, the surgeon may revert to the smaller sized implant since the threads are still compatible. Alternatively to using a separate tap, the screw threads may be configured as self-tapping so that the implants may be threaded directly into the bored hole.

In addition to the sizing advantages of having the same minor diameter 142, 152, 162 across a family of implants, it is also advantageous because the distal threaded portion of each implant will have a similar bending stiffness to each of the other implants 140, 150, 160 since the continuous wall of the minor diameter contributes much more to the bending stiffness than the helical thread itself. This similar bending stiffness means that they can be inserted around a similar bending radius with a similar torque.

In the illustrative example of FIGS. 5-7, each implant 140, 150, 160 has a mid-portion diameter 148, 158, 168 equal to the corresponding major diameter 144, 154, 164. The increasing mid-portion diameters provide progressively less flexible mid-portions across the set of implants and, for example, canal filling for increasingly larger bones if used in the intramedullary canal. If the implants incorporate the optional increasing mid-portion diameter as shown, then it is desirable to re-drill the mid-portion of the bone hole to accommodate the mid-portion when an increase in implant size is desired. However, the distal, threaded portion of the bone hole does not need to be re-drilled so the implant threads will not be damaged by drilling. The mid-portion diameter may also be larger than the corresponding distal thread major diameter to further increase the mid-portion stiffness.

Alternatively to, or in addition to, the threaded distal portion 104 and mid-portion 106 having different sectional moduli, the threaded distal portion 104 and mid-portion 106 may have different material properties such as two different materials or different conditions of the same material to produce a difference in bending stiffness between them.

Figure 11:
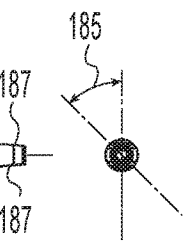
FIG. 11 is an end view of the screw of FIG. 8.
Figures 12, 13:
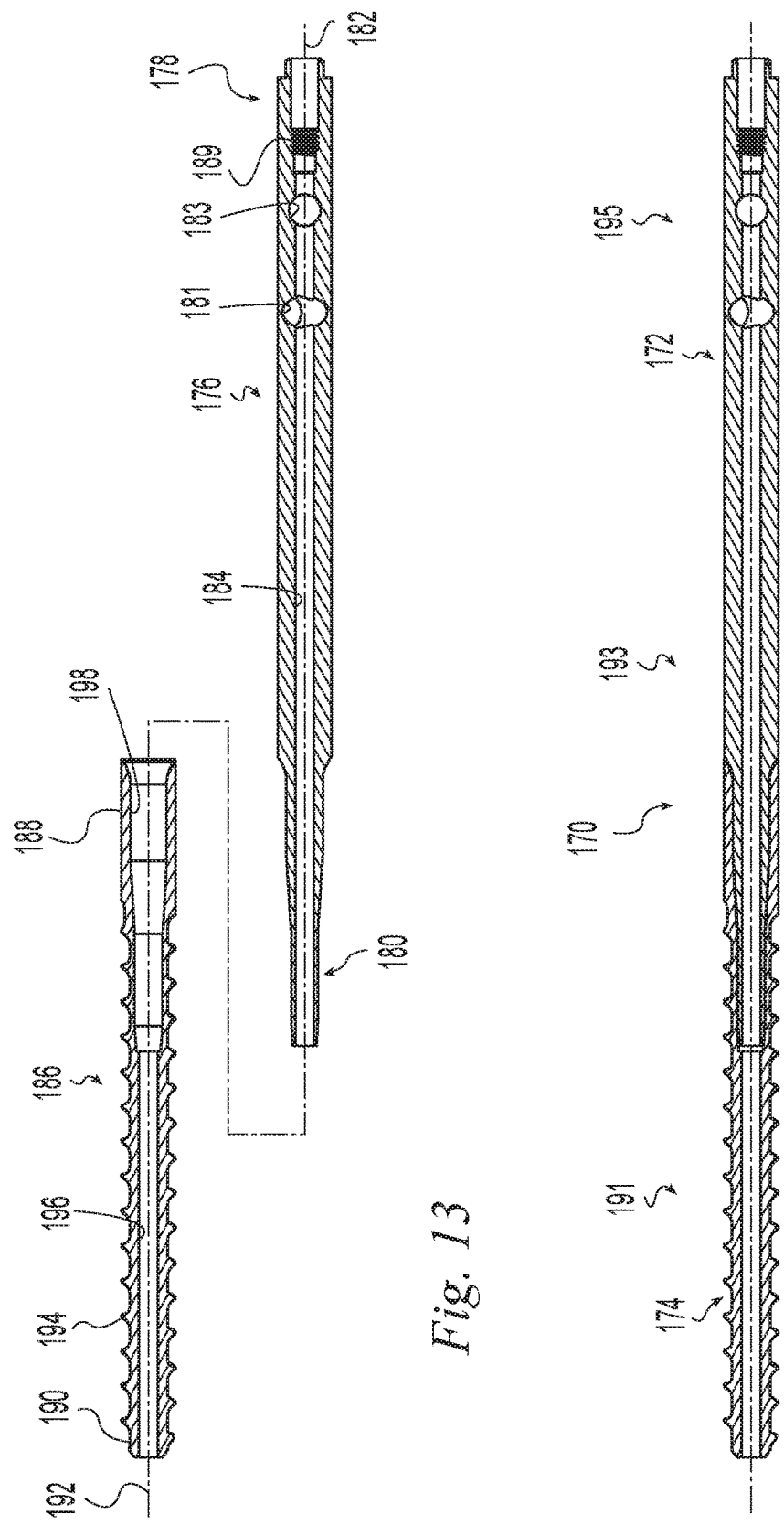
FIG. 12 is a sectional view taken along line 12-12 of FIG. 9.
FIG. 13 is an exploded sectional view taken along line 12-12 of FIG. 9.

In the illustrative example of FIGS. 8-13, an implant 170 has separate first and second members 172, 174 permanently joined together. The first member 172 includes an elongate body 176 with a proximal end 178, a distal end 180, a longitudinal axis 182, and an axial through passage 184. The proximal end 178 of the first member includes a pair of transverse through passages 181, 183. Each transverse passage 181, 183 defines a longitudinal axis and the axes form an angle 185 between them about the longitudinal axis 182 as best seen in FIG. 11. Providing more than one transverse through passage increases options for attaching the implant to bone fragments and options for fixation direction. Both passages may be used for fixation or the one that is most conveniently located may be used. Preferably the angle 185 is in the range of 0 to 90 degrees. More preferably the angle 185 is in the range of 20 to 90 degrees. In the illustrative example of FIGS. 8-13, the angle 185 is 45 degrees. The proximal end 178 also includes opposed flats 187 for engaging a driver in torque transmitting relationship. An internal thread 189 within the passage 184 is engageable with, e.g., a threaded draw bar to secure the first member to a driver.

The second member 174 includes an elongate body 186 with a proximal end 188, a distal end 190, a longitudinal axis 192, an external helical thread 194, and an axial through passage 196. The distal end 180 of the first member 172 and the proximal end 188 of the second member 174 may have complementary geometries to aid in joining them. In the illustrative example of FIGS. 8-13, the distal end 180 of the first member has a stepped conical taper and the proximal end 188 of the second member has a corresponding stepped conical socket 198. The mating surfaces may be any suitable shape as determined by the materials and joining technique including but not limited to plug and socket joints (as shown), scarf joints, butt joints, dovetail joints, finger joints, and lap joints. The joint may be reinforced with a third component such as an adhesive, pin, or key. The joint may be formed by mechanical interlock, chemical bonding, molding, welding or other suitable joining process. The final assembled implant 170, has a distal portion 191, a mid-portion 193 and a proximal portion 195 and may have the thread forms, diameters and relationships as described relative to the examples of FIGS. 1-7.

The first and second components 172, 174 may be made of different materials or different conditions of the same material. For example, they may be made of polymers, metals, or ceramics. Metals may include stainless steel alloys, titanium, titanium alloys, cobalt-chromium steel alloys, nickel-titanium alloys, and/or others. Polymers may include nonresorbable polymers including polyolefins, polyesters, polyimides, polyamides, polyacrylates, poly(ketones), fluropolymers, siloxane based polymers, and/or others. Polymers may include resorbable polymers including polyesters (e.g. lactide and glycolide), polyanhydrides, poly (aminoacid) polymers (e.g. tyrosine based polymers), and/or others. Other possible materials include nonresorbable and resorbable ceramics (e.g. hydroxyapatite and calcium sulfate) or biocompatible glasses. They may be made of homogenous materials or reinforced materials. They may be made of crystallographically different materials such as annealed versus cold worked. It is preferable for the mid portion 193 and proximal portion 195 to have a higher bending stiffness than the distal portion 191 and the distal portion preferably has a bending stiffness low enough for it to be inserted along a curved path in bone.

In a first example, the first component may be made of a metal with a relatively high degree of cold work and the second component of a metal with a relatively low amount of cold work such as for example annealed and cold worked stainless steel. The components may be joined for example by welding. However, as discussed relative to Table 1, most metals are far too stiff to allow threading along a curved path in a bone within suitable torsional loads.

Preferably the distal portion is made of a polymer. In a second example, the first component is made of a metal, such as stainless steel or a titanium alloy, and the second component is made of a polymer such as polyetheretherketone (PEEK) or a polylactide polymer (e.g. PLLA). The components may be joined such as for example by threading them together.

Preferably both components are made of polymers. In a third example, the first and second components are both made of non-resorbable polymers. For example, the first component may be made of fiber reinforced PEEK (e.g. Invibio PEEK-Optima™ Ultra-Reinforced) and the second component may be made of neat (unreinforced) PEEK (e.g. Invibio PEEK-Optima™ Natural). The fiber reinforced PEEK is strong while the neat PEEK is relatively flexible allowing it to be easily threaded around a curved path even while having a relatively large bone filling diameter. The components may be joined, e.g. by molding the components as a continuous matrix with first component fiber reinforcement and second component neat polymer with polymer chains extending across the joint interface. In the illustrative example of FIGS. 8-13, the second component is relatively more transparent to laser radiation than the first component and the parts are joined by laser welding at the conical interface. The laser energy passes relatively easily through the second component and is absorbed by the first component so that localized heating at the conical interface takes place causing the polymer constituent of the two components to fuse together.

In a fourth example, the first and second components are made of resorbable polymers. For example, the mid-portion may be made of a glass fiber reinforced PLLA (e.g. Corbion-Purac FiberLive™) and the distal portion may be made of neat PLLA.

Alternatively, the first member 172 and second member 174 may form one continuous part with different properties between first and second portions. The difference in properties may be achieved, for example, by different processing (e.g. thermal processing) or blending materials. For example, different polymers may be combined in a single injection mold cavity and formed together. The polymers may be blended so that there is a transition between them. In another example, stiffening and/or strengthening material, e.g. fibers, whiskers, and/or granules, may be selectively incorporated in, e.g., the first portion.

FIGS. 14 and 15 illustrate an example of an implant 270 similar to that of FIGS. 8-13 except that the first member 272 is not cannulated, the first member 272 extends the full length of the second member 274, and the transverse holes 281, 283 are coplanar. The implant 270 may be assembled as with the prior example including by using complimentary screw threads in the proximal region of the second member 274 and mid portion of the first member 272 as indicated by reference number 250. The implant 270 of the example of FIGS. 14 and 15 may be include any of the materials and features described relative to the prior examples. If, for example, the first member 272 is made of a radiographically more opaque material than the second member 274, then the first member will provide a radiographic marker over the entire length of the screw 270 that may be radiographically visualized during and after surgery to confirm implant placement. For example, a metal first component and polymer second component would provide for radiographic visualization of the metal first component. It has been found by the present inventors that the bending stiffness of the distal end of the implant is not materially changed by eliminating the axial through passage of the first component and is essentially unchanged when the bending stiffness of a guide wire is accounted for which was optionally used with the previous cannulated implant examples. The guide wire is not necessary inasmuch as the implant 270 will follow a curved path receiving it. The transverse holes 181, 183 may be provided in any number or not at all as desired but it has been found that one is sufficient and two provides the user with additional fixation choice.

FIGS. 16 and 17 illustrate a bone implant 400 useful for stabilizing bone fractures according to one example of the invention. The bone implant 400 includes a body 402 defining a longitudinal axis 404 extending between a proximal end 406 and a distal end 408. The body has an elongate distal portion 410 having an outer surface 412 defining a screw thread 414 having a minor diameter 416 and a major diameter 418. The body has an elongate proximal portion 430 having a non-threaded outer surface 432. Passages 434 and 436 are each formed through the proximal portion 430 transverse to the longitudinal axis from a first opening 438, 440 on the surface of the proximal portion to a second opening 442, 444 on the surface of the proximal portion. A driver engaging feature is formed at the proximal end for engaging a driver in torque transmitting relationship. The driver engaging feature may be a male feature or a female feature. Preferably it is a polygonal feature engageable with a correspondingly shaped driver. In the example of FIGS. 16 and 17, the driver engaging feature is a hexagonal socket 446 formed in the proximal end of the implant. The socket 446 includes a threaded recess 448 for threaded engagement with other tools such as a driver retaining draw rod, a cross pinning guide, or the like. As with all of the examples herein, the distal portion is responsive to rotation of the implant to thread into a bone and advance the bone implant into the bone. This rotary advancement action is advantageous compared to typical bone nails that are impacted into the bone since the threaded advancement is less stressful to the bone and surrounding tissues. As the distal portion is threaded into the bone, it pulls the proximal portion into the bone. The distal threaded portion is anchored in the bone by the thread 414. The smooth proximal portion may be positioned to span a fracture so that, for example, no sharp edges are engaged with the fracture and no stress concentrating features that might weaken the implant span the fracture.

In the example of FIGS. 16 and 17, the proximal portion has a length 450 measured from the free proximal end 406 to the proximal start 452 of the threads of the distal portion. The proximal portion has a maximum diameter. For example for a conical or cylindrical proximal portion the maximum diameter is simply the largest diameter along the proximal portion. For an ovoid proximal portion, the maximum diameter would be the major diameter of the elliptical cross section. For other shapes, such as fluted proximal portions, the maximum diameter is the maximum dimension normal to the longitudinal axis 404 of the proximal portion. The maximum diameter is preferably constant over a portion of the proximal portion length to provide a uniform thickness for spanning a fracture. For example, the maximum diameter is preferably uniform over at least one-fourth of the proximal portion length; more preferably at least one-third; more preferably at least one-half; more preferably more than one-half. In the illustrative example of FIGS. 16 and 17, the proximal portion has a constant cylindrical diameter over its entire length. The driver engaging feature preferably has a maximum dimension normal to the longitudinal axis that is less than or equal to the maximum diameter of the proximal portion so that, for example, the proximal end of the bone implant may be seated below the bone surface.

Figure 8:
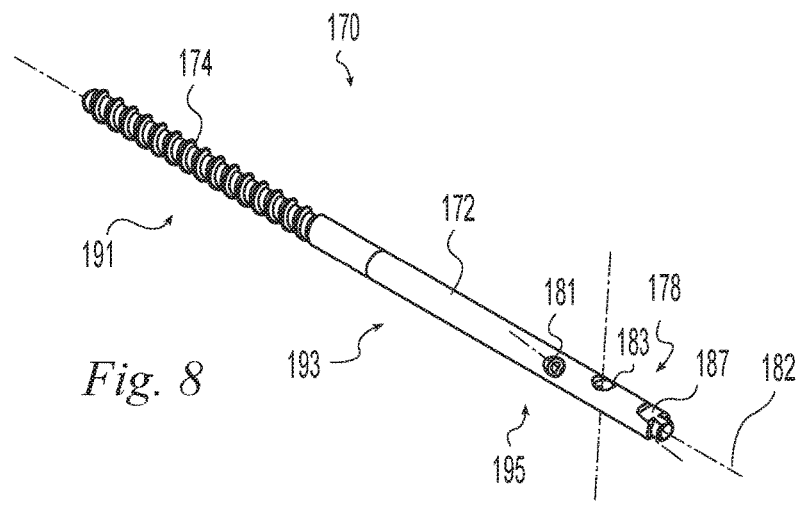
FIG. 8 is a perspective view of a screw according to one example of the invention.
Figure 9:
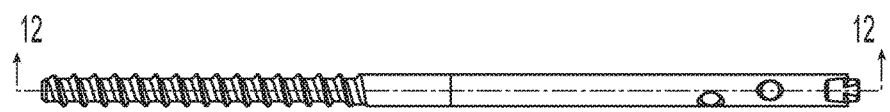
FIG. 9 is a top plan view of the screw of FIG. 8.
Figure 10:
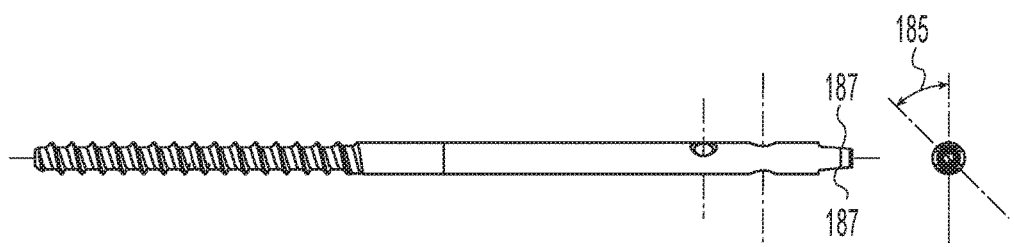
FIG. 10 is a side elevation view of the screw of FIG. 8.

The bone implant may be a unitary construct, like shown in the illustrative example of FIGS. 1-4, in which the proximal and distal portions are formed of one continuous material. Optionally, the proximal and distal portions may be separate components joined together as shown in the example of FIG. 8 and the example of FIG. 14. In the illustrative example of FIGS. 16 and 17, the bone implant includes a sleeve 460 surrounding a separate core 462. The sleeve and core are joined together to form the body. Various methods may be used to join the sleeve and core. For example, they may be threaded, pinned, bonded, welded, or otherwise joined. In the example of FIGS. 16 and 17, the sleeve is threaded onto the core via an internal thread 464 and corresponding male thread 466 formed on the core. The sleeve is further pinned to the core with a pin 468 pressed through holes 470, 472 in the sleeve wall and in the core.

As described relative to previous examples, it is desirable for the distal portion to have a lower bending resistance than the proximal portion. In one example, the sleeve is at least partially formed of a polymer and the core is at least partially formed of a metal. In the example of FIGS. 16 and 17, the sleeve is formed from a polymer and includes the distal screw thread while the core is formed from a metal and includes the proximal portion. In one example, the core is made of a biocompatible titanium alloy and the sleeve is made of a biocompatible poly(ketone) polymer such as, for example, polyetheretherketone. In another example, the core is made of a suitable biocompatible metal and the sleeve is made of a resorbable polymer so that, over time, the sleeve will resorb in the patient's body and allow gradually increasing motion of the bone and load transfer to the bone to promote healing. The core may extend partway toward the distal end as in the example of FIG. 8, all the way to the distal end as in the example of FIG. 14, or it may extend past the distal end as in the example of FIG. 16. With the tip 480 of the core extending beyond the distal end, the tip 480 provides an easier start of the implant into a hole in the bone and, as shown in the example of FIGS. 16 and 17, the tip 480 provides a smooth bearing surface for following a curved path in a bone.

FIGS. 18 through 21 illustrate a bone implant 500 similar to that of FIGS. 16 and 17. The bone implant 500 includes a core 502 and a sleeve 504. In the example of FIGS. 18 through 21, the smooth proximal portion 506 is more evenly proportioned over the core and sleeve. Also, the core steps up more gradually in diameter from the distal end 508 to the proximal end 510 resulting in a more gradual transition in bending stiffness over three zones. In a first zone 512, a relatively thin portion of the core is surrounded by a relatively thick portion of the sleeve. In a second zone 514, a relatively thicker portion of the core is surrounded by a relatively thinner portion of the sleeve. In a third zone 516, only a relatively thicker portion of the core remains. Also, in the example of FIGS. 18 through 21 a slip resisting feature is provided on the core and a polymer sleeve is molded to the core so that the polymer and slip resisting feature interdigitate. The slip resisting feature may be knurling, threads, grooves, splines, spikes, holes, or other features. The slip resisting feature may be oriented to enhance torque transfer, longitudinal force transfer, or otherwise oriented. In the example of FIGS. 18 through 21, the slip resisting feature includes longitudinal splines 518 to enhance the ability to transfer torque between the core and sleeve. Longitudinal force transfer is sufficiently accommodated by the bonding of the sleeve to the core during the molding process. The proximal end 510 includes an hexalobular socket 511 for engaging a driver.

In use, the preceding implants may be provided in an appropriate size and inserted into a bone to span a fracture in the bone. Preferably the proximal portion of the implant spans the fracture. The arrangement of a smooth proximal portion and a threaded distal portion permits rotating the bone implant to cause the threaded distal portion to engage the bone and pull the proximal portion of the bone implant into a positioning spanning the fracture. In the case of an implant comprising a resorbable polymer, the polymer will resorb over time in the patient to gradually transfer load to and permit motion of the bone to enhance healing of the fracture. One or more pins or screws may be inserted so that they extend through one or more of the passages in the proximal end and through a portion of the bone to fix the bone to the proximal portion of the implant. For example with the distal end of the bone implant fixed by engagement of the distal threads in a distal portion of the bone a proximal portion of the bone may be secured with pins or screws as described. This may be used to hold compression or distraction on bone portions on opposing sides of the fracture or to attach loose bone fragments.

FIGS. 22-25 illustrate a bone implant 600 similar to the preceding examples inasmuch as it has a smooth rod-like proximal portion 602 and a threaded distal portion 604. The proximal portion 602 has one or more transverse passages through the proximal portion, each passage extending from a first opening on the surface of the proximal portion to a second opening on the surface of the proximal portion. The distal portion may be threaded into a bone to secure the implant 600 to the bone at the distal end. The proximal portion, is preferably positioned to bridge a fracture to provide support to the fracture while the fracture heals. The transverse passages can receive a fastener such as a pin, wire, screw or the like to connect the proximal portion to bone. In the illustrative example of FIGS. 22-25, the implant 600 is configured for placement in the intramedullary canal of a fibular bone to support a fracture of the fibular bone and optionally to support screws for reinforcing the syndesmosis joint of an ankle. The proximal portion includes a first pair of holes 606 perpendicular to the implant longitudinal axis 608 and angled relative to one another about the axis 608. The first pair of holes 606 is positioned nearer the proximal end 610 of the implant to receive fasteners for attaching the implant 600 to a portion of the bone, or fragment, proximal to a fracture. The implant further includes a second pair of holes 612 perpendicular to the implant longitudinal axis and, in this example, parallel to one another. The second pair of holes 612 is positioned distal to the first pair and is arranged to receive fasteners that extend through the fibula and into the tibia to reinforce the syndesmosis joint. In the illustrative example of FIGS. 22-25 the implant 600 is a unitary construction. In other embodiments, the implant 600 may include a greater or a lesser number of transverse holes or no holes at all. The transverse holes may be perpendicular to the axis 608 as shown or at any other angle suitable for the target anatomy. The implant may be made of two or more parts joined together as in the previous examples. The distal portion 604 includes a distal thread 620 having a major diameter 622, a minor diameter 624, and a pitch 626.

The various examples according to the invention have a decreased bending stiffness of the distal portion relative to the proximal portion using various strategies including different section moduli and different materials. It is desirable for the distal thread to have a lower bending stiffness than conventional bone screws of a similar major diameter. In the illustrative examples, the bending stiffness of the distal portion may be lowered by utilizing a novel screw thread. For example, a thread according to an example of the invention has a smaller minor diameter and/or a larger pitch than a conventional bone screw thread. Table 3 compares illustrative examples of screw thread geometry according to examples of the invention to the industry standard bone screw threads described in ASTM F543.

TABLE 3

Screw thread geometry - Dimensions in mm

| A Thread | B Maj. dia. max | C Maj. dia. min | D Min. dia. max | E Min. dia. min | F Pitch | B/E ratio | C/D ratio | B/F ratio | C/F ratio | D/F ratio | E/F ratio |
|---|---|---|---|---|---|---|---|---|---|---|---|
| ASTM HA 1.5 | 1.50 | 1.35 | 1.10 | 1.00 | 0.50 | 1.50 | 1.23 | 3.00 | 2.70 | 2.20 | 2.00 |
| ASTM HA 2.0 | 2.00 | 1.85 | 1.30 | 1.20 | 0.60 | 1.67 | 1.42 | 3.33 | 3.08 | 2.17 | 2.00 |
| ASTM HA 2.7 | 2.70 | 2.55 | 1.90 | 1.75 | 1.00 | 1.54 | 1.34 | 2.70 | 2.55 | 1.90 | 1.75 |
| ASTM HA 3.5 | 3.50 | 3.35 | 2.40 | 2.25 | 1.25 | 1.56 | 1.40 | 2.80 | 2.68 | 1.92 | 1.80 |
| ASTM HA 4.0 | 4.00 | 3.85 | 2.90 | 2.75 | 1.50 | 1.45 | 1.33 | 2.67 | 2.57 | 1.93 | 1.83 |
| ASTM HA 4.5 | 4.50 | 4.35 | 3.00 | 2.85 | 1.75 | 1.58 | 1.45 | 2.57 | 2.49 | 1.71 | 1.63 |
| ASTM HA 5.0 | 5.00 | 4.85 | 3.50 | 3.35 | 1.75 | 1.49 | 1.39 | 2.86 | 2.77 | 2.00 | 1.91 |
| ASTM HB 4.0 | 4.00 | 3.85 | 1.90 | 1.75 | 1.75 | 2.29 | 2.03 | 2.29 | 2.20 | 1.09 | 1.00 |
| ASTM HB 6.5 | 6.50 | 6.35 | 3.00 | 2.85 | 2.75 | 2.28 | 2.12 | 2.36 | 2.31 | 1.09 | 1.04 |
| ASTM HC 2.9 | 2.90 | 2.79 | 2.18 | 2.03 | 1.06 | 1.43 | 1.28 | 2.74 | 2.63 | 2.06 | 1.92 |
| ASTM HC 3.5 | 3.53 | 3.43 | 2.64 | 2.51 | 1.27 | 1.41 | 1.30 | 2.78 | 2.70 | 2.08 | 1.98 |
| ASTM HC 3.9 | 3.91 | 3.78 | 2.92 | 2.77 | 1.27 | 1.41 | 1.29 | 3.08 | 2.98 | 2.30 | 2.18 |
| ASTM HC 4.2 | 4.22 | 4.09 | 3.25 | 2.95 | 1.27 | 1.43 | 1.26 | 3.32 | 3.22 | 2.56 | 2.32 |
| ASTM HD 4.0 | 4.03 | 3.97 | 2.95 | 2.89 | 1.59 | 1.39 | 1.35 | 2.53 | 2.50 | 1.86 | 1.82 |
| ASTM HD 4.5 | 4.53 | 4.47 | 2.95 | 2.89 | 2.18 | 1.57 | 1.52 | 2.08 | 2.05 | 1.35 | 1.33 |
| Example 1 | 3.55 | 3.45 | 2.05 | 1.95 | 2.75 | 1.82 | 1.68 | 1.29 | 1.25 | 0.75 | 0.71 |
| Example 2 | 3.25 | 3.10 | 1.50 | 1.35 | 2.25 | 2.41 | 2.07 | 1.44 | 1.38 | 0.67 | 0.60 |
| Example 3 | 5.25 | 5.10 | 3.00 | 2.85 | 2.75 | 1.84 | 1.70 | 1.91 | 1.85 | 1.09 | 1.04 |

Column A is a description of each of the threads being compared. ASTM Type HA threads correspond to the standard for bone screws having a spherical undersurface head, a shallow asymmetrical buttress thread, and a deep screw head. ASTM Type HB threads correspond to the standard for bone screws having a spherical undersurface head, a deep asymmetrical buttress thread, and a shallow screw head. ASTM Type HC threads correspond to the standard for bone screws having a conical undersurface head and a symmetrical thread. ASTM Type HD threads correspond to the standard for bone screws having a conical undersurface head and an asymmetrical thread. Column B is the maximum major diameter for the thread including permitted manufacturing tolerances. Column C is the minimum major diameter for the thread including permitted manufacturing tolerances. Column D is the maximum minor diameter for the thread including permitted manufacturing tolerances. Column E is the minimum minor diameter for the thread including permitted manufacturing tolerances. Column F is the thread pitch. Column B/E is the ratio of the maximum major diameter to the minimum minor diameter and represents the largest major diameter to minor diameter ratio for the thread. Column C/D is the ratio of the minimum major diameter to the maximum minor diameter and represents the smallest major diameter to minor diameter ratio for the thread. Column B/F is the ratio of the maximum major diameter to the pitch and represents the largest major diameter to pitch ratio for the thread. Column C/F is the ratio of the minimum major diameter to the pitch and represents the smallest major diameter to pitch ratio for the thread. Column D/F is the ratio of the maximum minor diameter to pitch and represents the largest minor diameter to pitch ratio for the thread. Column E/F is the ratio of the minimum minor diameter to pitch and represents the smallest minor diameter to pitch ratio for the thread.

Referring to columns B/E and C/D, standard bone screws with a thread major diameter less than 4.0 mm have a major diameter to minor diameter ratio less than 1.7.

Referring to column F of Table 3, standard bone screws with a thread major diameter less than 6.5 mm have a pitch less than 2.2 mm. Standard bone screws with a thread major diameter less than 4.5 mm have a pitch equal to or less than 1.75 mm. Standard bone screws with a thread major diameter less than 4.0 mm have a pitch less than 1.5 mm. Looking at it another way, referring to columns B/F and C/F, standard bone screws have a major diameter to pitch ratio greater than 2. Standard bone screws with a thread major diameter less than 4.0 mm have a major diameter to pitch ratio greater than 2.5. Referring to columns D/F and E/F, standard bone screws have a minor diameter to pitch ratio greater than or equal to 1. Standard bone screws with a thread major diameter less than 4.0 mm have a minor diameter to pitch ratio greater than or equal to 1.75.

Examples of the invention have a thread with a smaller minor diameter and/or a larger pitch than standard bone screws of a similar size to, for example, enable the screw thread to bend to follow a curved path in a bone.

Referring to Example 1 according to the invention, the example thread has a 3.5 mm nominal major diameter, a 2.00 mm nominal minor diameter, a pitch of 2.75 mm, a major diameter to minor diameter ratio between 1.68 and 1.82, a major diameter to pitch ratio between 1.25 and 1.29, and a minor diameter to pitch ratio between 0.71 and 0.75. Comparing Example 1 to ASTM HA 3.5 and ASTM HC 3.5, it is seen that the thread of Example 1 has a minor diameter approximately 15-20% smaller than similar sized standard bone screws. In addition, the thread of Example 1 has a pitch more than double the length of similar sized standard bone screws. The major diameter to minor diameter ratio for the thread of Example 1 is approximately 20-30% greater than for similar sized bone screws. The major diameter to pitch ratio for the thread of Example 1 is less than 50% that of similarly sized standard screws and the minor diameter to pitch ratio for the thread of Example 1 is less than 40% that of similarly sized standard bone screws. With its unconventional decreased minor diameter and increased thread pitch, a thread according to Example 1 made of Ti-6Al-4V has been shown by the present inventors to be able to bend to follow the natural curve of the intramedullary canal of a human fibula.

Referring to Example 2 according to the invention, the example thread has a 3.18 mm nominal major diameter, a 1.43 mm nominal minor diameter, a pitch of 2.25 mm, a major diameter to minor diameter ratio between 2.07 and 2.41, a major diameter to pitch ratio between 1.38 and 1.44, and a minor diameter to pitch ratio between 0.60 and 0.67. Comparing example 2 to ASTM HA 3.5 and ASTM HC 2.9, the most similar sized standard bone screw threads, it is seen that the thread of Example 2 has a minor diameter approximately 30-40% smaller than similar sized standard bone screws. In fact, the thread of Example 2 has a minor diameter smaller than an ASTM HA 2.7 thread and most closely resembles that of the much smaller ASTM HA 2.0 thread. In addition, the thread of Example 2 has a pitch more than double that of similar sized standard bone screws. The major diameter to minor diameter ratio for the thread of Example 2 is approximately 50-65% greater than for similar sized bone screws. The major diameter to pitch ratio for the thread of Example 2 is approximately 50% that of similarly sized standard screws and the minor diameter to pitch ratio for the thread of Example 2 is less than 35% that of similarly sized standard bone screws. With its unconventional decreased minor diameter and increased thread pitch, a thread according to Example 2 made of polyetheretherketone has been shown by the present inventors to be able to bend to follow the natural curve of the intramedullary canal of a human clavicle.

Referring to Example 3 according to the invention, the example thread has a 5.18 mm nominal major diameter, a 2.93 mm nominal minor diameter, a pitch of 2.75 mm, a major diameter to minor diameter ratio between 1.70 and 1.84, a major diameter to pitch ratio between 1.85 and 1.91, and a minor diameter to pitch ratio between 1.04 and 1.09. Comparing example 3 to ASTM HA 5.0, the most similar sized standard bone screw thread, it is seen that the thread of Example 3 has a minor diameter approximately 15% smaller than similar sized standard bone screws. In addition, the thread of Example 3 has a pitch approximately 60% greater than similar sized standard bone screws. The major diameter to minor diameter ratio for the thread of Example 3 is approximately 23% greater than for similar sized bone screws. The major diameter to pitch ratio for the thread of Example 3 is approximately 67% that of similarly sized standard screws and the minor diameter to pitch ratio for the thread of Example 3 is less than 55% that of similarly sized standard bone screws. With its unconventional decreased minor diameter and increased thread pitch, a thread according to Example 3 made of polyetheretherketone has been shown by the present inventors to be able to bend to follow the natural curve of the intramedullary canal of a human clavicle.

Examples of threads according to the invention preferably have a pitch greater than that for standard bone screws of a similar major diameter. For example, for threads with a major diameter less than 6.25 mm, it is preferable to have a pitch greater than 2.2 mm; more preferably greater than 2.5; more preferably greater than or equal to 2.75. For threads with a major diameter less than 4.0 mm, it is preferable to have a pitch greater than 1.5 mm; more preferably greater than 1.75; more preferably greater than 2.0; more preferably greater than 2.25; more preferably greater than or equal to 2.75.

Examples of threads according to the invention having a major diameter less than 4.0 mm preferably have a major diameter to minor diameter ratio greater than 1.7; more preferably greater than 1.8; more preferably greater than 1.9; more preferably greater than 2.0.

Examples of threads according to the invention preferably have a major diameter to pitch ratio less than 2; more preferably less than 1.75; more preferably less than 1.5; more preferably less than 1.4; more preferably less than 1.3. For threads having a major diameter less than 4.0 mm, the major diameter to pitch ratio is preferably less than 2.7; more preferably less than 2.5; more preferably less than 2.25.

Examples of threads according to the invention preferably have a minor diameter to pitch ratio less than 1.2; more preferably less than 1.0; more preferably less than 0.8; more preferably less than or equal to 0.75, more preferably less than 0.7.

Figures 26, 27, 28:
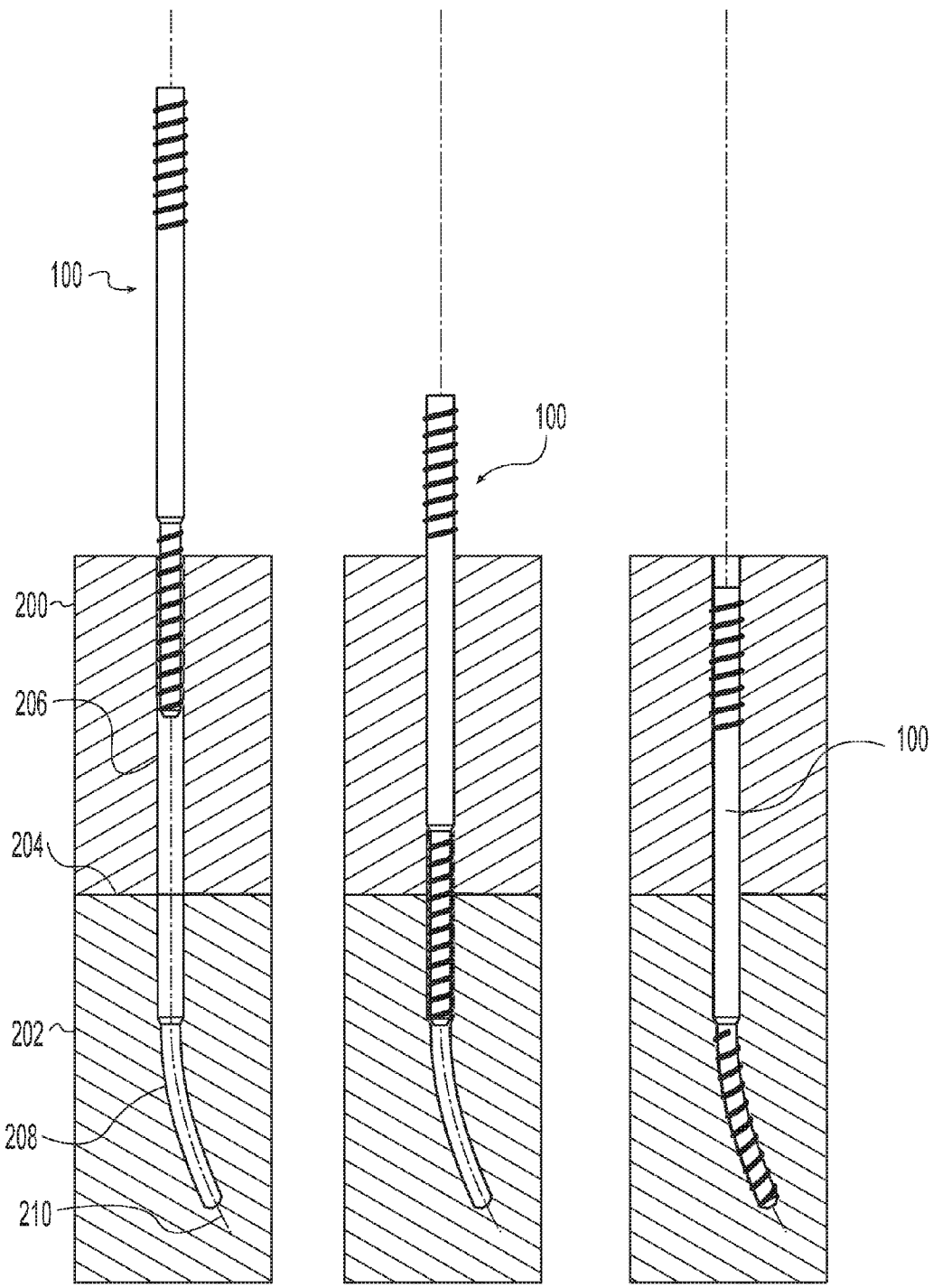
FIGS. 26-28 are partial sectional views showing the insertion of the screw of FIG. 1 into bone according to one example of the invention.

FIGS. 26-28 illustrate an implant being inserted into first and second bone portions 200, 202 having a bone interface 204 between them. The implant could be according to any of the preceding examples and the variations described herein. In the particular example of FIGS. 26-28, the example of FIG. 1 is shown. A first or proximal bore 206 is formed in the first bone portion 200, across the bone interface 204, and into the second bone portion 202. A second or distal bore 208 extends distally from the proximal bore 206 defining a curved path 210. The implant 100 is advanced through the proximal bore 206 until the distal threads engage the distal bore 208 as shown in FIG. 27. Further advancing the implant 100 causes it to bend to follow the curved path 210 as shown in FIG. 28. Having a straight portion of the path, and thus the straight mid portion of the implant 100, spanning the bone interface results in a zero stress and strain state at the bone interface which prevents separation of the bone portions 200, 202 at the interface 204.

FIGS. 29-34 depict an illustrative example of an inserter 1400 useable with the flexible implant 170 of FIGS. 8-13. The inserter 1400 is a modular design including an elongated, cannulated, coupling member 1402 having a proximal end 1404, a distal end 1406 and a longitudinal axis 1408 extending between the proximal and distal ends 1404, 1406. A hub 1410 coaxial with the longitudinal axis 1408 is formed intermediate the proximal and distal ends 1404, 1406. The hub includes a proximal facing shoulder 1412 and a distal facing shoulder 1414. A post 1416 extends proximally from the hub to the proximal end 1404 and includes a radial boss 1418 that tapers proximally and forms a shoulder 1420 distally. A shaft 1422 extends distally from the hub 1410 to the distal end 1406 and includes an engagement feature operable to engage the proximal end of an implant in torque transmitting relationship. For example, the engagement feature may include a pair of opposed tongues 1424 engageable with the opposed flats 187 of the implant 170. The hub 1410 includes a thread 1426 distal to the distal shoulder 1414. The hub includes an alignment mark in the form of an alignment notch 1428 oriented parallel to the longitudinal axis 1408. A flat 1429 is formed on the hub 1410. A cannulated draw bar 1480 is coaxially receivable in the coupling member 1402 with a hex head 1482 abutting the proximal end of the post 1416 and a distal end 1484 extending to the distal end of the shaft 1422. The distal end 1484 of the draw bar includes a thread 1486 engageable with the thread 189 in the passage 184 of the implant 170 to secure the implant 170 to the coupling member 1402.

A handle assembly 1430 is removably engageable with the proximal portion of the coupling member 1402. The handle assembly includes a cannulated handle 1432 and a cap 1434 threadably engageable with the handle 1432. The handle is shown in detail in FIGS. 30-34. The handle 1432 includes a cylindrical body 1436 having a "D"-shaped distal opening 1438. The flat side of the opening is engageable with the flat 1429 on the hub to align the handle in a predetermined orientation relative to the hub 1410 and the engagement feature of the shaft 1422. A boss 1440 protrudes from the distal end of the handle to engage a hole (not shown) formed in the proximal shoulder 1412 of the hub. A button 1442 is mounted in the handle 1432 for transverse translation between first and second positions. The button has an opening through it having an inner profile 1444 with a wider portion 1446 and a narrower portion 1448. The button is biased by a spring 1450 toward a first position in which the narrower portion 1448 is displaced toward the axis 1408 so that the inner profile 1444 is captured beneath the shoulder 1420 of the radial boss 1418 on the coupling member 1402 to retain the handle on the coupling member 1402. When the button is pressed inwardly to the second position, the wider portion 1446 is displaced toward the axis 1408 so that the wider portion 1446 provides clearance for the handle 1432 to be removed over the boss 1418. The proximal taper of the boss 1418 allows the handle to be pressed onto the coupling member 1402 without the need to depress the button. The taper of the boss 1418 engages the narrower portion 1448 of the button inner profile 1444 causing it to translate into the second position as the handle moves distally. Eventually, as the handle seats on the coupling member, the inner profile 1444 passes over the shoulder 1420 and the spring causes the button to snap back to the first, locked, position. An alignment mark in the form of an alignment notch 1452 near the distal end of the handle 1432 and oriented parallel to the longitudinal axis 1408 can be aligned with the similar alignment notch 1428 on the coupling member 1402 to provide a visual aid for initially aligning the handle and coupling member. The proximal end of the handle 1432 includes a thread 1454 engageable with the cap 1434. The cap prevents unintentional release of the flexible screw. In the illustrative example of FIG. 29, the cap covers the hex head 1482 and prevents unintentional rotation of the draw bar.

A cross pinning guide assembly 1458 is identical to the handle assembly 1430 with the addition of a cross pinning guide 1460 extending distally from the handle 1462. In the case of implants having one or more preformed transverse passages, the cross pinning guide 1460 includes guide holes 1464 having axes that align with the axes of the passages 181, 183 when the implant 170 and the cross pinning guide are coupled to the coupling member 1402. In the case of an implant such as the implant 100 of FIGS. 1-4 that does not have a preformed transverse passage, cross fixation may be inserted directly through the implant 100 forming a transverse passage intraoperatively.

A compression sleeve 1466 includes a proximal end 1468 threadably engageable with the thread 1426 of the hub 1410. The compression sleeve 1466 tapers distally and is coaxial with the shaft 1422. The enlarged proximal end of the compression sleeve 1466 supports a large thread capable of sustaining large axial loads while the narrowed distal end of the compression sleeve 1466 will fit through a narrow incision to abut bone adjacent an entry point for the implant into the bone. The threaded engagement of the compression sleeve 1466 with the hub 1410 translates rotation of the compression sleeve 1466 about the axis 1408 into axial translation of the sleeve relative to the shaft 1422. The compression sleeve 1466 may be a two-part assembly 1467 so that the bone contacting distal end remains stationary while the threaded portion is rotated. For example, the distal end could be shaped to conform to the bone surface while the proximal end rotates to drive the sleeve toward the bone. For example, a separate sleeve may have a chamfered tip 1469.

Figure 29:
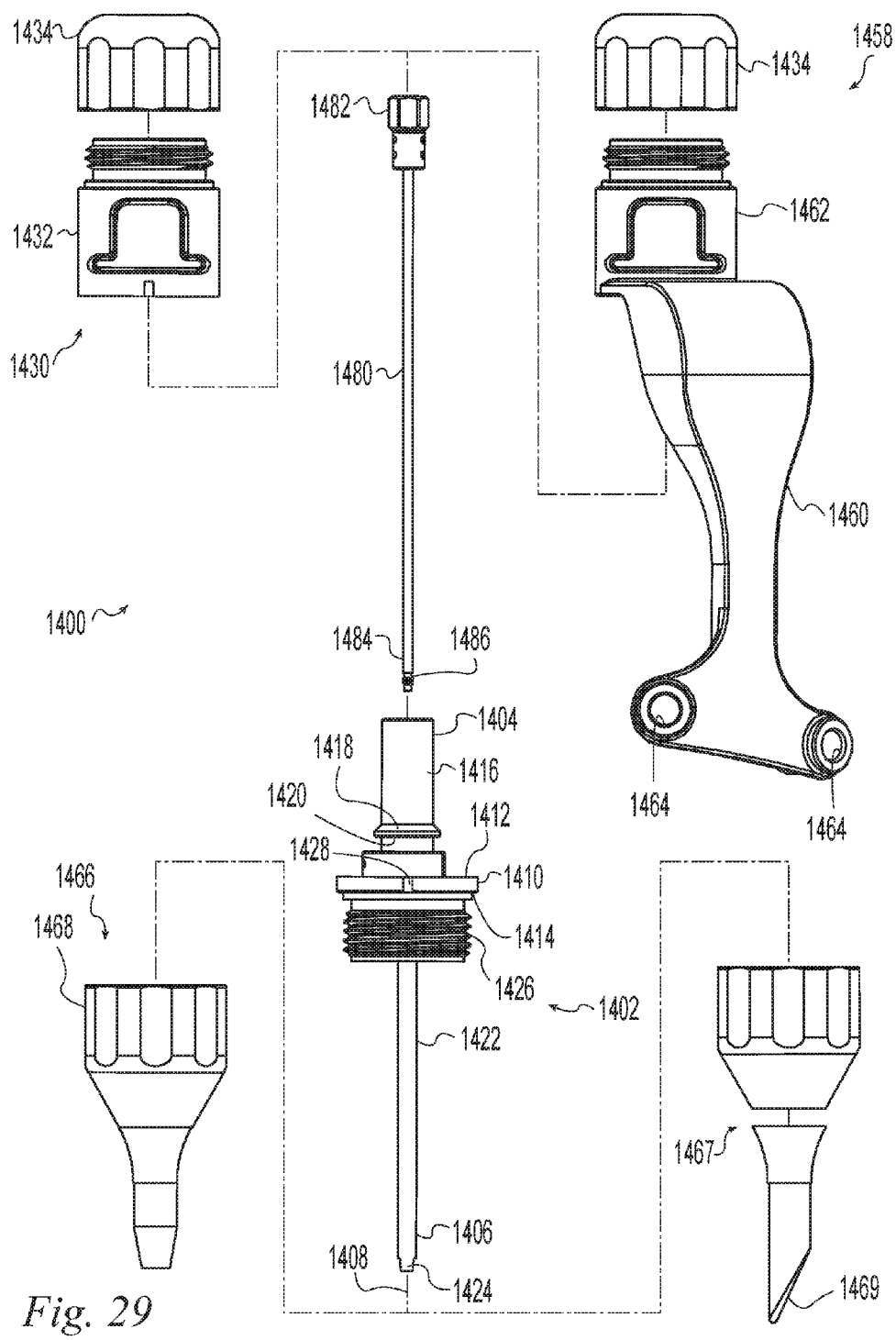
FIG. 29 is an exploded plan view of an example of an inserter instrument useable with the implants of FIGS. 1-28 according to one example of the invention.
Figure 30:
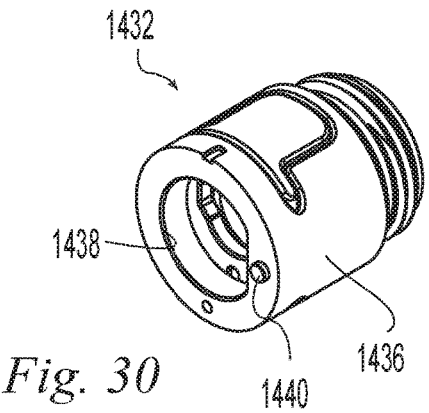
FIG. 30 is a perspective view of a handle of the inserter instrument of FIG. 29.
Figure 31:
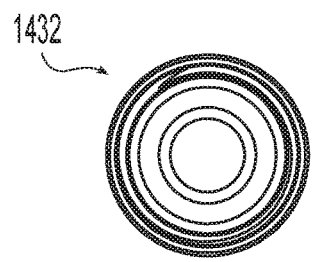
FIG. 31 is a top view of the handle of FIG. 30.
Figure 32:
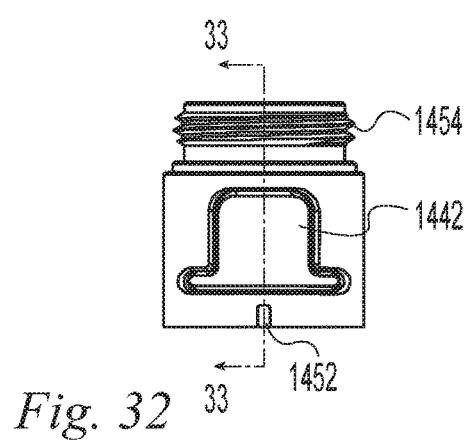
FIG. 32 is a front view of the handle of FIG. 30.
Figure 33:
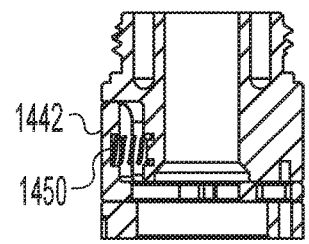
FIG. 33 is a cross sectional view of the handle of FIG. 30 taken along line 33-33 of FIG. 32.
Figure 34:
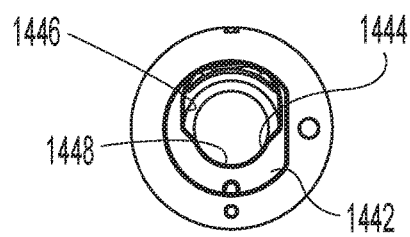
FIG. 34 is a bottom view of the handle of FIG. 30.
Figure 35:
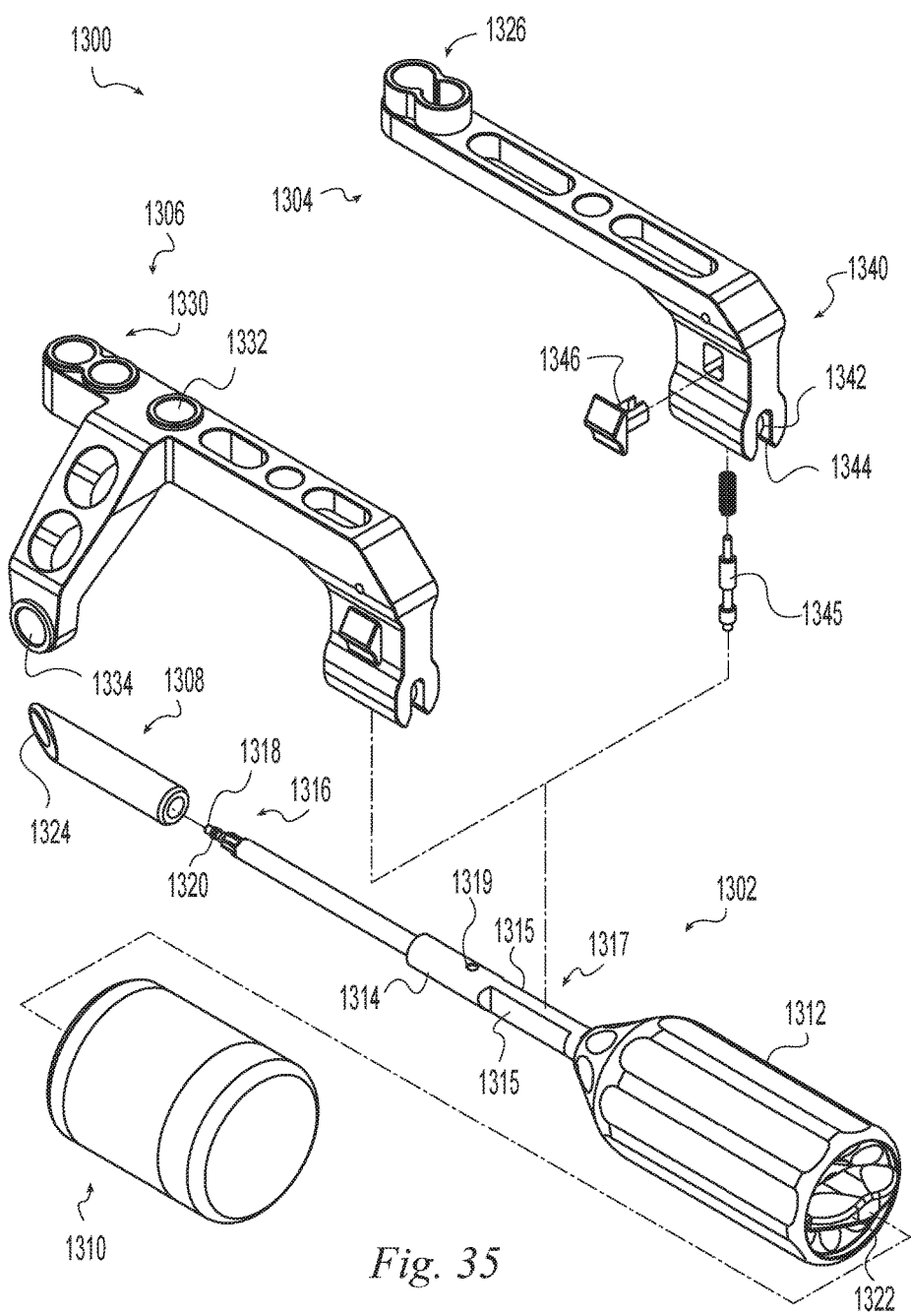
FIG. 35 is an exploded perspective view of an inserter instrument useable with the implants of FIGS. 1-28 according to one example of the invention.

FIG. 35 illustrates an alternative inserter assembly 1300 similar to that of FIG. 29. The assembly includes an inserter 1302, alternative cross pinning guides 1304, 1306, a compression sleeve 1308 and a cap 1310. The inserter includes a handle 1312, a shaft 1314, an implant engagement end 1316, and a drawbar 1318. The shaft has an implant engagement portion at its distal end for engaging a an implant to rotate the implant into a bone. The drawbar has a threaded tip 1320 and a knob 1322 for rotating the draw bar relative to the shaft to engage and disengage the threaded tip with an implant having a corresponding threaded hole. The shaft 1314 includes opposed flats 1315 forming a narrow portion 1317. A hole 1319 is formed in the shaft distal to the narrow portion.

The compression sleeve 1308 is engageable with the inserter shaft 1314 in rotating and axial sliding relationship. The distal end 1324 of the compression sleeve is chamfered to engage a bone surface. The compression sleeve 1308 may be provided in different lengths and tip geometries to fit differently shaped bone surfaces.

A first cross pinning guide 1304 includes a pair of guide holes 1326 that align with a corresponding pair of passages in an implant such as for example implant 270 of FIG. 14. A second, alternative cross pinning guide 1306 includes a pair of holes 1330, a third hole 1332 co-planar with the pair of holes 1330, and a fourth hole 1334 angularly offset from the others which holes correspond to passages in an implant such as for example implant 600 of FIG. 22. The cross pinning guides may be provided in any configuration corresponding to an implant in order to guide placement of cross pins or screws into passages of the implant. In the example of FIG. 35, the cross pinning guides include an inserter engaging portion 1340 with an axial passage 1342 and a slot 1344 communicating from the passage through a sidewall of the inserter engaging portion 1340. A spring loaded plunger 1345 is retained in an internal passage of the inserter engaging portion by a actuator 1346. The actuator may be moved by a user against spring pressure to move the plunger from a first position in which the plunger extends into the passage 1342 and a second, retracted position in which the plunger extends less or not at all into the passage 1342. In use, the cross pinning guide 1304 or 1306 is engaged with the inserter by sliding the inserter engaging portion 1340 over the narrow portion 1317 of the shaft so that the narrow portion passes through the slot 1344 and into the passage 1342. Pressing downwardly on the cross pinning guide will force the plunger 1345 to retract as it is pressed against the top of the shaft. Alternatively, the actuator 1346 may be moved by a user to retract the plunger to ease engagement. Once the cross pinning guide is engaged with the narrow portion of the shaft, it may be slid forward past the narrow portion to trap the cross pinning guide radially on the shaft. The plunger will snap into the hole 1319 in the shaft to lock the cross pinning guide axially and rotationally on the shaft. Once locked, the cross pinning guide and inserter are indexed with the guide holes in the cross pinning guide in known location relative to the inserter shaft and therefore relative to an implant attached to the inserter shaft. To remove the cross pinning guide from the inserter, the actuator 1346 may be moved to retract the plunger and then the cross pinning guide may be slid rearwardly to the narrow portion of the shaft at which point the cross pinning guide may be moved radially away from the shaft. The cap 1310 may optionally be used to cover the drawbar knob 1322 to allow striking the handle while preventing damage to or rotation of the knob 1322.

Figures 36, 37, 38:
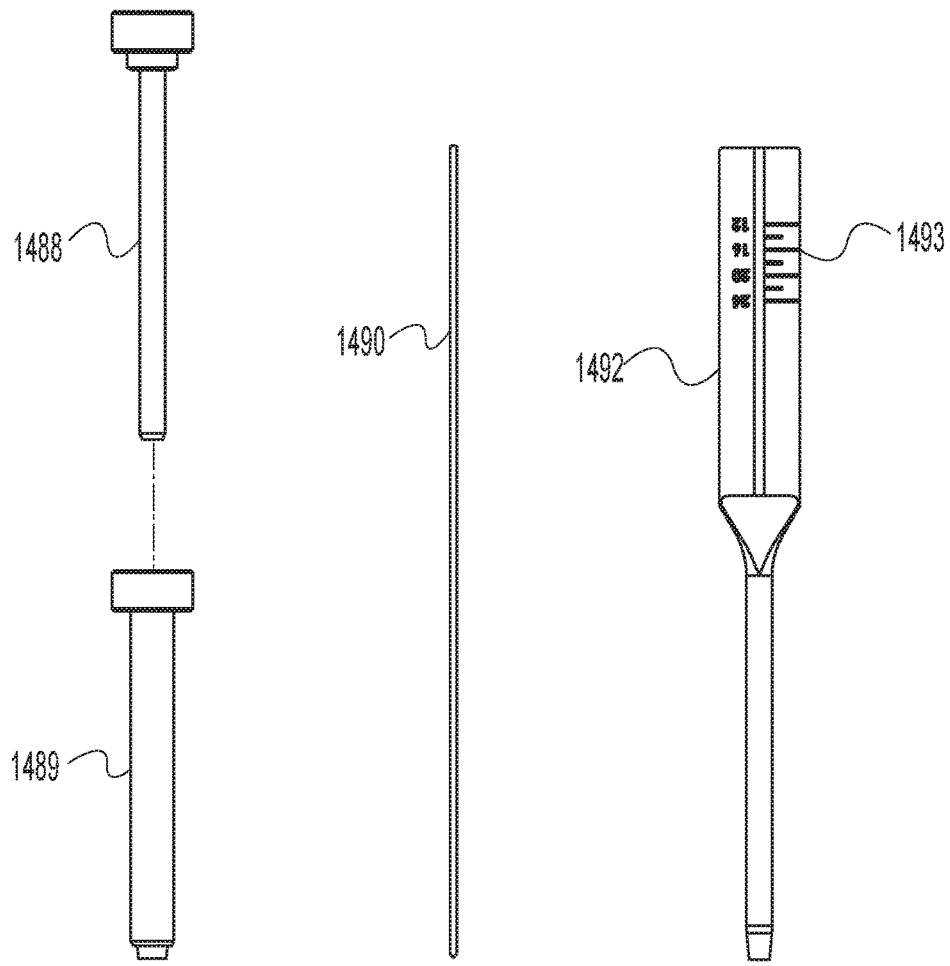
FIG. 36 is a front view of a pair of nesting sleeves useable with the inserter instruments of FIGS. 29 and 35 according to one example of the invention.
FIG. 37 is a front view of a drill wire useable in a method according to one example of the invention.
FIG. 38 is a front view of a depth gauge useable in a method according to one example of the invention.

FIG. 36 depicts a pair of nesting sleeves including an inner sleeve 1488 and an outer sleeve 1489. The inner sleeve 1488 includes a longitudinal passage sized to guide a drill wire, e.g. a K-wire having a diameter suitable for drilling a pilot hole for a self-tapping screw. The outer sleeve 1489 includes a longitudinal passage sized to pass a bone screw. The inner sleeve has an outer diameter that is a slip fit within the outer sleeve. The outer sleeve has an outer diameter that is a slip fit within the guide holes of the cross pinning guides 1460, 1304, or 1306.

FIG. 37 depicts a drill wire 1490 receivable in slip fit relationship within the inner sleeve 1488 and having a diameter suitable for drilling a pilot hole for a self-tapping screw.

FIG. 38 depicts a depth gauge 1492 having an inner passage sized to receive the drill wire 1490 in slip fit relationship and a scale 1493 that indicates the length of the drill wire 1490 that extends from the gauge 1492 distal end.

Figures 39, 40:
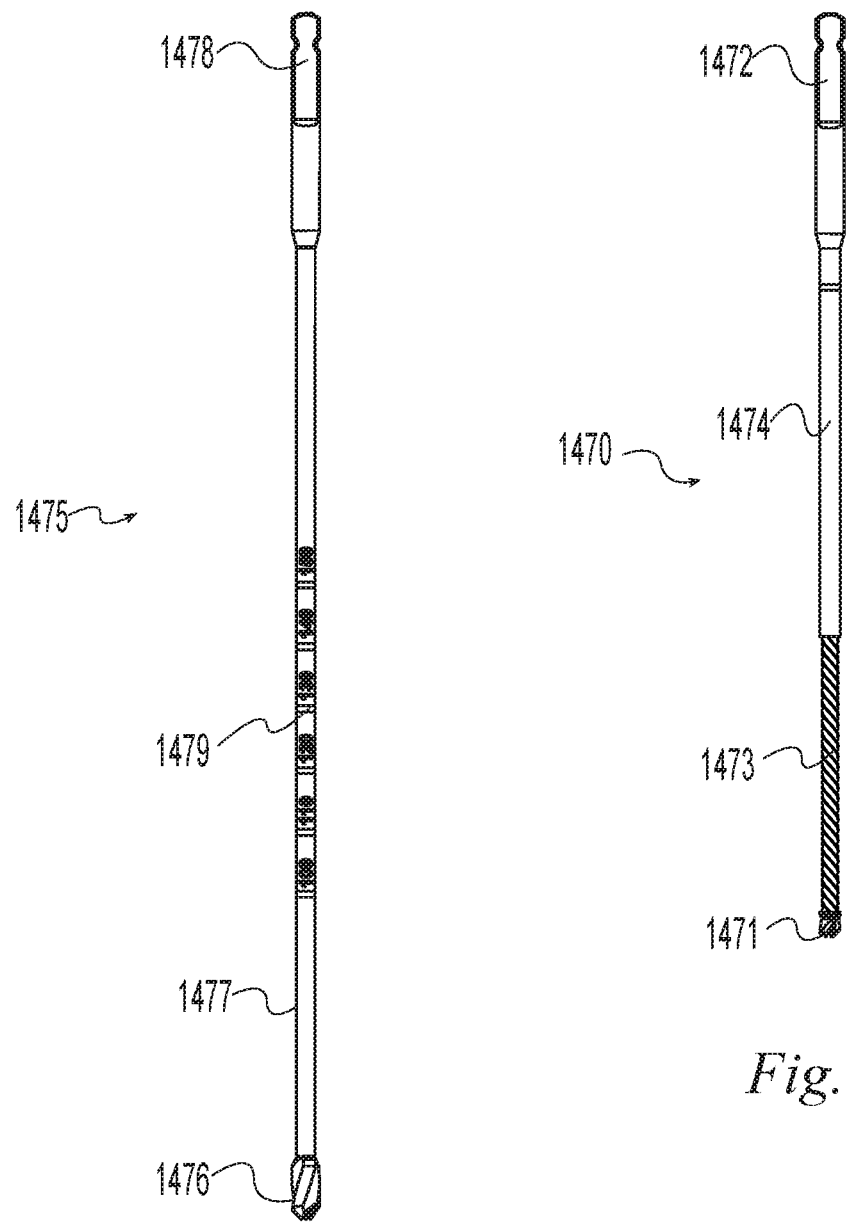
FIG. 39 is a front view of a rigid drill useable in a method according to one example of the invention.
FIG. 40 is a front view of a flexible drill useable in a method according to one example of the invention.

FIG. 39 depicts a cannulated rigid drill or reamer 1475 having a reaming head 1476 at a distal end a rigid shaft 1477 extending proximally from the reaming head 1476 to a proximal end 1478. Index marks 1479 on the shaft 1477 may be read adjacent an opening in a bone to indicate an appropriate length of implant for a particular reamed depth. In the illustrative example of FIG. 39, the index marks correspond to implants having variable length proximal portions and constant length distal portions. The reaming head 1476 preferably has a length of 10-30 mm so it can be viewed via fluoroscopy and used as a gauge for drilling a specified minimum distance across a fracture site. In the illustrative example of FIG. 39, the reaming head 1476 has a length of 15 mm to clearly indicate when a minimum depth of 15 mm past the fracture site has been reached. The reaming head 1476 has a diameter equal to or greater than the proximal portion of the flexible implant 100, 170. In the case of a set of screws as shown in the illustrative example of FIGS. 5-7 a corresponding set of rigid reamers is provided having reaming diameters equal to or slightly larger than the proximal diameters 148, 158, 168 of the screws 140, 150, 160.

FIG. 40 depicts a cannulated flexible drill or reamer 1470 having a reaming head 1471 at a distal end, a driver engagement portion at a proximal end 1472 and a flexible shaft 1473 intermediate the reaming head 1471 and proximal end 1472. In the illustrative example of FIG. 40, the flexible shaft 1473 is joined to the reaming head 1471 and extends proximally part way toward the proximal end 1472. A rigid shaft 1474 extends from the flexible shaft 1473 to the proximal end 1472. The flexible shaft 1473 may include a variety of flexible constructs as is known in the art such as, for example, twisted cables, helical cut tubes, interlocking tongue and groove segments, and other flexible constructs. In the illustrative example of FIG. 40, the flexible shaft 1473 includes a twisted cable construction with an inner cable twisted in a first direction and an outer cable twisted in an opposite direction to provide torque transmitting capability in both rotational directions. The reaming head 1471 has a diameter sized to form a pilot hole for a self-tapping screw or for a tap. The reaming head diameter is preferably equal to or slightly larger than the minor diameter of the screw thread 112, 194 of the implant 100, 170 or the minor diameter of the tap. A flexible reamer is provided for each minor diameter to be accommodated. In the case of a set of screws like the illustrative example of FIGS. 5-7 having a constant minor diameter across screw sizes, only a single flexible reamer is needed.

Figure 41:
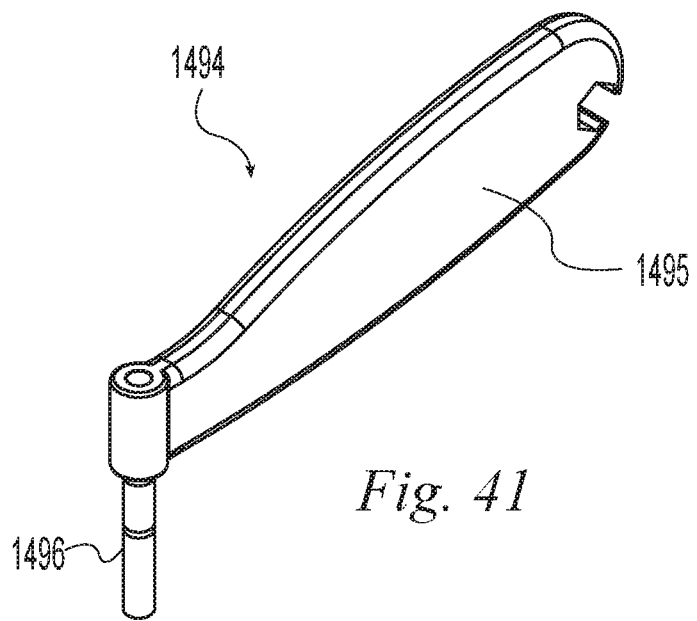
FIG. 41 is a perspective view of a centering guide useable in a method according to one example of the invention.
Figure 42:
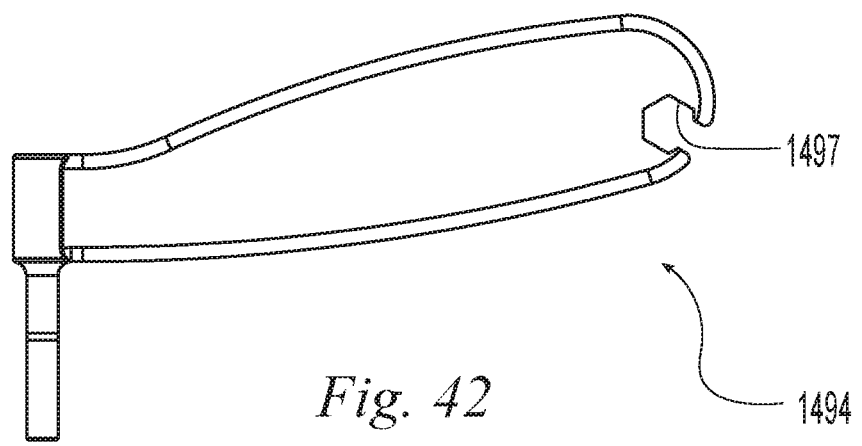
FIG. 42 is a front view of the centering guide of FIG. 41.
Figure 47:
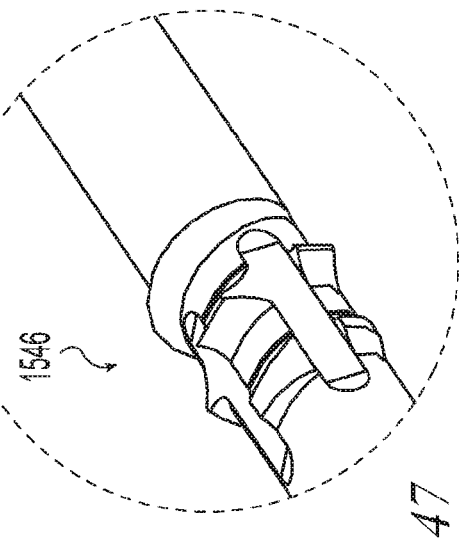
FIG. 47 is a detail view of an anchor feature of the flexible tap of FIG. 43.
Figure 46:
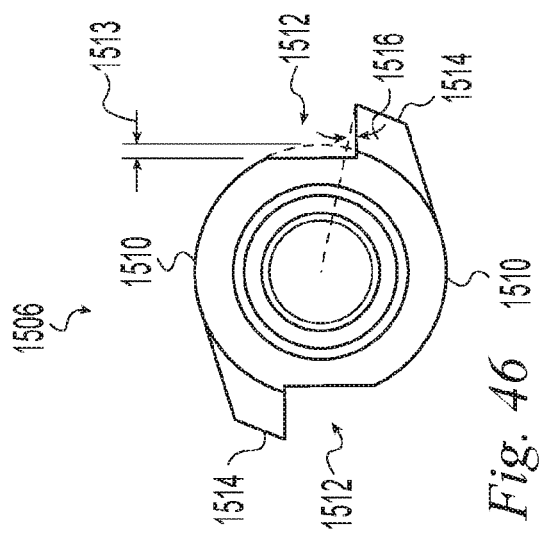
FIG. 46 is an end view of the tap head of FIG. 45.
Figure 45:
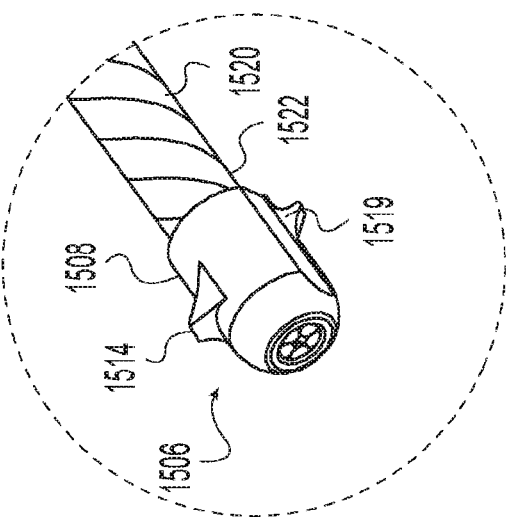
FIG. 45 is a detail view of a head of the flexible tap of FIG. 43.
Figure 48:
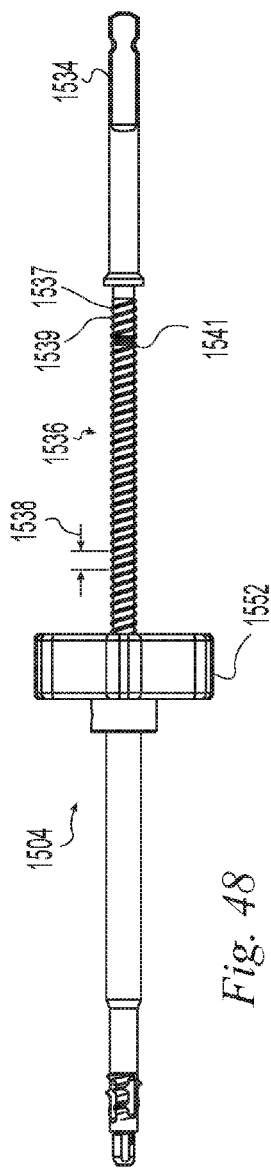
FIG. 48 is a plan view of the flexible tap of FIG. 43.

FIGS. 41 and 42 depict a centering guide 1494 having a handle 1495 and a cannulated end 1496 having an inner passage sized to receive the flexible reamer 1470 in slip fit relationship. The handle 1495, includes a wrench 1497 that may be used, for example, to engage another instrument to provide counter torque.

FIGS. 43-50 depict illustrative examples of a flexible tap 1500 according to the present invention. The tap 1500 is capable of forming a thread along a straight or curved path. For example, the tap 1500 is capable of forming a thread along a curved path in a bone to receive a threaded component. In the illustrative example of FIGS. 43-50, the tap is sized to form a thread to receive one of the flexible implants of the illustrative examples of FIG. 1, 8, 12, 16, 18, or 22. Where multiple sizes of screw thread are provided, a set of multiple taps of corresponding thread sizes may be provided. The tap may serve as a trial implant and provides tactile feedback regarding the fit of the implant in the bone. If it is determined that a larger screw is desirable, subsequent larger rigid reamers may be used to re-drill the lateral straight portion and subsequent larger flexible taps may be used to increase the distal thread major diameter without having to re-ream the medial curved portion of the bone hole.

The tap 1500 includes a first member 1502 and a second member 1504 engaged with the first member 1502. The first member 1502 can be rotationally driven relative to the second member so that the first member advances a predetermined amount with each full rotation of the first member 1502. The first member includes a thread forming portion that forms a thread in a bone as it is advanced relative to the second member. At least a portion of the first member 1502 is flexible so that the cutting portion can follow a curved path in the bone.

In the illustrative example of FIGS. 43-50, the first member 1502 includes a tap head 1506 having a generally cylindrical body 1508. The body 1508 includes a pair of opposing lands 1510 and intervening flutes 1512 having a flute depth 1513. A screw thread segment projects from each land 1510 to form a tooth 1514 having a tooth face 1519. The tooth 1514 is adapted to form a thread in bone. The tooth 1514 may deform or cut the bone to form the thread. In the illustrative example of FIGS. 43-50, the tooth 1514 is adapted to cut a thread in a bone. The face 1519 is angled away from a radial reference line toward the center of the tap head to create a positive rake angle 1516. The face 1519 projects a desired thread profile for that tooth to form into the bone. The tap head 1506 may have a single tooth operable to single point cut a spiral thread in the bone as the tap head is rotated. Alternatively, the tap head 1506 can have a two or more teeth such as shown in the illustrative example of FIGS. 43-50. However, the tap head 1506 is intended to be able to follow a curved path in a bone. As the tap head 1506 follows a curved path to form a thread about the path axis, the pitch of the thread so formed will vary from a minimum on the inside of the curve to a maximum on the outside of the curve. With an increasing number of teeth 1514, and especially as the number of thread segments along the length of the tap head 1506 is increased, the tap head 1506 becomes more constrained. Driving a tap head with a large number of teeth along a curved path will result in damage to the formed bone thread due to e.g. the trailing teeth interfering with the bone thread as the leading teeth cause the tap head to tilt to follow the curved path. A single tooth provides the least constraint and the greatest ease in following a curved path. Two teeth, as in the illustrative example of FIGS. 43-50, may help balance the loads on the tap head while still allowing sufficient maneuverability to produce a well formed thread. Also, with two teeth, the leading tooth may project a shorter distance 1518 from the land 1510 so that a portion of the thread depth is removed by the first tooth and another portion is removed by the second tooth to reduce the torque required to drive the tap. When used to tap a pre-drilled hole, the land, or lands, fit within the hole and guide the tap head 1506 along the hole while the teeth 1514 cut the thread into the bone.

In the illustrative example of FIGS. 43-50, the first member 1502 further includes an elongated flexible shaft 1520 having a first end 1522 connected to the tap head 1506 and a second end 1524 opposite the first end. The flexible shaft 1520 may include a variety of flexible constructs as is known in the art such as, for example, twisted cables, helical cut tubes, interlocking tongue and groove segments, and other flexible constructs. In the illustrative example of FIGS. 43-50, the flexible shaft 1520 includes a twisted cable construction with an inner cable twisted in a first direction and an outer cable twisted in an opposite direction to provide torque transmitting capability in both rotational directions.

In the illustrative example of FIGS. 43-50, the first member further includes a driving shaft 1530 having a first end 1532 connected to the second end 1524 of the flexible shaft and a second end 1534 opposite the first end 1532. The driving shaft 1530 includes a helical thread 1536 having a thread pitch 1538. In the illustrative example of FIGS. 43-50, the thread 1536 is a multi-lead thread so there are two separate thread flights 1537, 1539 intertwined along the driving shaft 1530 and the thread pitch 1538 of each thread flight is measured as shown at reference numeral 1538. The thread pitch 1538 is the distance the driving shaft 1530 will translate along its axis for each complete revolution of the driving shaft 1530. Where the tap head 1506 includes multiple teeth 1514, the teeth are spaced longitudinally a distance corresponding to the driving shaft thread pitch 1538. Preferably the driving shaft is rigid. Also preferably, the second end 1534 includes an engagement portion releasably engageable with a driver. A driver may be a handle to provide a grip for manually turning by a user or a driver may be a rotary mechanism such as a powered drill.

In the illustrative example of FIGS. 43-50, the second member 1504 is threadably engaged with the thread 1536 of the driving shaft 1530 such that rotating the driving shaft 1530 relative to the second member 1504 translates the driving shaft 1530 and consequently the flexible shaft 1520 and tap head 1506 a distance equal to the thread pitch 1538 with each revolution of the drive shaft 1530. The tap head 1506 will form a thread in a bone with a pitch equal to the driving shaft thread pitch 1538. Changing the driving shaft thread pitch 1538 will change the formed bone thread pitch to a corresponding value. In the illustrative example of FIGS. 43-50, the second member 1504 is an anchor member able to be anchored to a bone and includes a hollow shaft 1540 having a first end 1542 and a second end 1544 opposite the first end. The first end 1542 defines a bone engagement portion having an anchor feature that grips the bone to secure the second member 1504 against axial translation relative to the bone as the drive shaft 1530 is rotated and the bone is threaded. In other words the anchor feature provides a counterforce to allow the threaded engagement between the first and second members to drive the tap head 1506 into the bone. The anchor feature may include barbs, threads, pins, screws, expandable members and other suitable features for securing a member to a bone. In the illustrative example of FIGS. 43-50, the anchor feature includes a self-tapping thread 1546 formed on the first end 1542 of the shaft 1540. The second end 1544 of the shaft is joined to a hub 1548 having a threaded passage 1550 (FIG. 49) engaged with the thread 1536 of the driving shaft 1530. A knob 1552 is mounted to the hub 1548 to facilitated engaging the self-tapping thread 1546 with a bone.

Alternatively, as shown in FIG. 44, a driver engagement 1553 may be substituted for the knob 1552 to permit engagement with a powered driver or modular handle. For example, a quick release handle may be engaged with the engagement 1553 to turn the self-tapping thread 1546 into a bone and then removed. Preferably, such a handle will cover the end 1534 of the first member to prevent accidental driving of the driving shaft 1530 when the self-tapping thread 1546 is turned into a bone. In addition, a wrench may be engaged with the driver engagement 1553 to provide counter torque when the driving shaft is driven. For example, the wrench 1497 of the centering guide 1494 may be used to provide a counter torque on the second member when the driving shaft 1530 of the first member is rotated relative to the second member.

Figure 49:
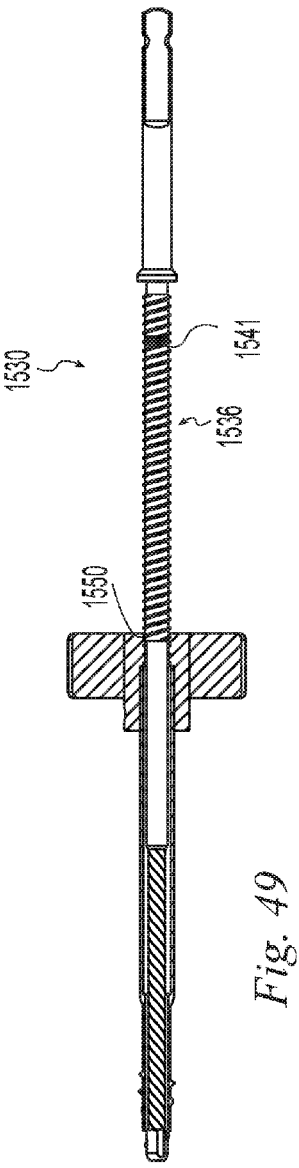
FIGS. 49 and 50 are partial sectional views of the flexible tap of FIG. 43 illustrating relative motion of components of the tap.
Figure 50:
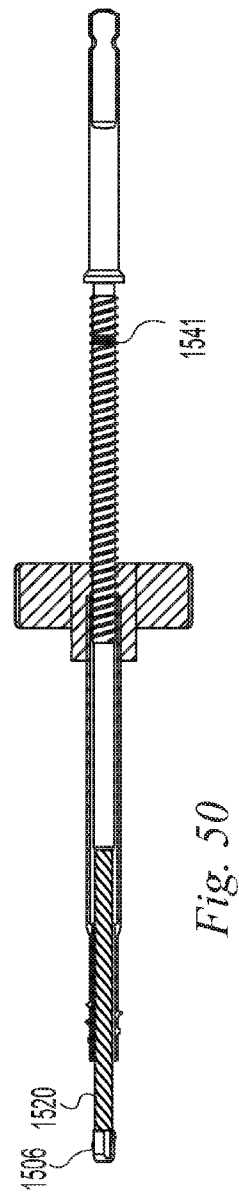

FIGS. 49 and 50 are partial sectional views depicting the second member 1504 in cross section and the first member 1502 in orthographic projection to show the interaction between the two. As seen in FIG. 49, the thread 1536 is engaged with the passage 1550. In FIG. 50, the driving shaft 1530 has been rotated four revolutions to advance the driving shaft 1530, flexible shaft 1520, and tap head 1506 four pitch lengths relative to the second member 1504. An index mark 1541, or shoulder or other feature, is provided on the driving shaft 1530 to indicate when the tap head has been driven to a depth sufficient to receive the distal end of the flexible implant. When the mark 1541 is aligned with the back edge of the knob 1552, the tap head has been driven to a sufficient depth.

FIGS. 51 and 52 depict an illustrative example of a method of forming a thread in a bone 1560 using the tap 1500 of FIGS. 43-50. A path for the tap 1500 is defined in the bone 1560. The path may be defined by a natural bone feature such as an intramedullary canal. The path may be defined by introducing a guide wire in the bone and the tap 1500 may be cannulated to follow the guide wire. The path may be defined by forming a hole 1562 in the bone 1560 as shown in the illustrative example of FIGS. 51 and 52. The path may be straight or curved and the tap 1500 may be used for tapping straight or curved holes. However, the tap 1500 is particularly useful for forming a thread in curved holes that traditional rigid taps are incapable of tapping. In the illustrative example of FIGS. 51 and 52, the hole is curved such as might be produced by flexibly reaming an intramedullary canal of a bone such as a clavicle, rib, fibular, radius, metatarsal, metacarpal or other bone.

In FIG. 51, the tap is engaged with the hole 1562 by turning the anchor feature of the second member 1504 into the hole 1562.

In FIG. 52, the driving shaft 1530 has been rotated several revolutions to advance the tap head 1506 into the bone hole to form a thread in the bone having a pitch equal to the driving shaft thread pitch 1538. While the driving shaft 1530 is preferably rigid and advances linearly relative to the second member 1504, the flexible shaft 1520 bends so that the tap head 1506 may follow any curvature in the path defined in the bone.

FIGS. 53-72 depict an illustrative method of using the implant 170 of FIG. 8 and the instruments of FIGS. 29-34 and FIGS. 36-50 to fix a fractured clavicle 1600. The patient is positioned for ready access to the surgical site. For example, the patient may be placed in a supine or beach chair position. A C-arm is positioned to enable anterior-posterior (AP) and cephalic views of the operative site. A 2-3 cm incision is made at the fracture site, e.g. along Langer's Lines, running perpendicular to the long axis of the clavicle to expose the fracture site. The platysma muscle is freed from the skin and split between its fibers. The middle branch of the supraclavicular nerve is identified and retracted.

Figure 53:
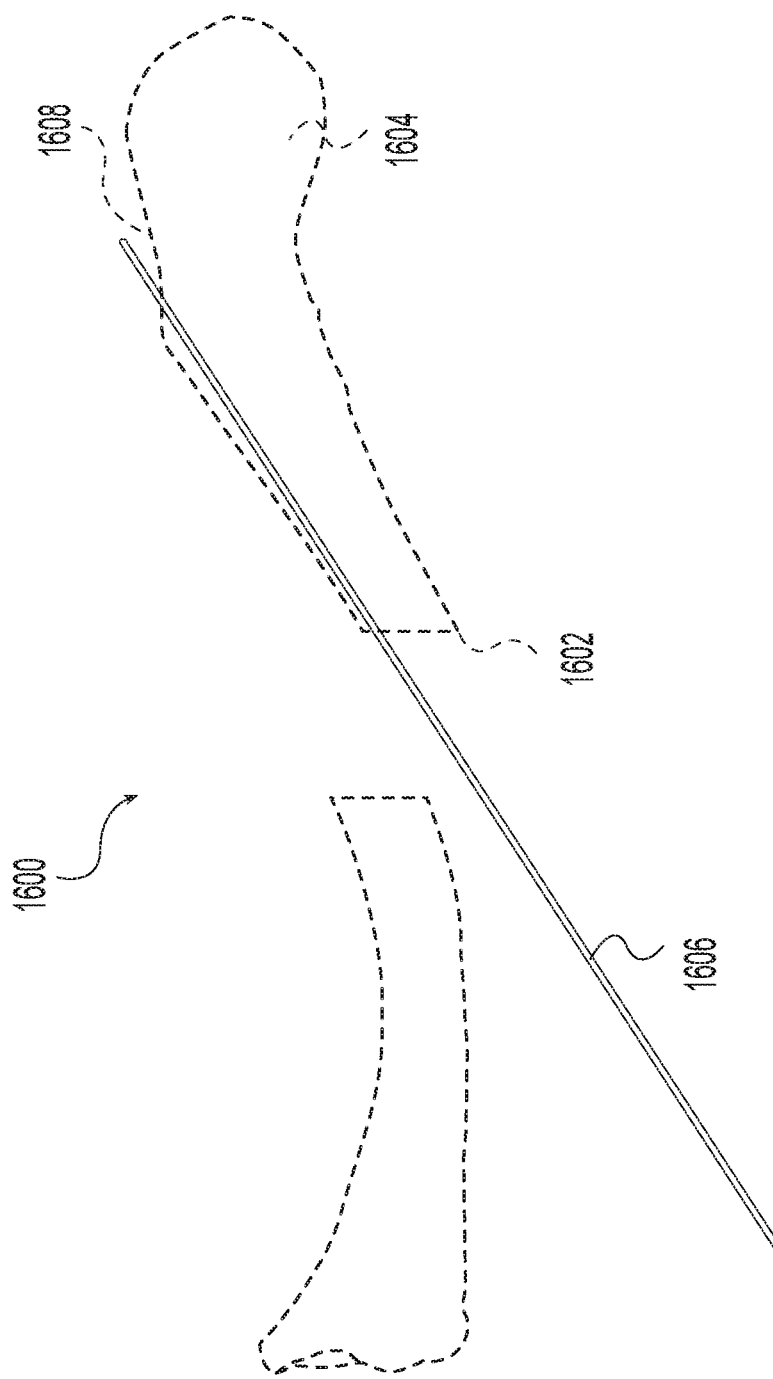
FIGS. 53-72 are plan views illustrating a method of using the implants and instruments of FIGS. 1-52 to fixate a fractured clavicle according to one example of the invention.

Referring to FIG. 53, the medial end 1602 of the lateral fragment 1604 of the fractured clavicle is elevated from the fracture site incision. A K-wire 1606 (or pin or drill) is drilled into the medial end of the lateral fragment 1604 and advanced through the dorsolateral cortex 1608 and out through the skin. Preferably, the K-wire is placed as far posteriorly in the lateral fragment 1604 as is possible to facilitate later steps in the procedure.

Figure 54:
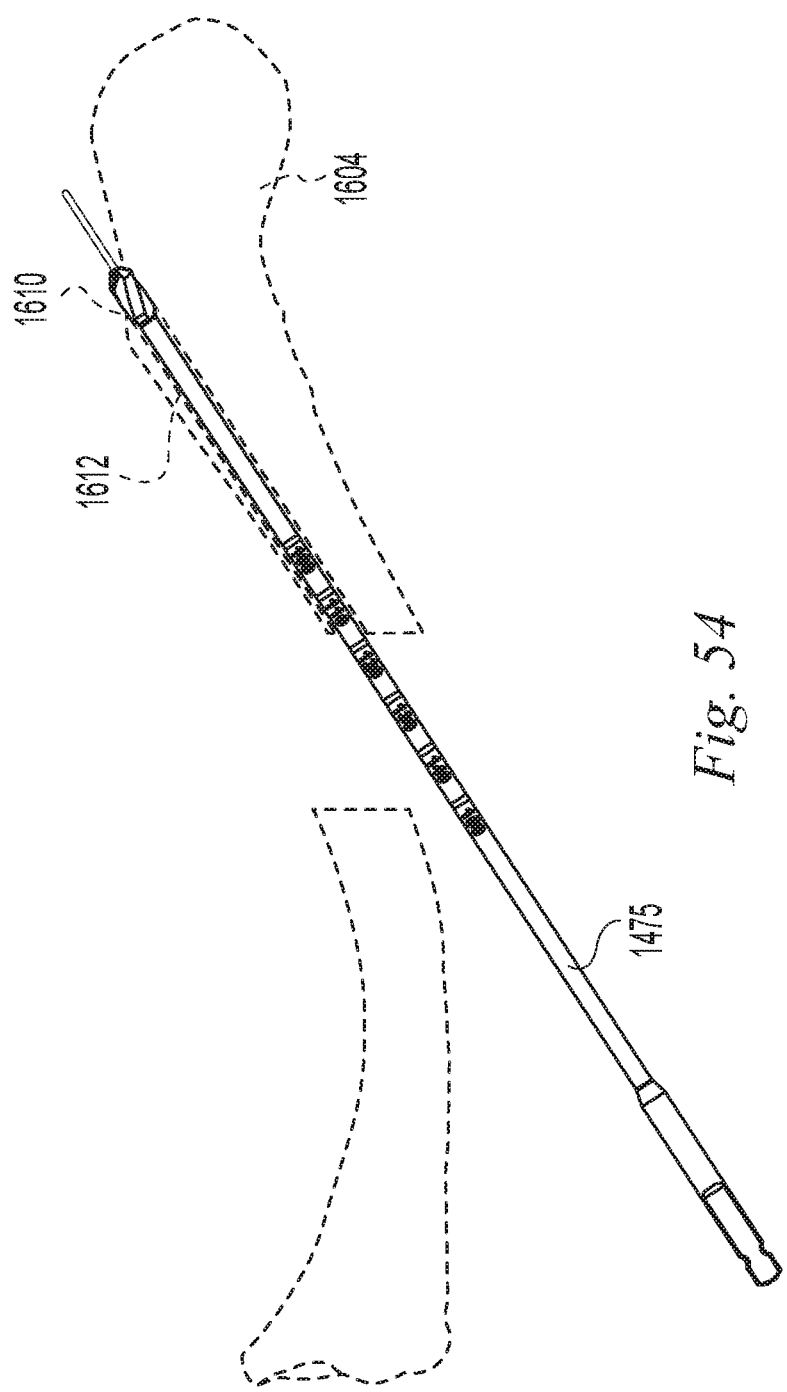

Referring to FIG. 54, the rigid reamer 1475 is connected to a driver (not shown) and guided over the K-wire to ream the lateral fragment 1604 from medial to lateral. The rigid reamer 1475 is replaced with a larger rigid reamer, if necessary, and sequential reaming is carried out until a desirable engagement is achieved, e.g. cortical engagement. The rigid reamer extends through the lateral cortical wall of the lateral fragment to create a lateral opening 1610 into the reamed bone tunnel 1612. The markings on the reamer shaft may be configured to indicate an appropriate implant length to reach the fracture. In such case, the length is noted. Alternatively, the reference numbers may be configured so that the measurement is taken during lateral-to-medial drilling as shown in FIG. 55.

Figure 55:
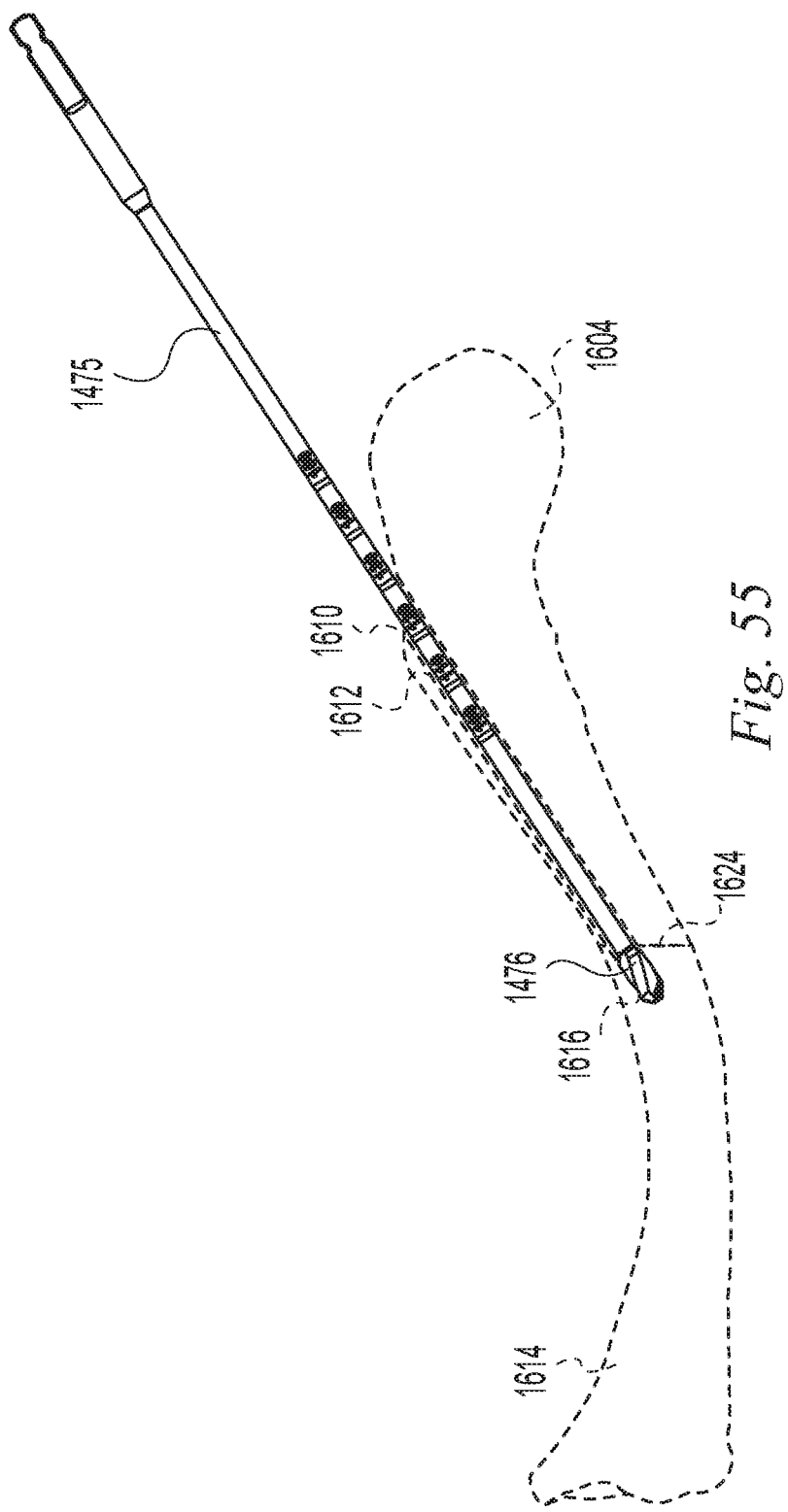

Referring to FIG. 55, the rigid reamer 1475 is removed from the lateral fragment 1604 and reversed so that it can be directed from lateral to medial through the bone tunnel 1612. To facilitate location of the opening 1610, the reamer may be passed retrograde, medial to lateral, through the tunnel 1612 and through the skin and then reconnected to the driver. Alternatively, the rigid reamer 1475 may be passed laterally to medially into the tunnel 1612. Alternatively, a guide wire may be placed to guide the reamer. For example, after the previous step, shown in FIG. 54, a guidewire may be advanced through the tunnel in the lateral fragment as the reamer is removed. The fracture may be reduced and the guide wire advanced into the medial fragment. The reamer may then be engaged with the guide wire for lateral-to-medial reaming.

With the rigid reamer 1475 in the tunnel 1612 and the fracture reduced so that the lateral fragment 1604 and medial fragment 1614 are abutting, the rigid reamer is advanced across the fracture 1624 and into the medial fragment 1614 creating an initial medial bone tunnel 1616. Preferably the reamer is advanced a sufficient distance to ensure that a non-threaded portion of the implant 100, 170 proximal to the distal thread 112, 194 will be positioned across the fracture since the non-threaded portion is more fatigue resistant than the threaded portion. Preferably the reamer is advanced a minimum of 15 mm into the medial fragment. In the illustrative example of FIGS. 53-72, the reaming head 1476 of the rigid reamer 1475 is 15 mm long and serves as a visual cue of the reamer depth when viewed radiographically. At this point the reference marks 1479 on the reamer may be read to indicate the appropriate size of flexible screw. Alternatively, the reference marks may be configured so that the measurement is taken during medial-to-lateral reaming of the lateral fragment as shown in FIG. 54.

Figure 56:
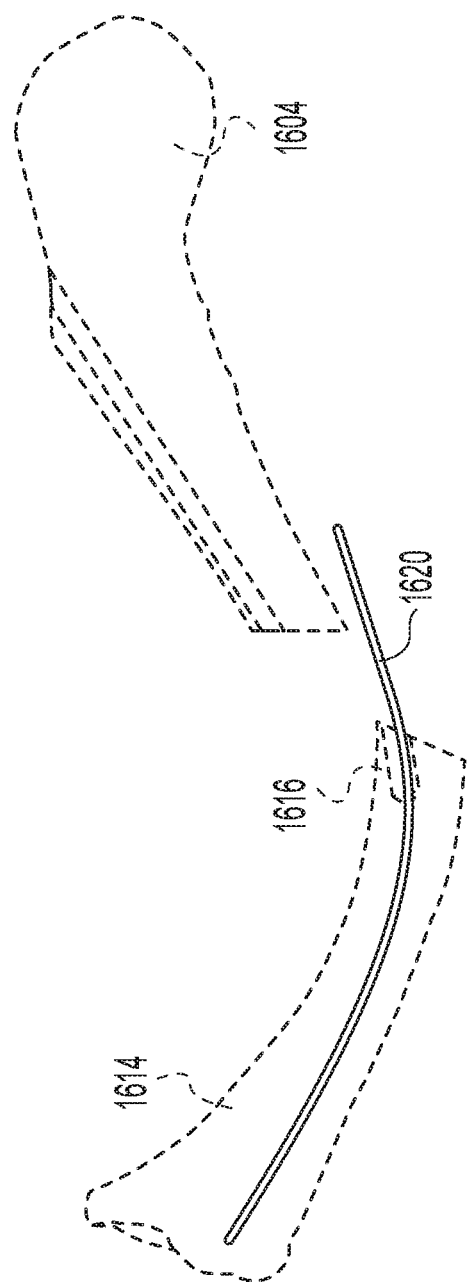

Referring to FIG. 56, the medial and lateral fragments 1614, 1604 are displaced and a flexible guide wire 1620 is inserted into the initial medial tunnel 1616 and further into the medial fragment 1614 to define a path. Optionally, a centering guide like the centering guide 1494 but sized for the flexible guide wire may be used to center the guide wire 1620 in the initial medial tunnel 1616. Once started, the guide wire 1620 will tend to follow the cortical wall of the bone. Since the clavicle has a curved shaft, the guide wire 1620 will form a curved path.

Figure 57:
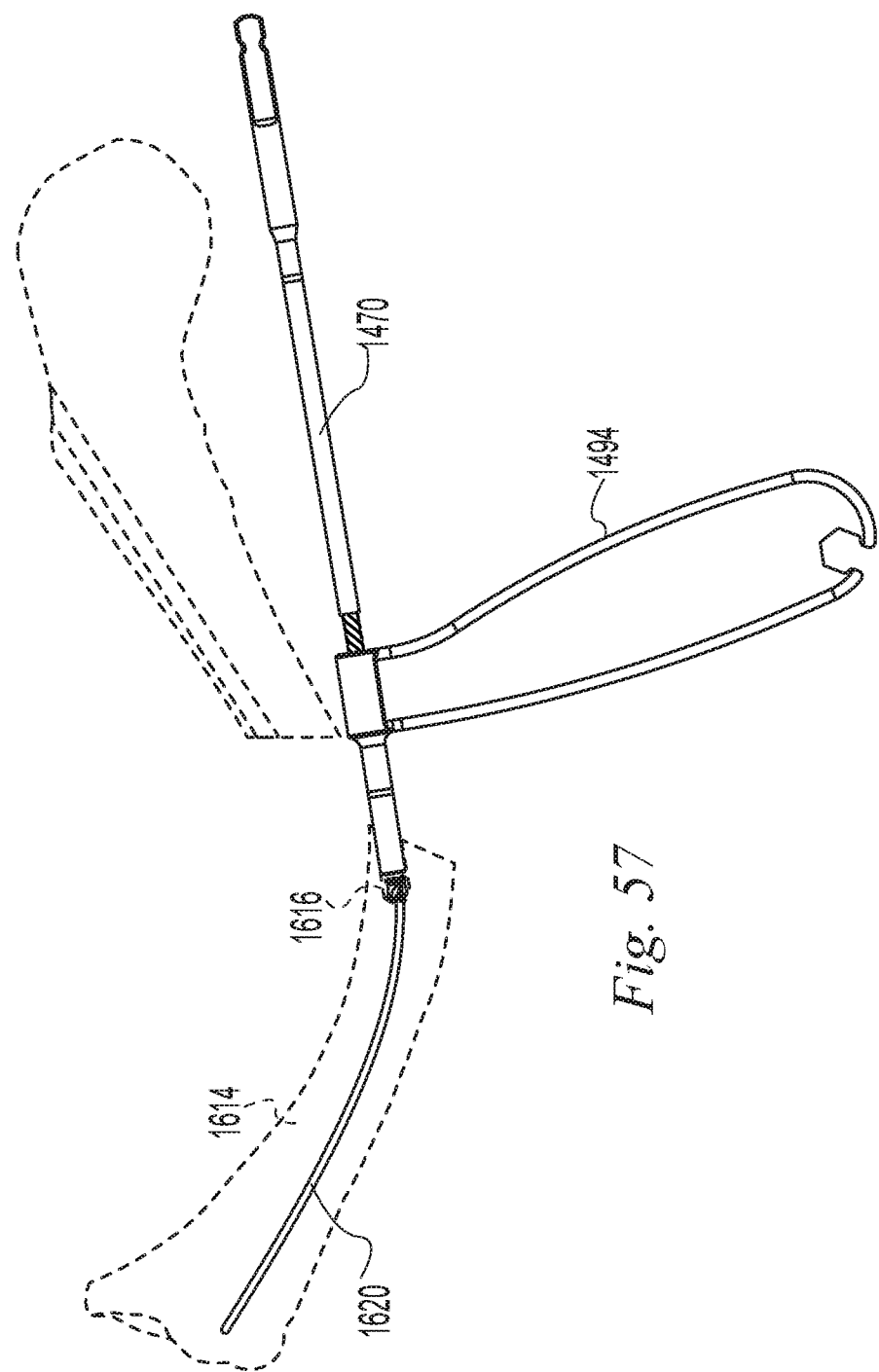

Referring to FIG. 57, the centering guide 1494 is inserted into the initial medial tunnel 1616 and the flexible reamer 1470 is inserted over the guide wire 1620, through the centering guide 1494 and into contact with the medial fragment 1614. The centering guide 1494 is optional but helps to center the reaming head 1471 of the flexible reamer 1470 in the initial medial tunnel 1616.

Figure 58:
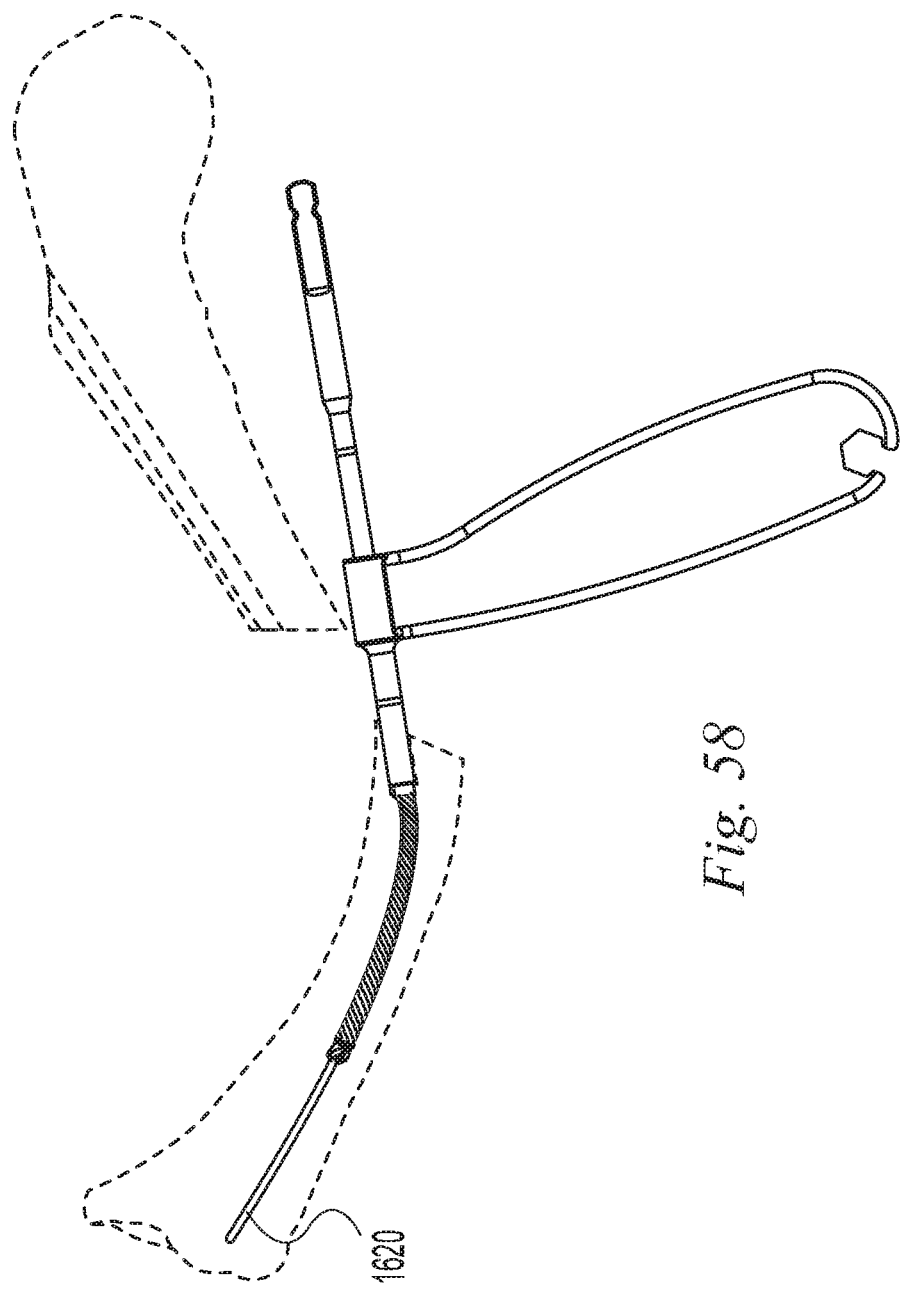

Referring to FIG. 58, the flexible reamer 1470 has been advanced over the guide wire 1620 to form a medial fragment bone tunnel. For example, a powered driver may be connected to the flexible reamer to drive it into the medial fragment.

Figure 59:
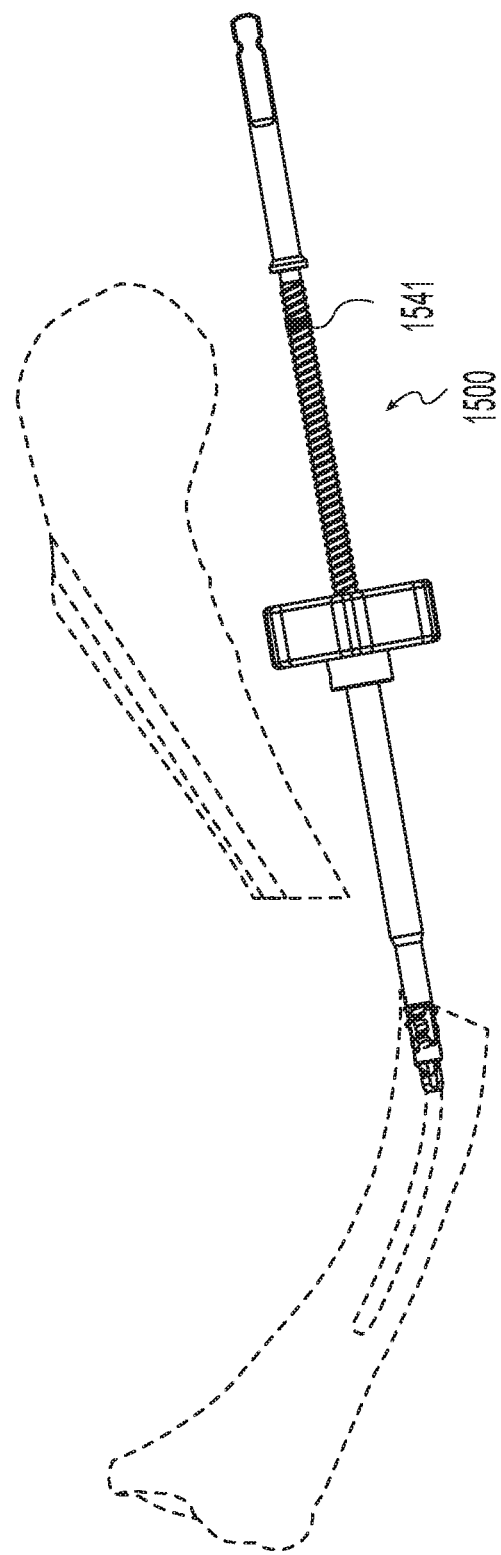

Referring to FIG. 59, the flexible reamer 1470, guidewire 1620 and centering guide 1494 have been removed and the flexible tap 1500 is engaged with the initial medial tunnel.

Figure 60:
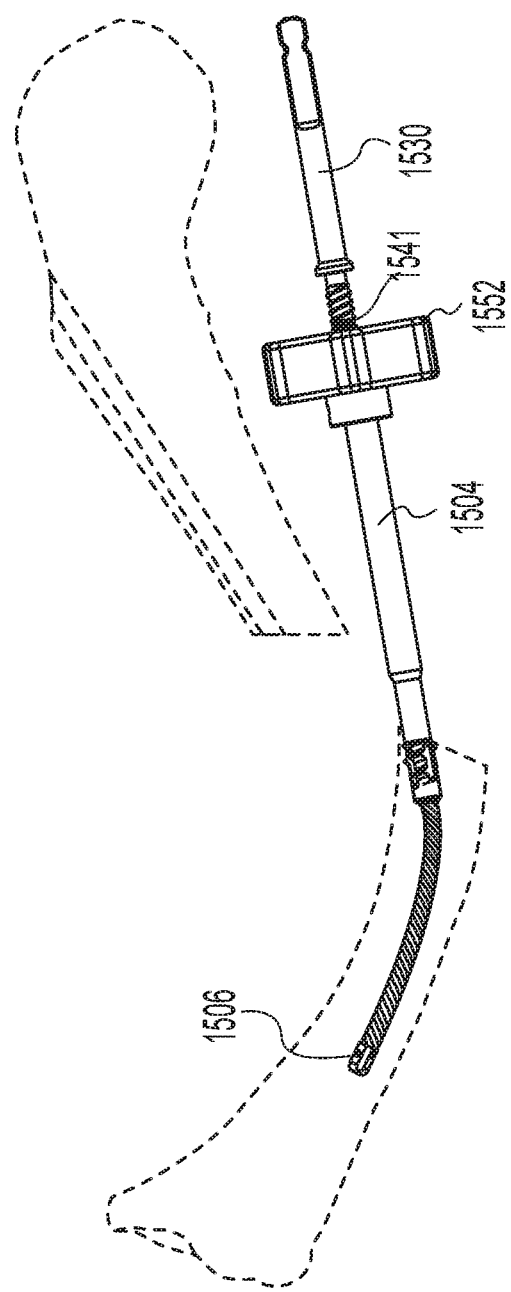

Referring to FIG. 60, the tap head 1506 has been advanced by rotating the drive shaft 1530 relative to the second member 1504 to form a helical thread in the medial fragment bone tunnel, for example by attaching a handle to the driving shaft and rotating the handle and shaft together. If necessary, the knob 1552 may be used to apply counter torque as the driving shaft 1530 is rotated. The tap may serve as a trial implant and provides tactile feedback regarding the fit of the implant in the bone. If it is determined that a larger screw is desirable, a subsequent larger rigid reamer may be used to re-drill the lateral straight portion and a subsequent larger flexible tap may be used to increase the distal thread major diameter without having to re-ream the medial curved portion of the bone hole. The tap head 1506 is advanced until the index mark 1541 is aligned with the back side of the knob 1552. If an implant with a proximal threaded portion is used, such as implant 100 of FIGS. 1-4, a lateral tap may be used to tap the lateral bone fragment to receive the proximal thread.

Figure 61:
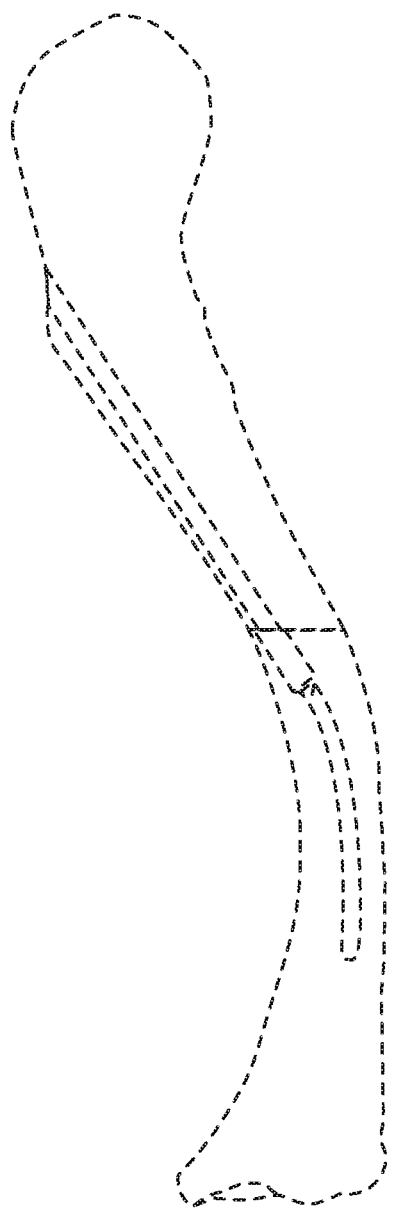

Referring to FIG. 61, the tap 1500 has been removed and the fracture reduced so that the lateral fragment 1604 and medial fragment 1614 are abutting.

Figure 62:
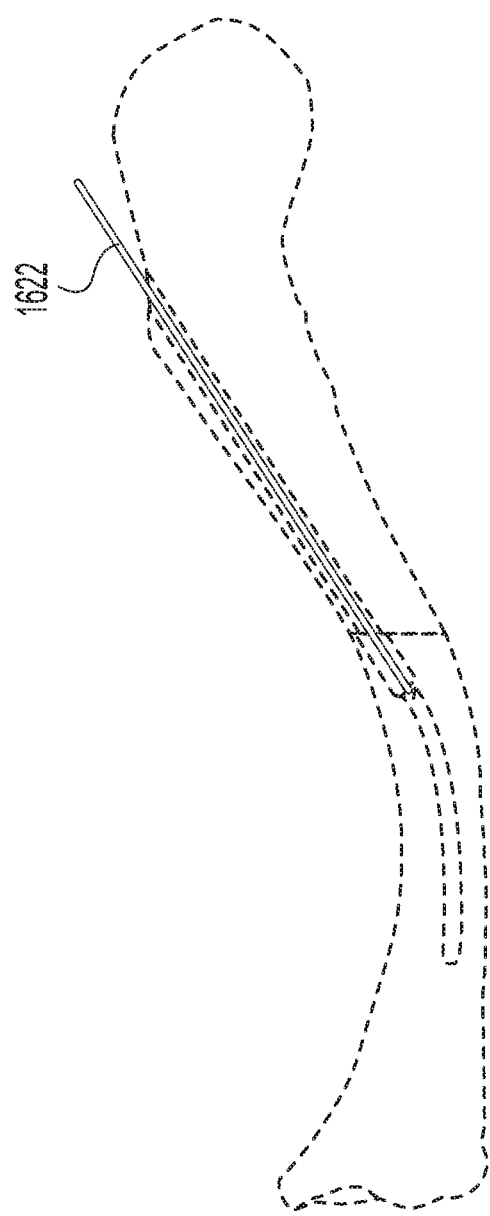

Referring to FIG. 62, an optional guide wire 1622 has been inserted lateral to medial through the lateral bone tunnel 1612 and across the fracture to aid in guiding the implant 170 across the fracture. No guidewire would be used for an implant that is not cannulated. In this example, the cannulated implant 170 of FIG. 8 will be used with a guide wire.

Figure 63:
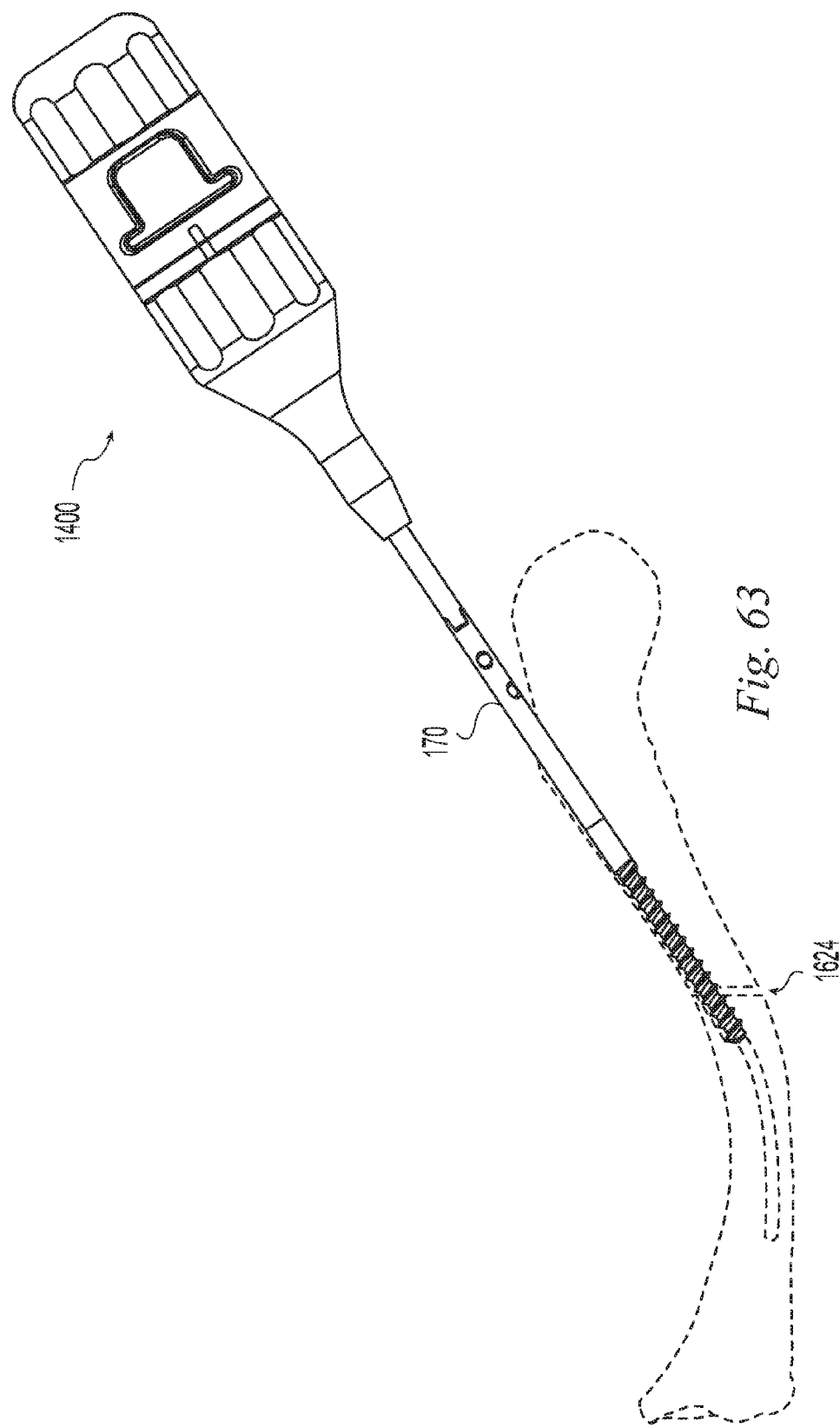

Referring to FIG. 63, the implant 170 corresponding to the last tap size used has been coupled to the inserter 1400 and advanced over the guide wire 1622, through the lateral bone tunnel 1612 and into the medial bone tunnel. In the illustrative example of FIG. 63, the fracture 1624 is shown slightly displaced as might happen during the procedure and to illustrate how the inserter 1400 may be used to reduce the fracture.

Figure 64:
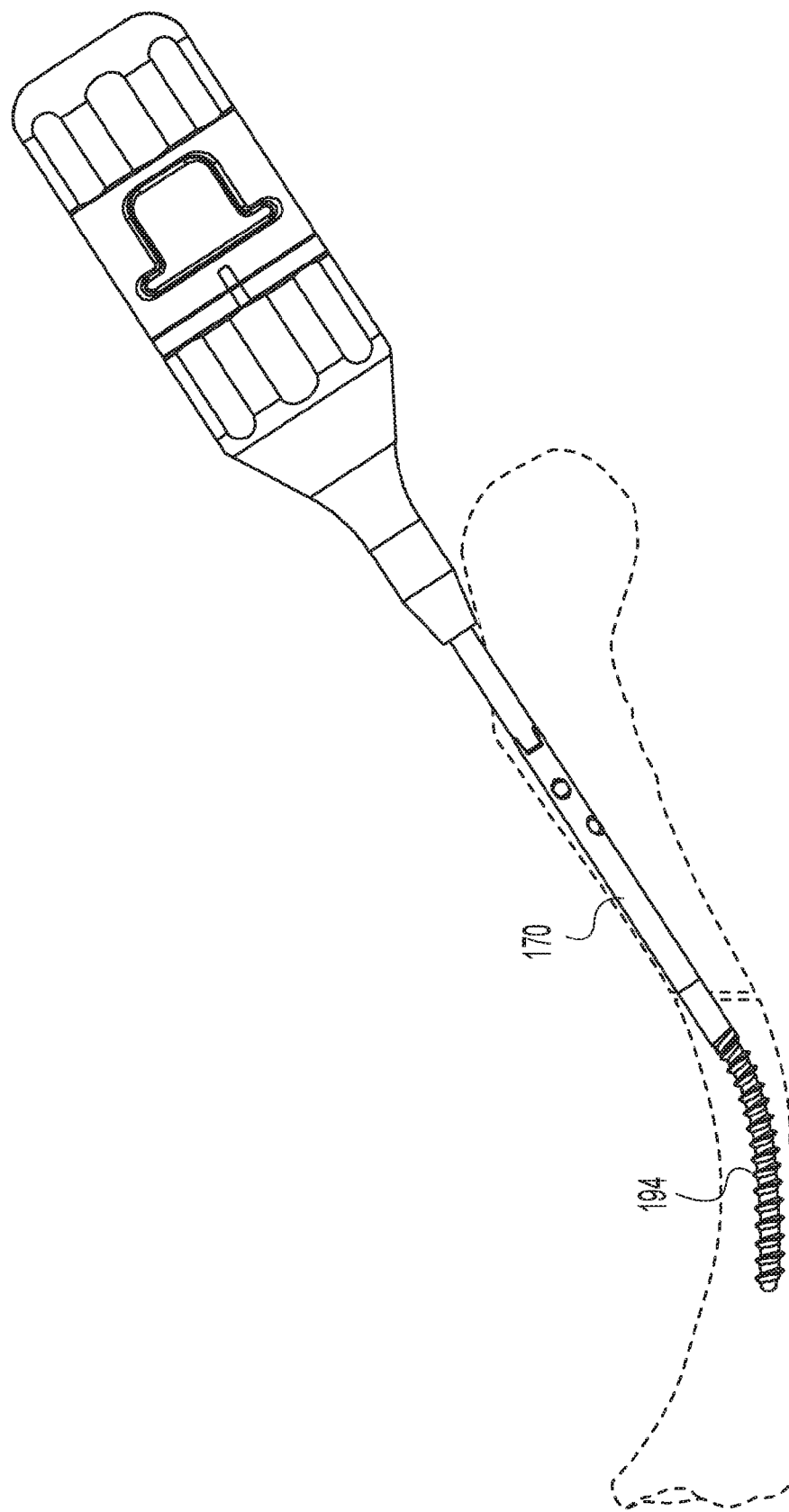

Referring to FIG. 64, the implant 170 has been advanced further so that the thread 194 of the flexible distal portion engages the thread in the medial fragment 1614. The screw is advanced until it is fully seated in the prepared thread in the medial bone fragment. Optionally, the implant 100 may be axially driven with a mallet through the lateral bone fragment until just short of the distal thread engagement. The screw may then be threaded into full engagement with the prepared thread in the medial fragment.

Figure 65:
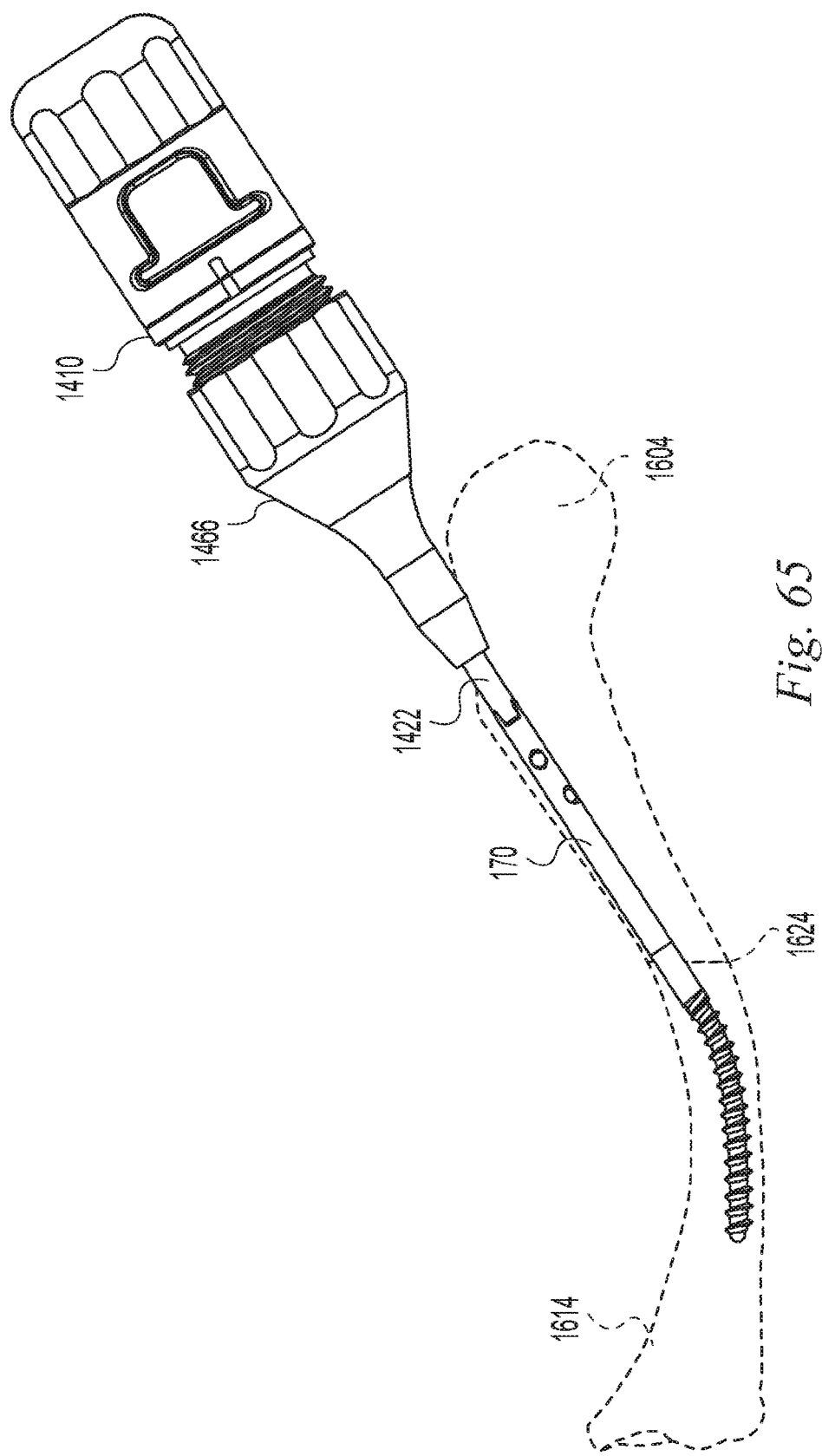

Referring to FIG. 65, the compression sleeve 1466 has been rotated relative to the hub 1410 so that the threaded engagement between them causes the compression sleeve 1466 to press against the lateral bone fragment 1604 and the hub 1410 to move away from the compression sleeve. The draw bar 1480 (FIG. 17) moves with the hub since the head 1482 of the draw bar abuts the proximal end of the post 1416. The interaction of the hub 1410 with the compression sleeve 1466 and the compression sleeve 1466 with the bone pulls the implant 170 laterally. Since the screw is anchored in the medial fragment 1614 and can slide in the lateral fragment 1604, this interaction applies compression to the fracture 1624.

Figure 66:
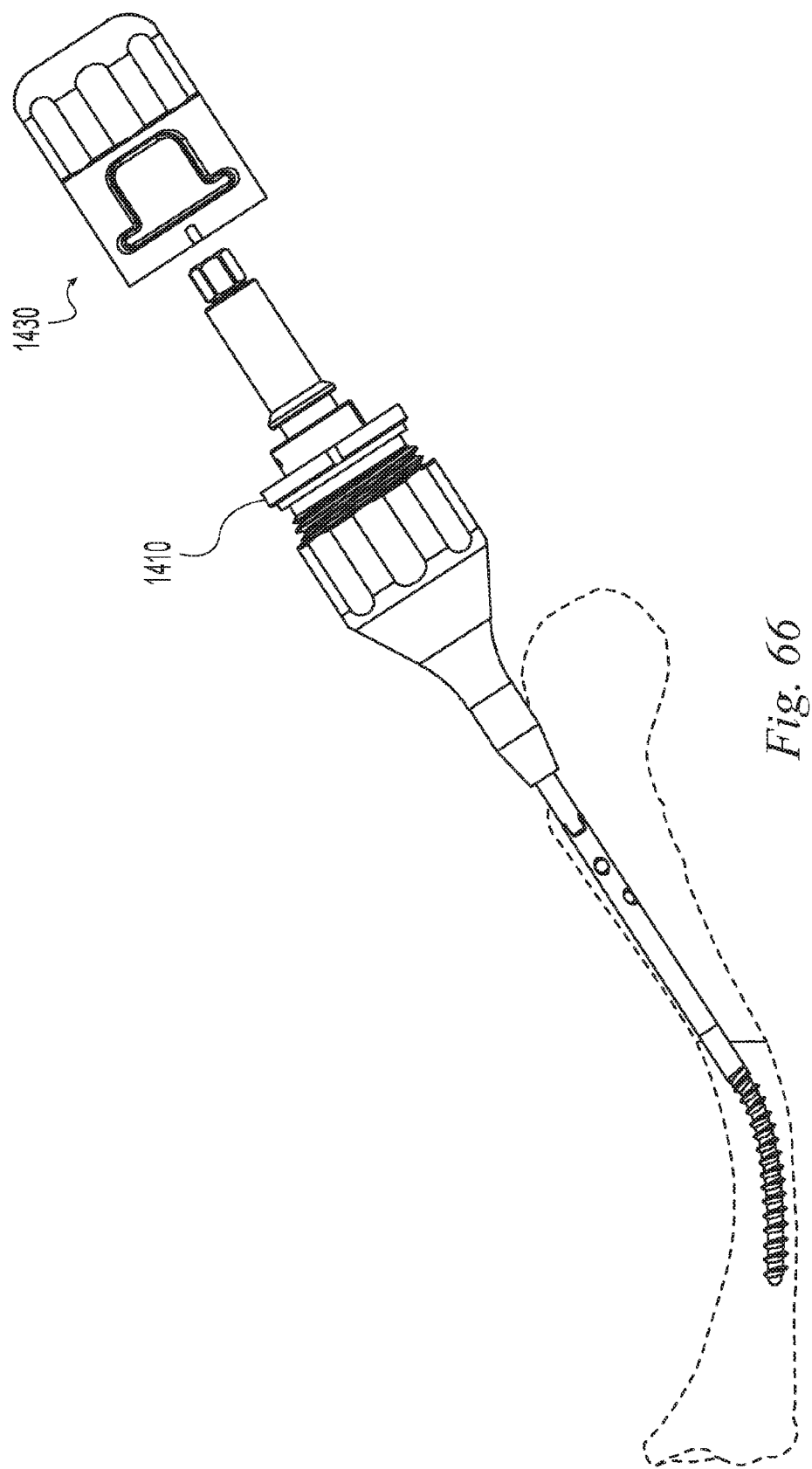

Referring to FIG. 66, the handle assembly 1430 is removed from the hub 1410 in preparation for attaching the cross pinning guide assembly 1458.

Figure 67:
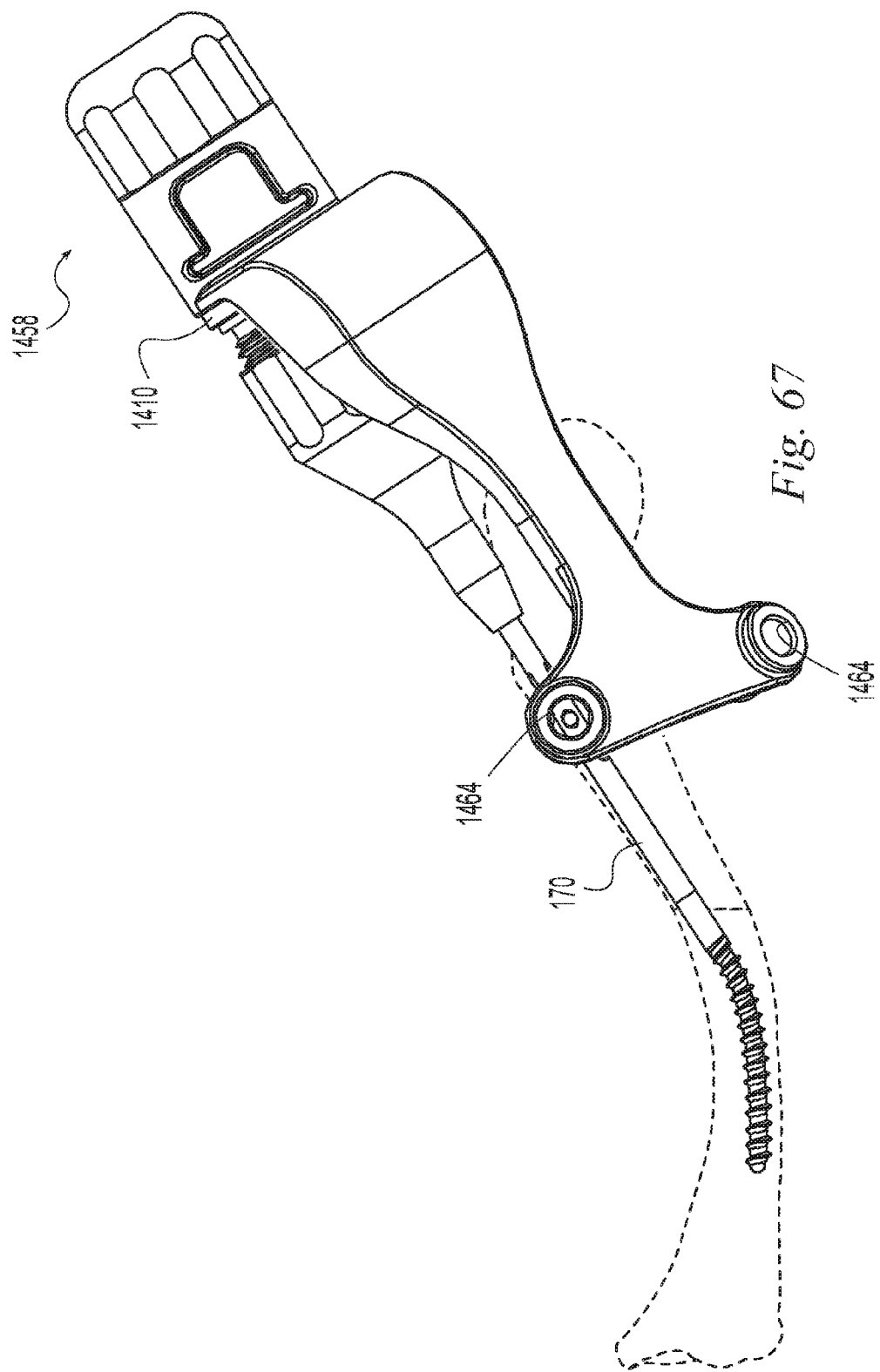

Referring to FIG. 67, the cross pinning guide assembly 1458 has been engaged with the hub 1410. With the cross pinning guide assembly 1458 locked onto the hub, guide holes 1464 are aligned with the passages 181, 183 in the proximal end of the implant 170.

Figure 68:
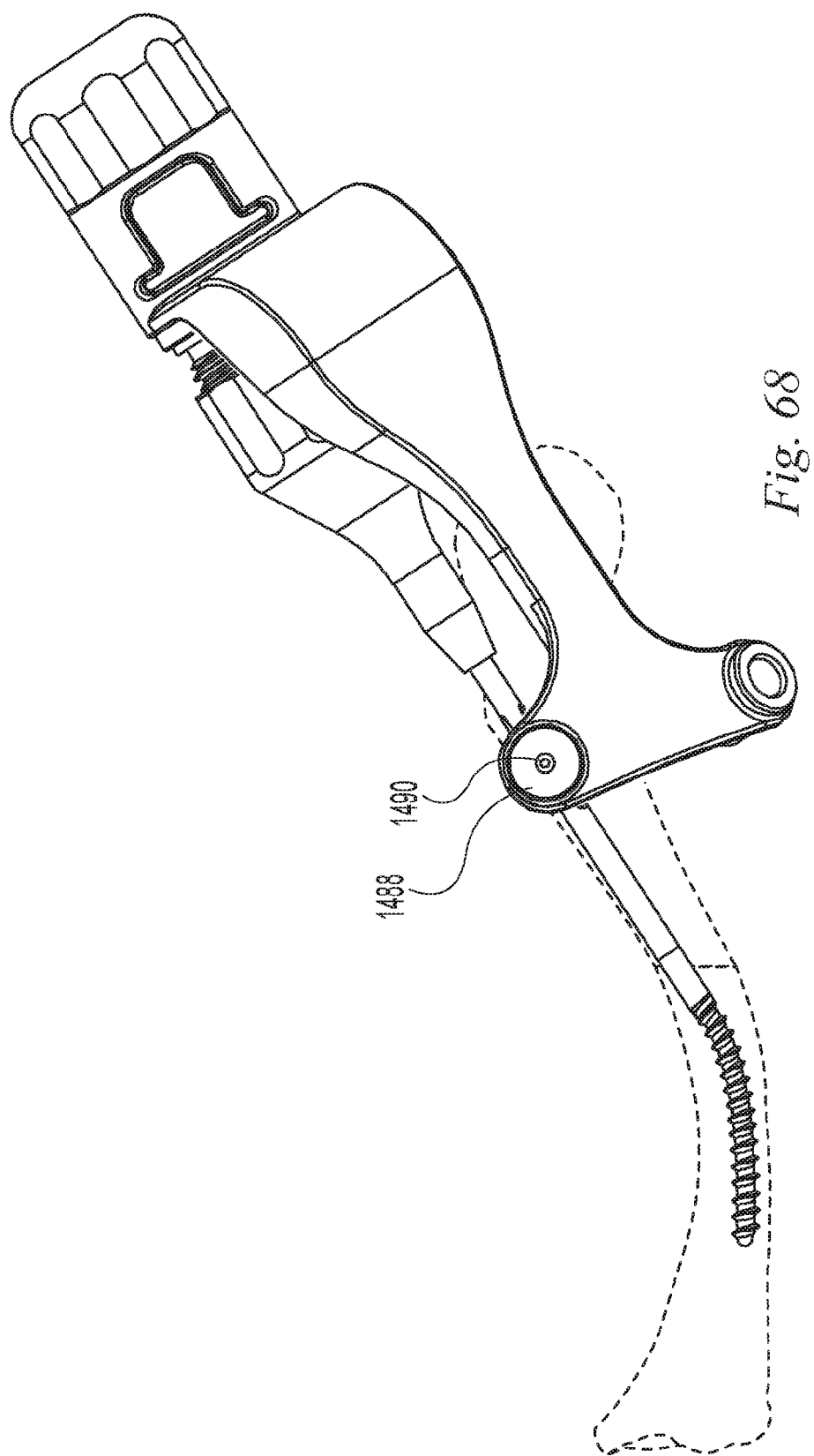

Referring to FIG. 68, the inner sleeve 1488 and outer sleeve 1489 are sequentially nested in the guide holes 1464 (shown positioned in one guide hole 1464 in FIG. 68) and used to guide a drill wire 1490 into the bone and through each of the passages 181, 183. Through tactile feedback the user can detect when the drill wire 1490 is engaged with the far cortical wall of the bone fragment. For example, the drill wire 1490 may be guided through the guide sleeves, through the near cortex, through a passage in the screw, and into the far cortex of the lateral bone fragment. If wire cross fixation is adequate, the cross fixation guide may be removed and the wire may be trimmed flush with the bone surface.

However, if screw cross fixation is desired, additional steps may be performed. For example, if desired, an optional counter sink tool (not shown) may be placed over the drill wire 1490 and used to counter sink the bone surface to receive a screw head. The inner sleeve 1488 may be removed and the depth gauge 1492 may be inserted over the drill wire and through the outer sleeve 1489 until it contacts the bone. The appropriate screw length is then read by comparing the proximal end of the drill wire 1490 to the scale 1493 on the depth gauge 1492.

Figure 69:
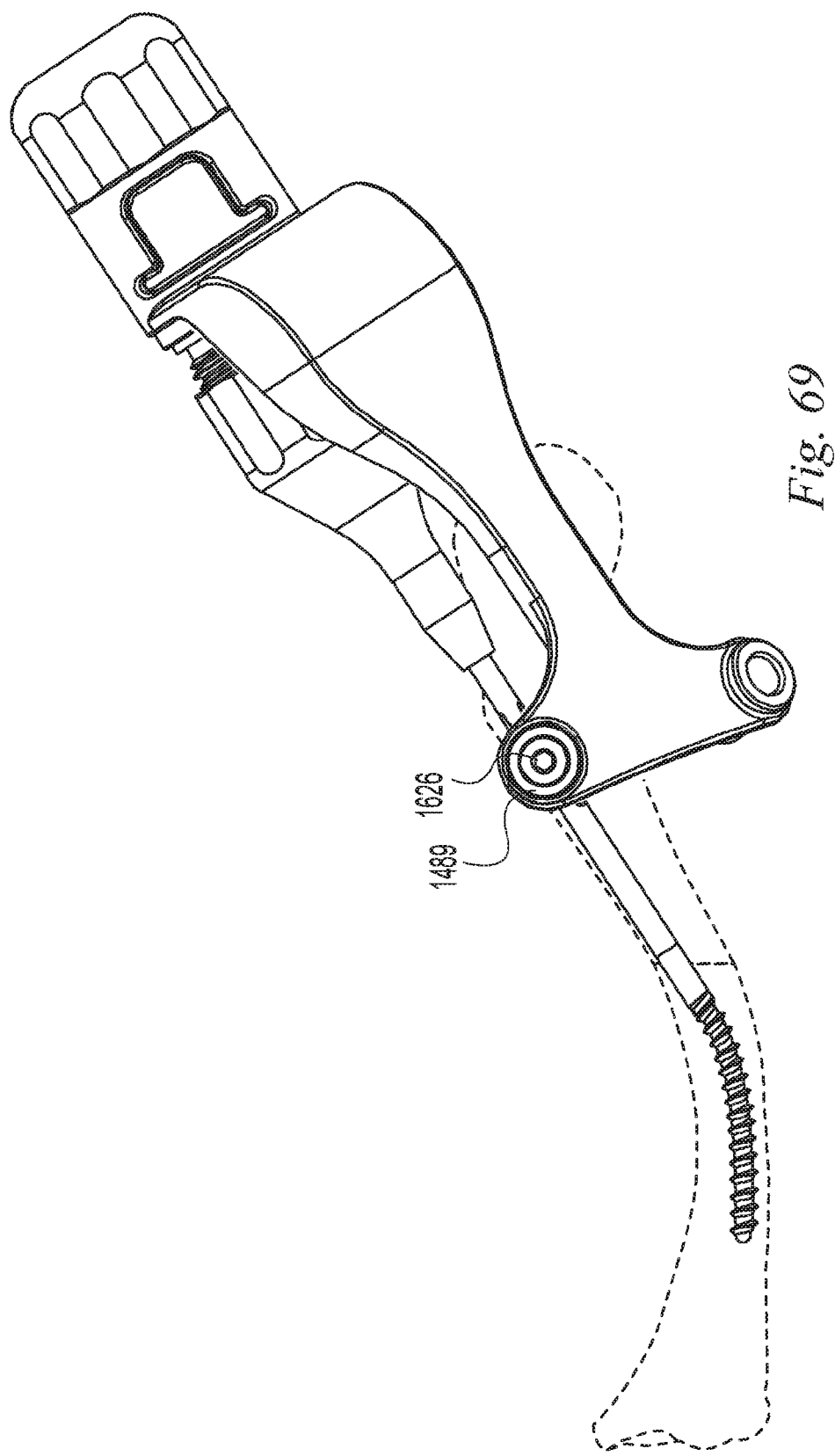

Referring to FIG. 69, a self-tapping cross-fixation screw 1626 has been inserted through the outer sleeve 1489 and turned into the bone so that it extends through the flexible implant 170. Following these same steps, as many additional cross fixation screws 1626 may be inserted through the flexible implant 170 as there are passages in the implant 170.

Figure 70:
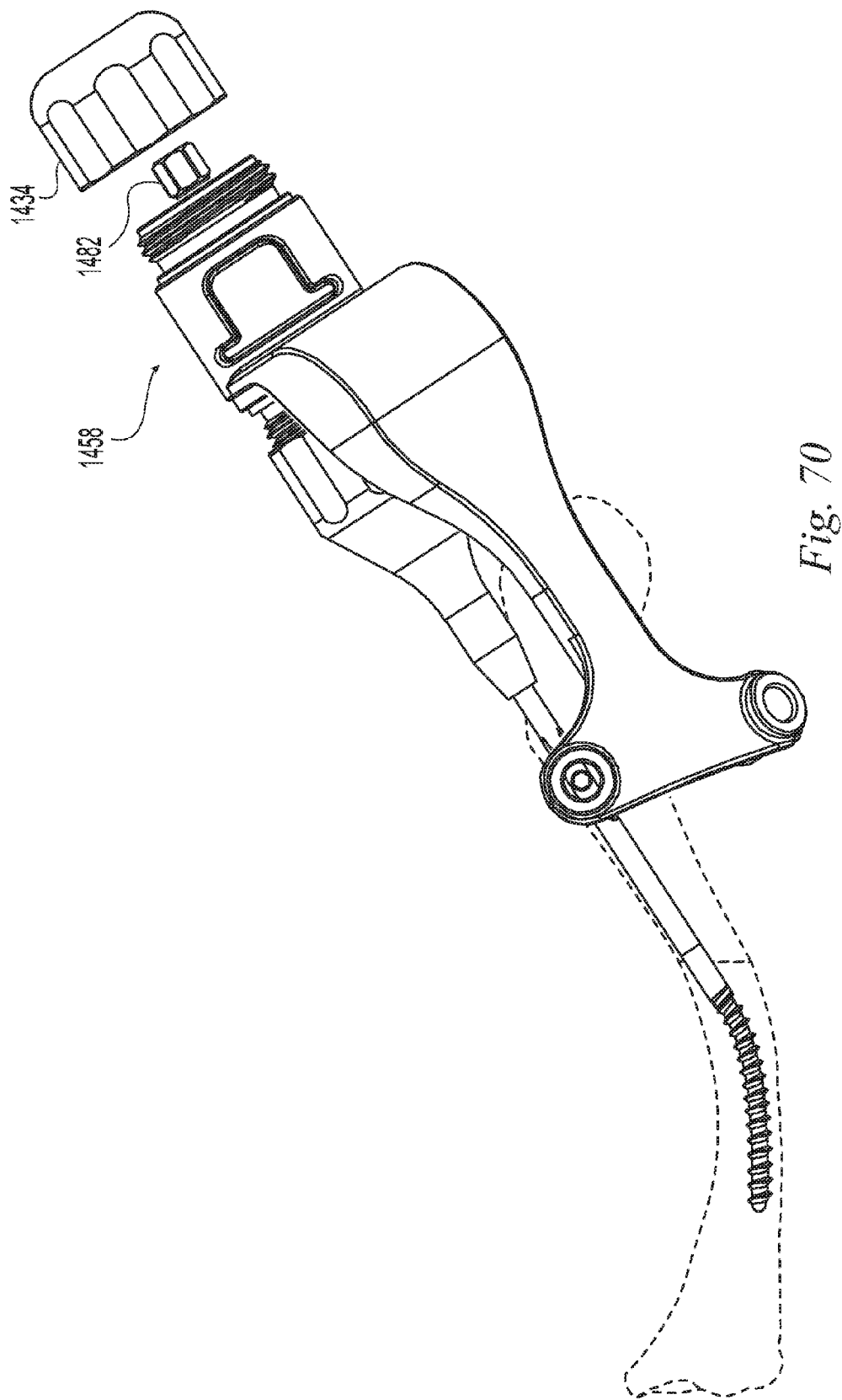

Referring to FIG. 70, the cap 1434 has been removed from the cross pinning guide assembly 1458 to expose the head 1482 of the draw bar. Alternatively, the entire cross pinning guide assembly 1458 may be removed to expose the head 1482.

Figure 71:
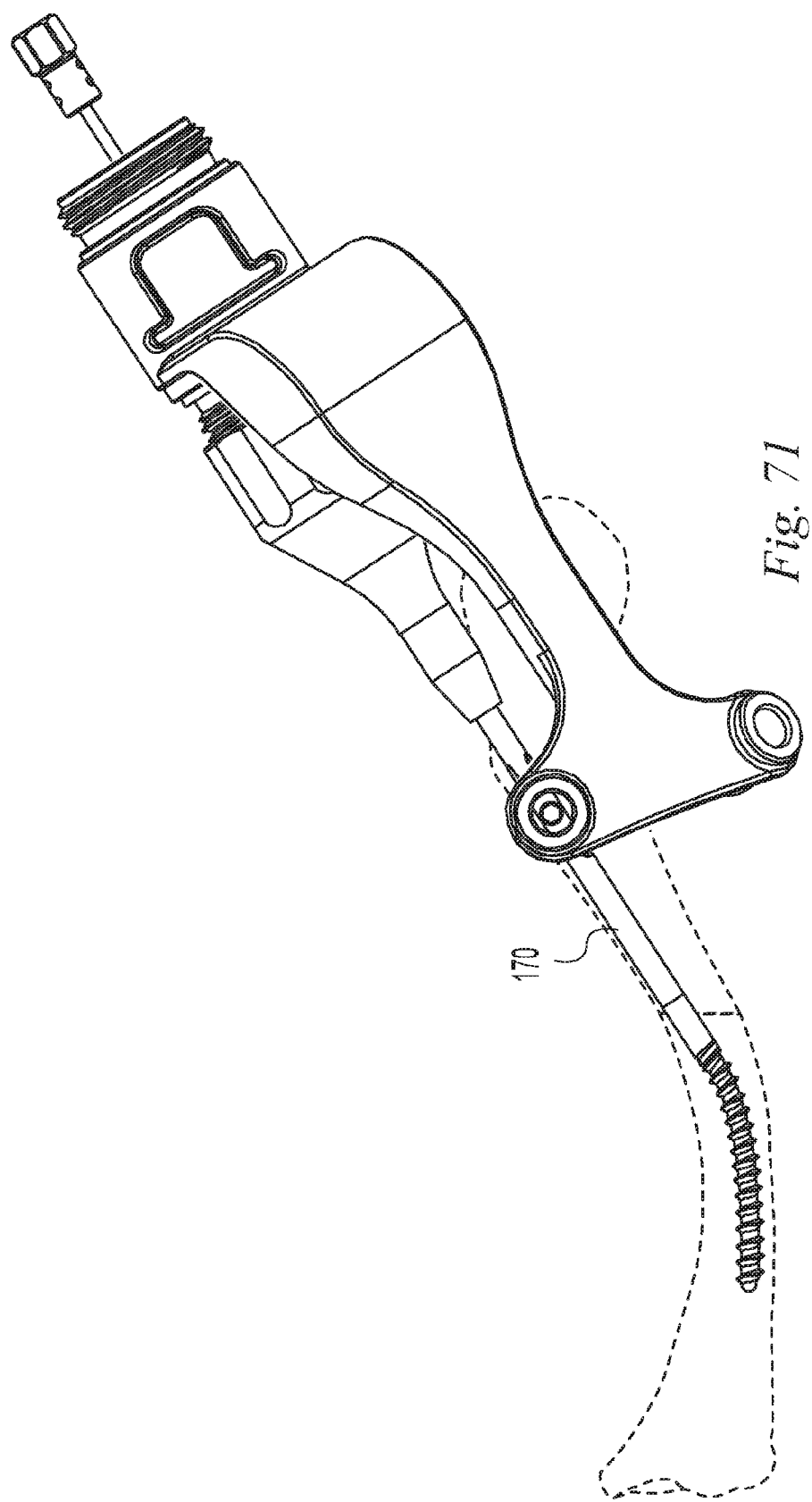

Referring to FIG. 71, the draw bar 1480 is rotated to unscrew it from the implant 170 and detach the inserter assembly 1400 from the implant 170.

Figure 72:
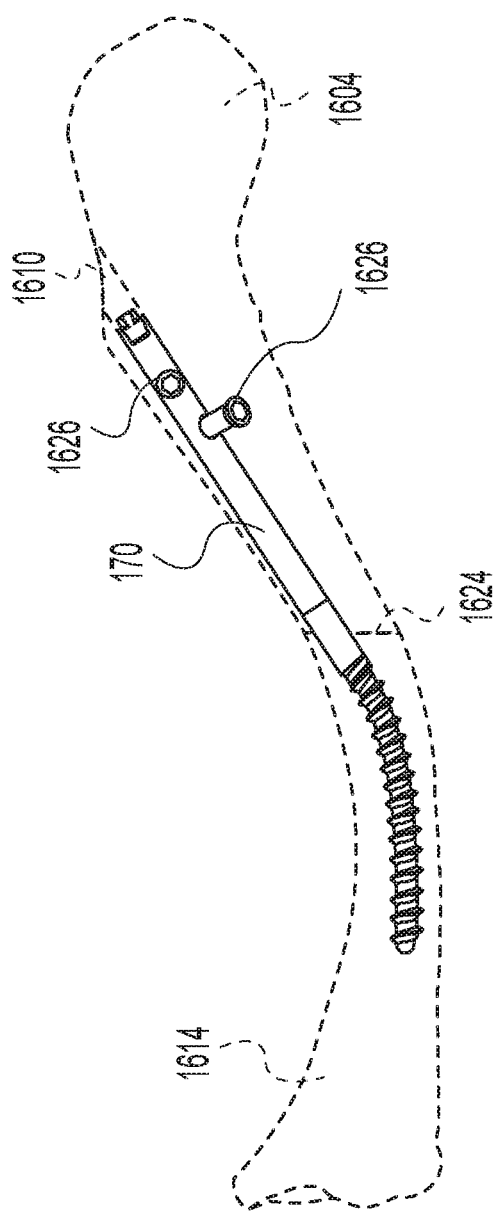

Referring to FIG. 72, the final fixation construct is shown with the fracture 1624 compressed, the implant 170 engaged with the medial bone fragment 1614, and cross fixation screws 1626 locking the implant 170 in the lateral fragment 1604.

FIGS. 73-81 depict an illustrative method of using the implant 600 of FIG. 22 and the inserter assembly 1300 of FIG. 35 to fixate a fractured fibula.

Figure 73:
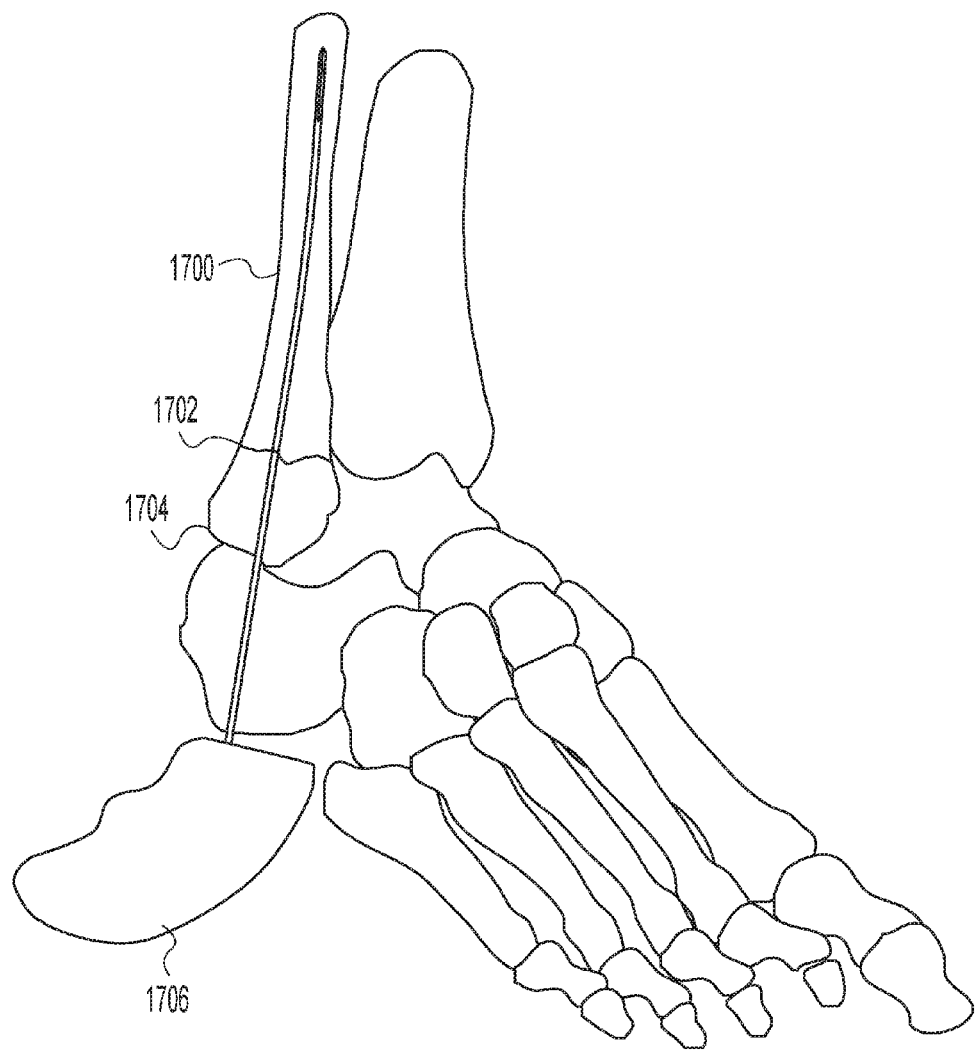
FIGS. 73-81 are perspective view illustrating a method fixating a fractured fibula according to one example of the invention.

Referring to FIG. 73, a fibula 1700 having a fracture 1702 is fixated by first reducing the fracture such as for example with bone forceps. An incision is made across the end of the lateral malleolus 1704 centered with the long axis of the fibular shaft. A pin or drill may be used to pierce the fibular cortex and establish the implant insertion trajectory. For example, a K-wire may be inserted through the fibular cortex between the anterior talofibular ligament (ATFL) and the calcaneofibular ligament (CFL). A flexible awl 1706, for example a Rush awl reamer, may be inserted through the hole formed in the cortex to create a path along the curved intramedullary canal of the fibula.

Figure 74:
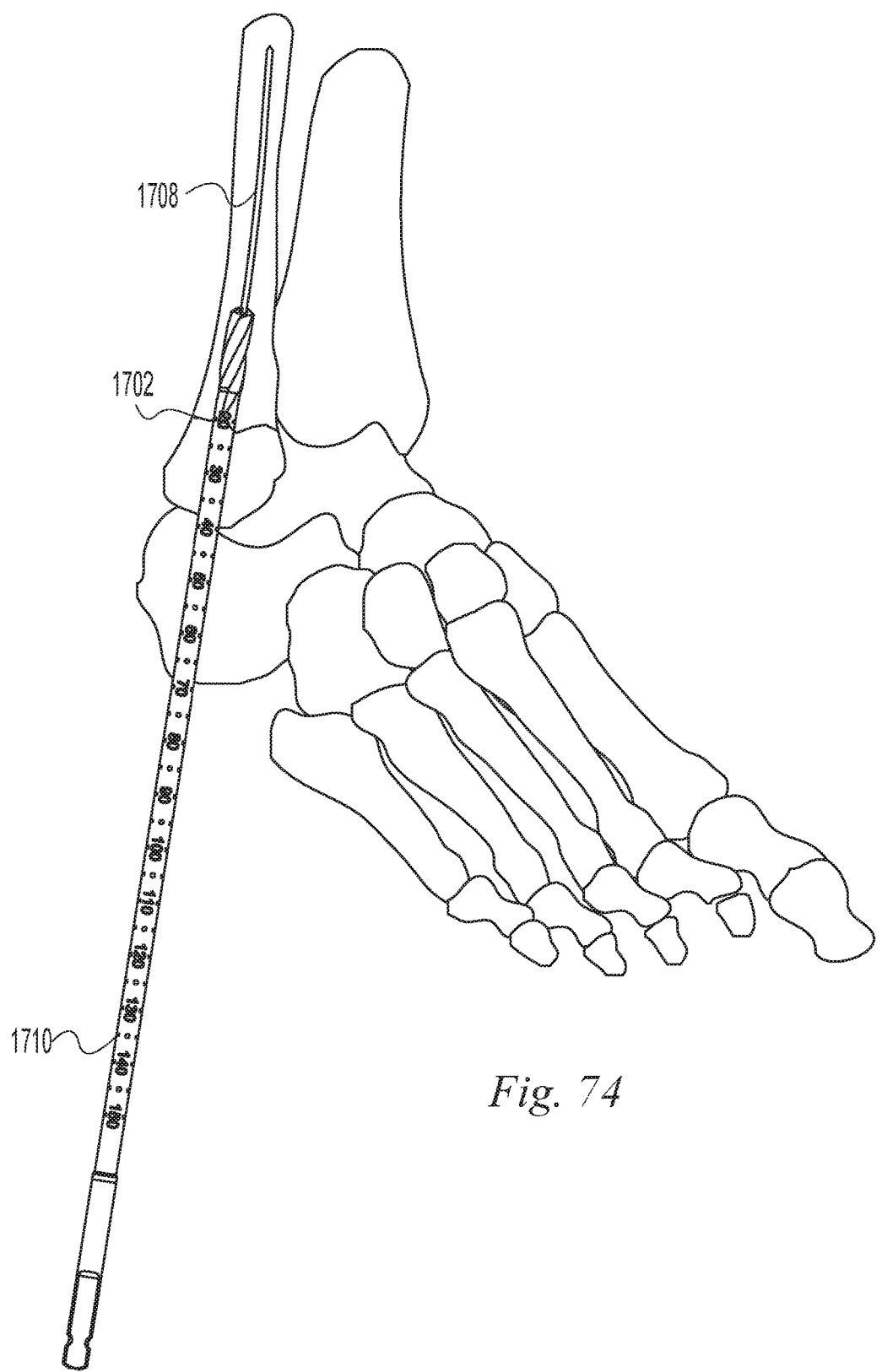

Referring to FIG. 74, the awl 1706 has been removed and a K-wire 1708 inserted along the implant insertion path. A rigid reamer 1710 is driven over the K-wire to create the entry portal to a desired depth. For example, if the implant is provided in a choice of discrete body lengths, the reamer is driven to a depth corresponding to one of those lengths. Preferably, the depth is chosen such that the implant proximal portion will span the fracture 1702.

Figure 75:
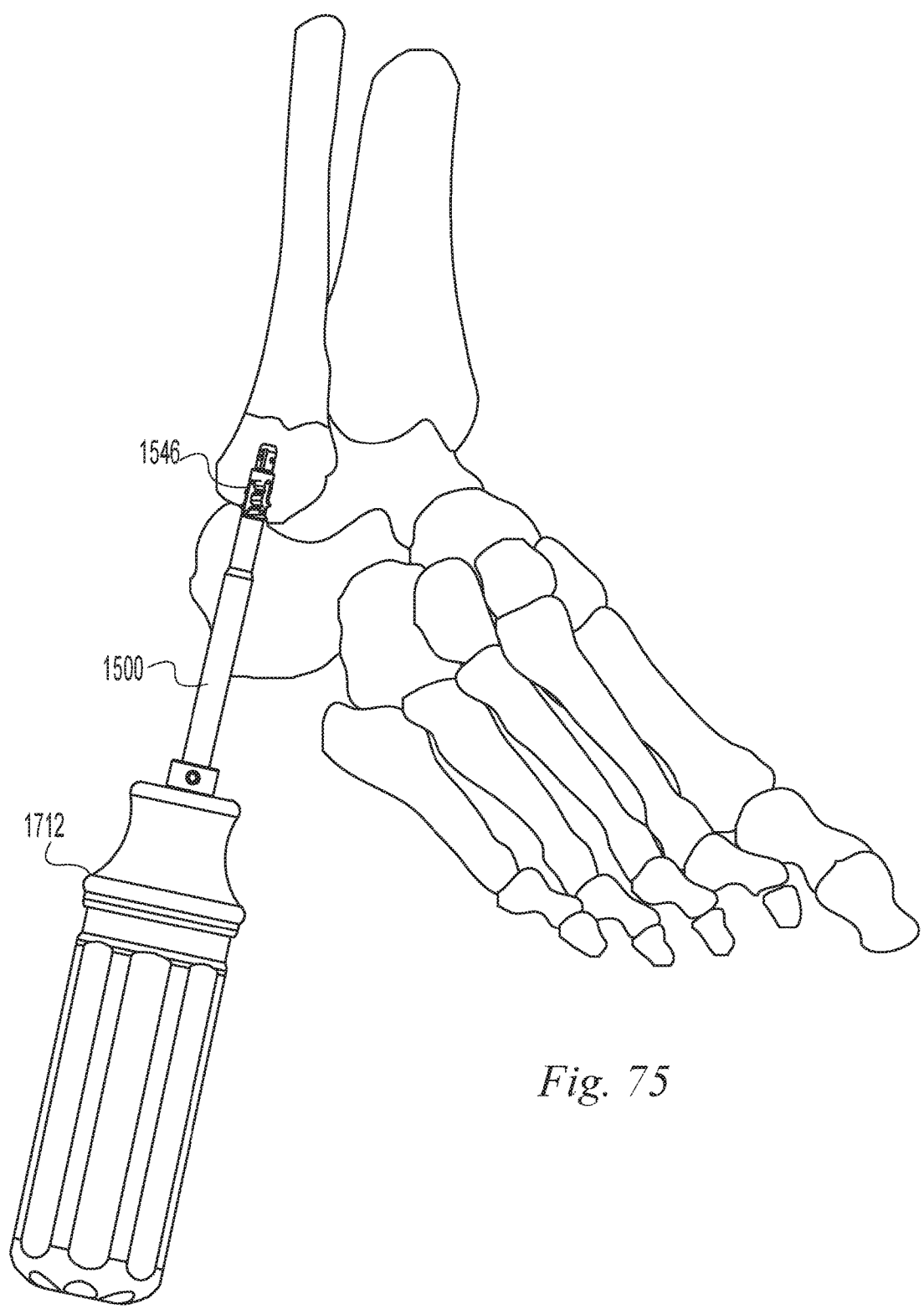
Figure 76:
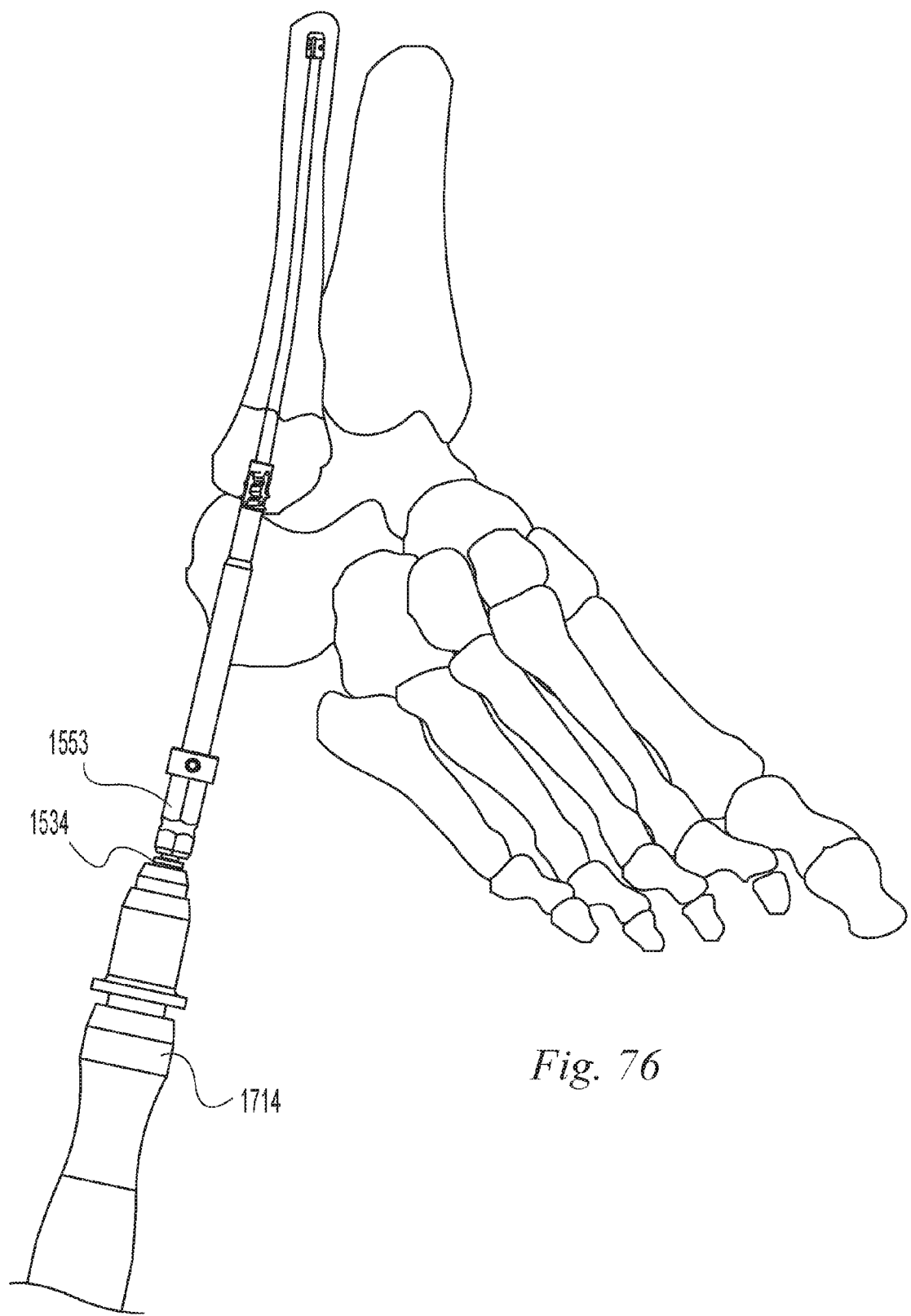

The implant path is then tapped. In first tapping example, shown in FIGS. 75 and 76, the tap 1500 is used. Referring to FIG. 75, the tap 1500, with the alternative driver engagement 1553 of FIG. 44, is engaged with a first handle 1712. The tap is anchored in the lateral malleolus by turning the self-tapping thread 1546 into the hole formed with the rigid reamer 1710. The first handle 1712 covers the end 1534 of the driving shaft 153 of the tap so that the tap head 1506 is not advanced inadvertently. Referring to FIG. 76, the first handle 1712 is removed and a second handle 1714 is engaged with the end 1534 of the driving shaft 1530 and rotated to tap the implant path. A wrench, such as wrench 1497 of FIG. 42 may be engaged with the driver engagement 1553 to apply counter torque if desired.

Figure 77:
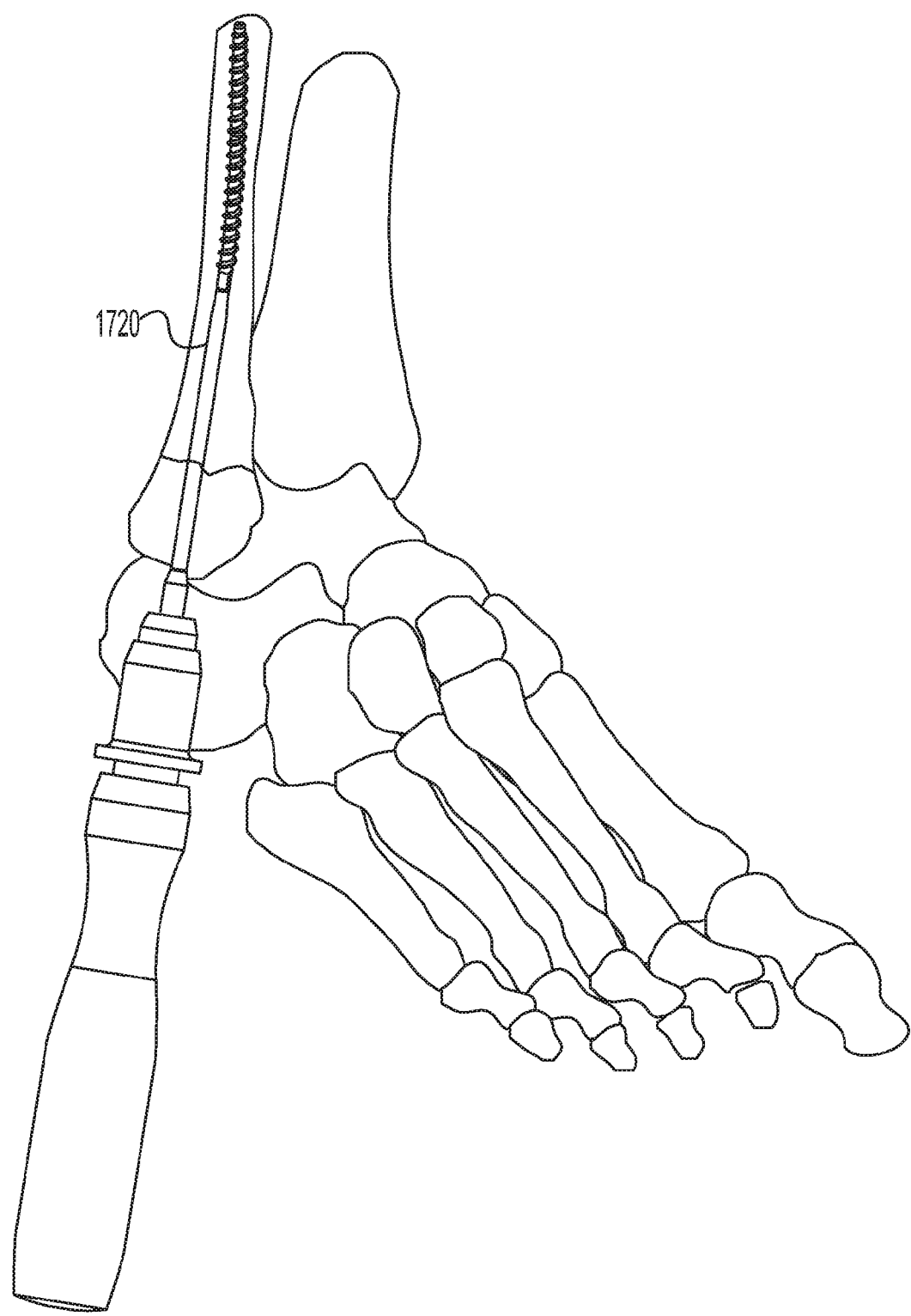

Alternatively, in a second tapping example show in FIG. 77, a one-piece tap 1720 may be used since the fibular intramedullary canal has a relatively subtle curvature The tap 1720 in the example of FIG. 77, has a cutting thread form corresponding to the thread form of the implant 600 of FIG. 22. The minor diameter and pitch of the tap 1720, like the implant 600, are such that the tap can flex to follow the fibular curvature.

Figure 78:
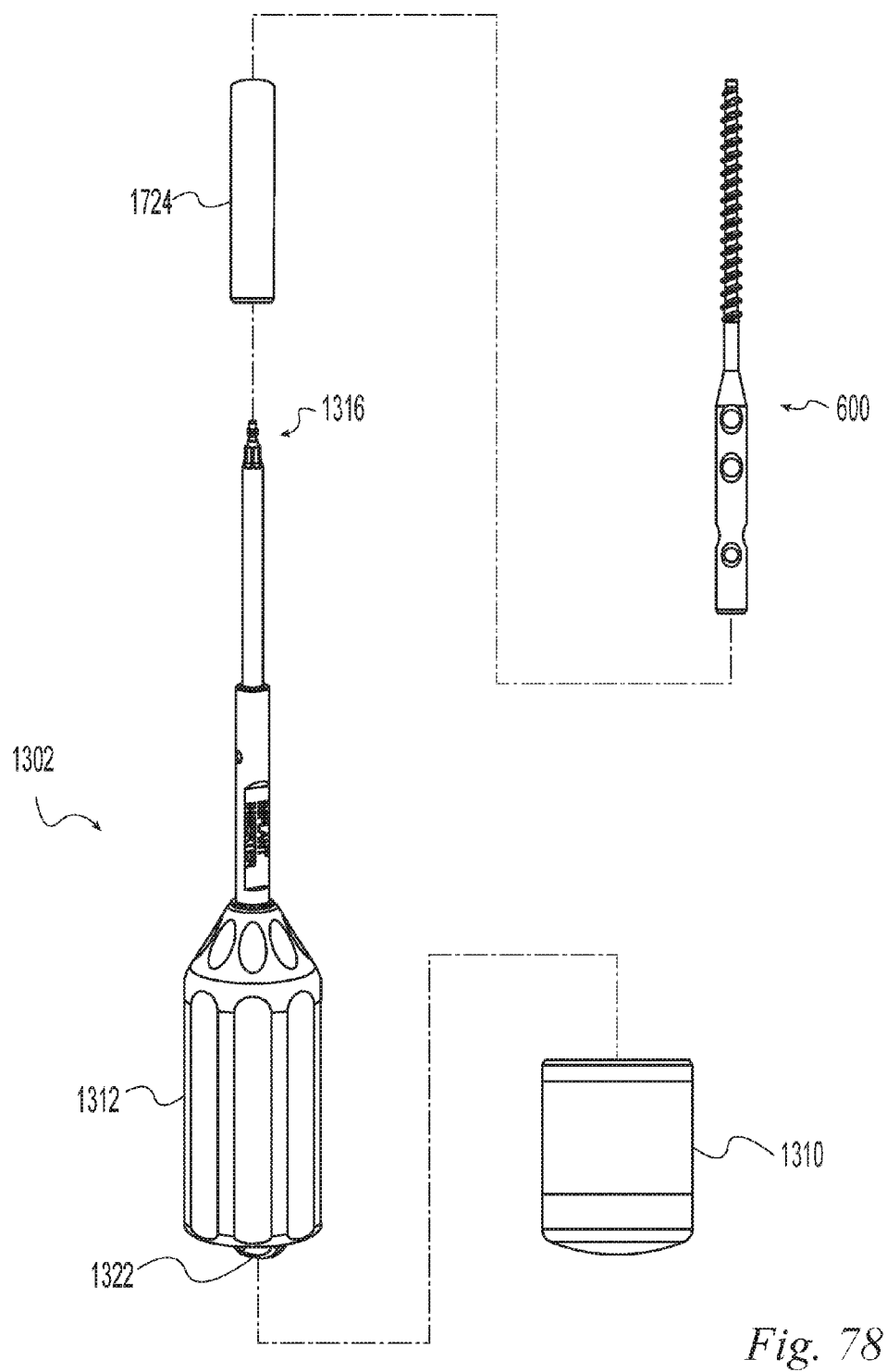

Referring to FIG. 78, the inserter 1302 is joined to the implant 600 by inserting the implant engagement end 1316 into the drive socket of the implant 600 and turning the knob 1322 to thread the drawbar into the threaded hole in the end of the drive socket to draw the implant into engagement with the inserter and secure it in place. Optionally, a compression sleeve 1724 may first be placed over the inserter shaft. In the example of FIG. 78, the compression sleeve has a flat distal end since it will be abutting the distal end of the fibula and no chamfer is necessary to provide sufficient bearing contact with the bone. Optionally, the cap 1310 may be placed over the handle 1312 of the inserter if it is desired to impact the implant 600 along the initial portion of its insertion path.

Figure 79:
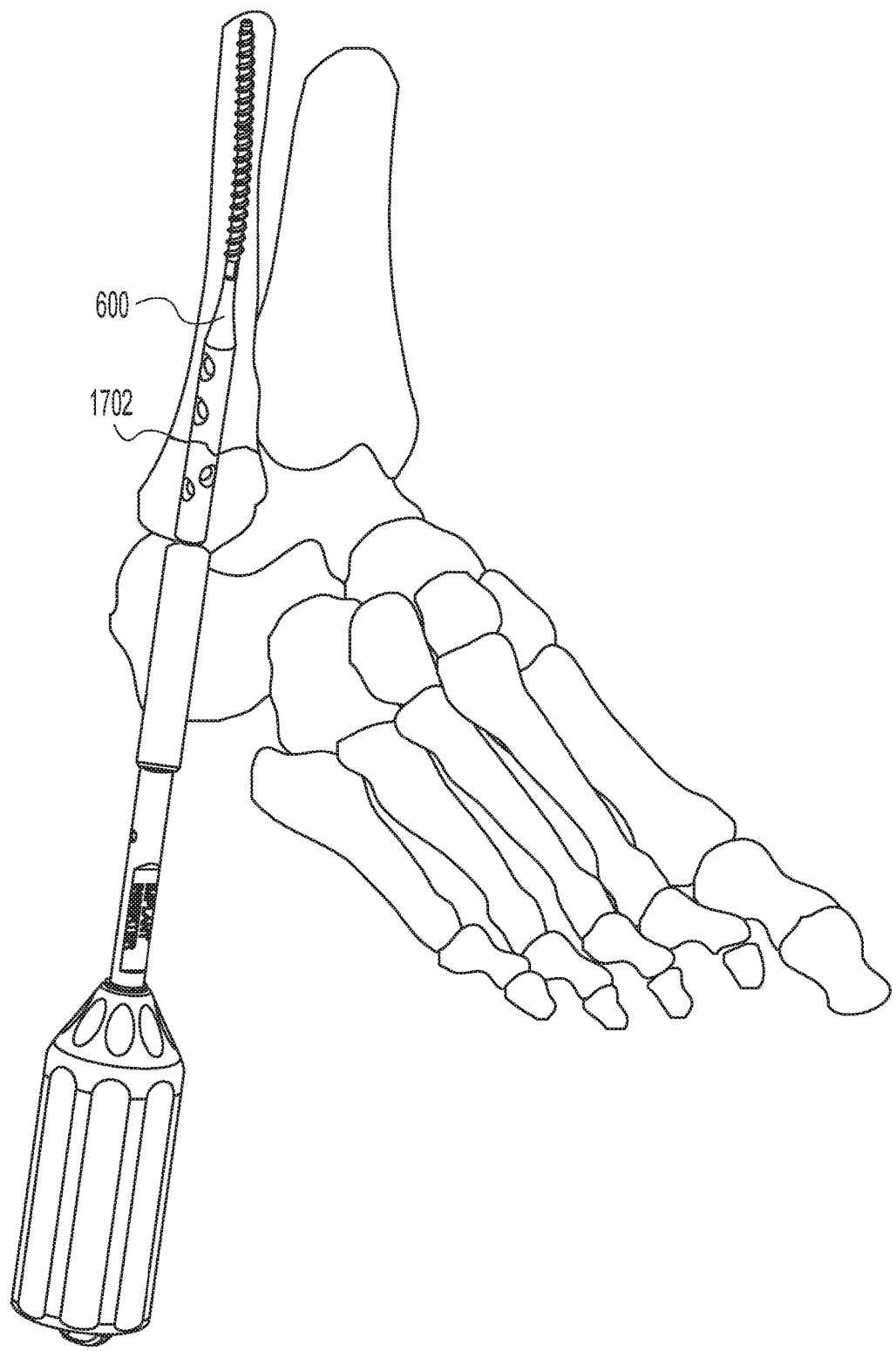

Referring to FIG. 79, the implant 600 has been threaded into the fibula 1700 until the compression sleeve contacts the lateral malleolus at the distal end of the fibula. With the compression sleeve 1724 bearing on the bone, further rotation of the implant causes the bone fragments to be pressed together to reduce the fracture 1702. Preferably, the implant is advanced until it is 2-5 mm below the surface of the lateral malleolus.

Figure 80:
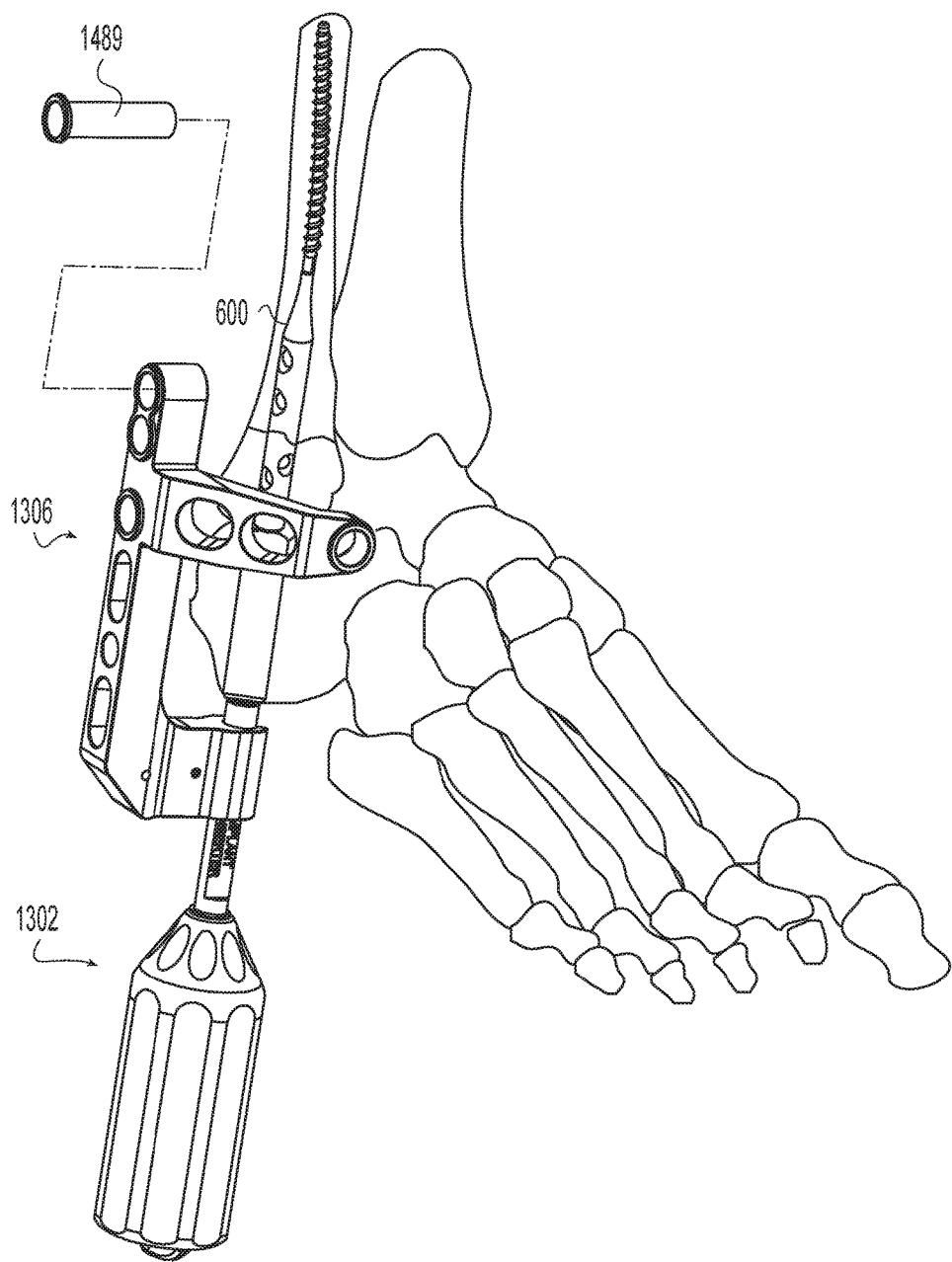

Referring to FIG. 80, the cross pinning guide 1306 corresponding to the implant 600 is mounted to the inserter 1302 and the inserter 1302, cross pinning guide 1306 and implant 600 are rotated to align the guide holes 1330, 1332, 1334 with the desired screw trajectories. Small stab incisions are created at each screw entry point to allow the drill sleeve 1488 to seat against the bone surface. A screw is installed in the bone and intersecting each transverse hole in the implant 600 by inserting the drill sleeve 1488 in each guide hole, guiding a drill through the bone and transverse hole, using the depth gage to measure proper screw length, countersinking the bone surface, and screwing the screw into the bone with the screw traversing the transverse hole. This is repeated for each desired screw.

Figure 81:
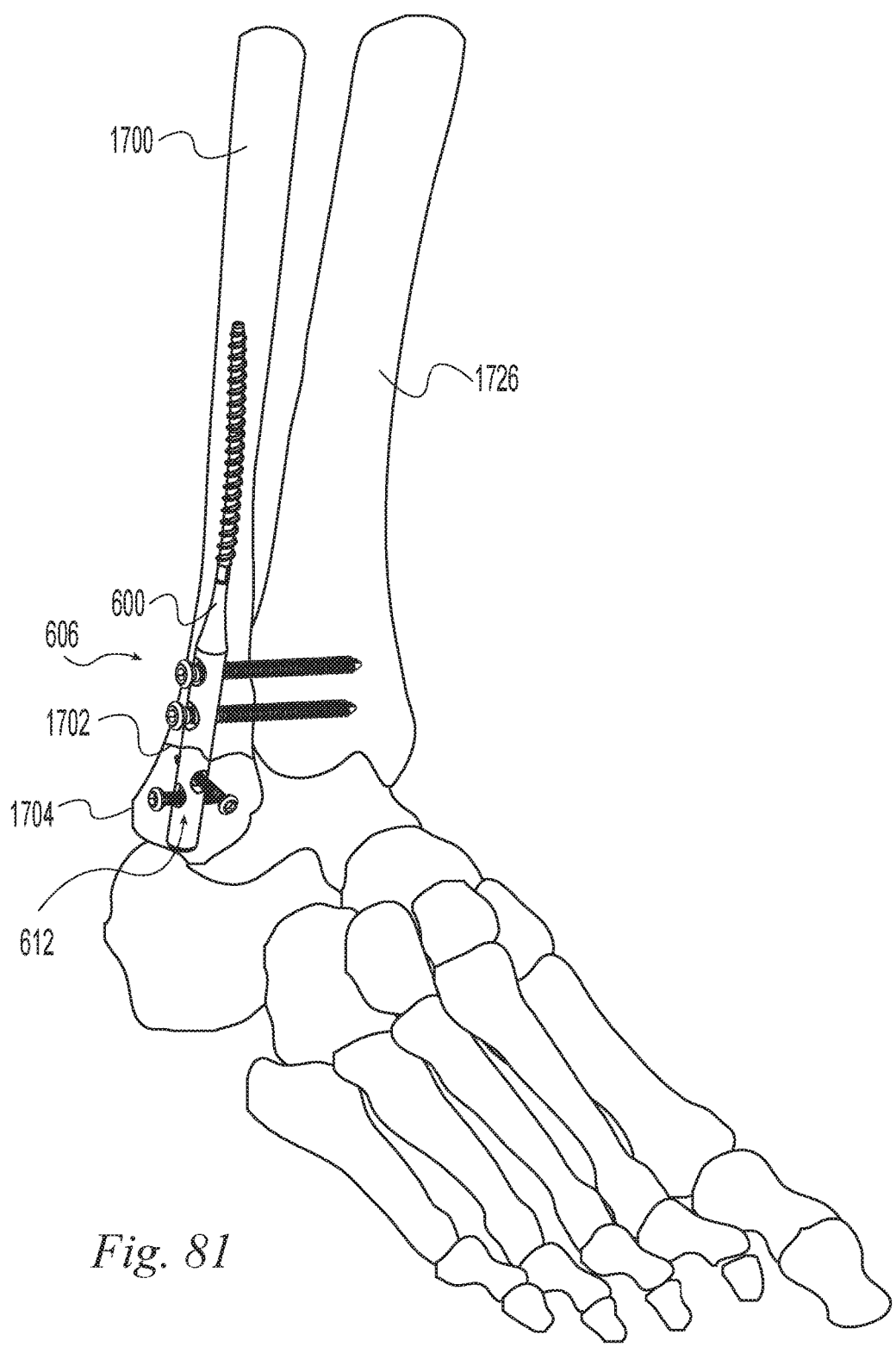

Referring to FIG. 81, screws placed through the first pair of transverse holes 606 may be used to attach bone fragments such as the lateral malleolus 1704 to the fibular shaft 1700. Screws placed through the second pair of transverse holes 612 may be extended through the fibula and into the tibia 1726 to reinforce the syndesmosis joint. The implants, instruments, and methods according to examples of the invention may be used to fixate bones, bone fragments and joint throughout the body.

Figure 82:
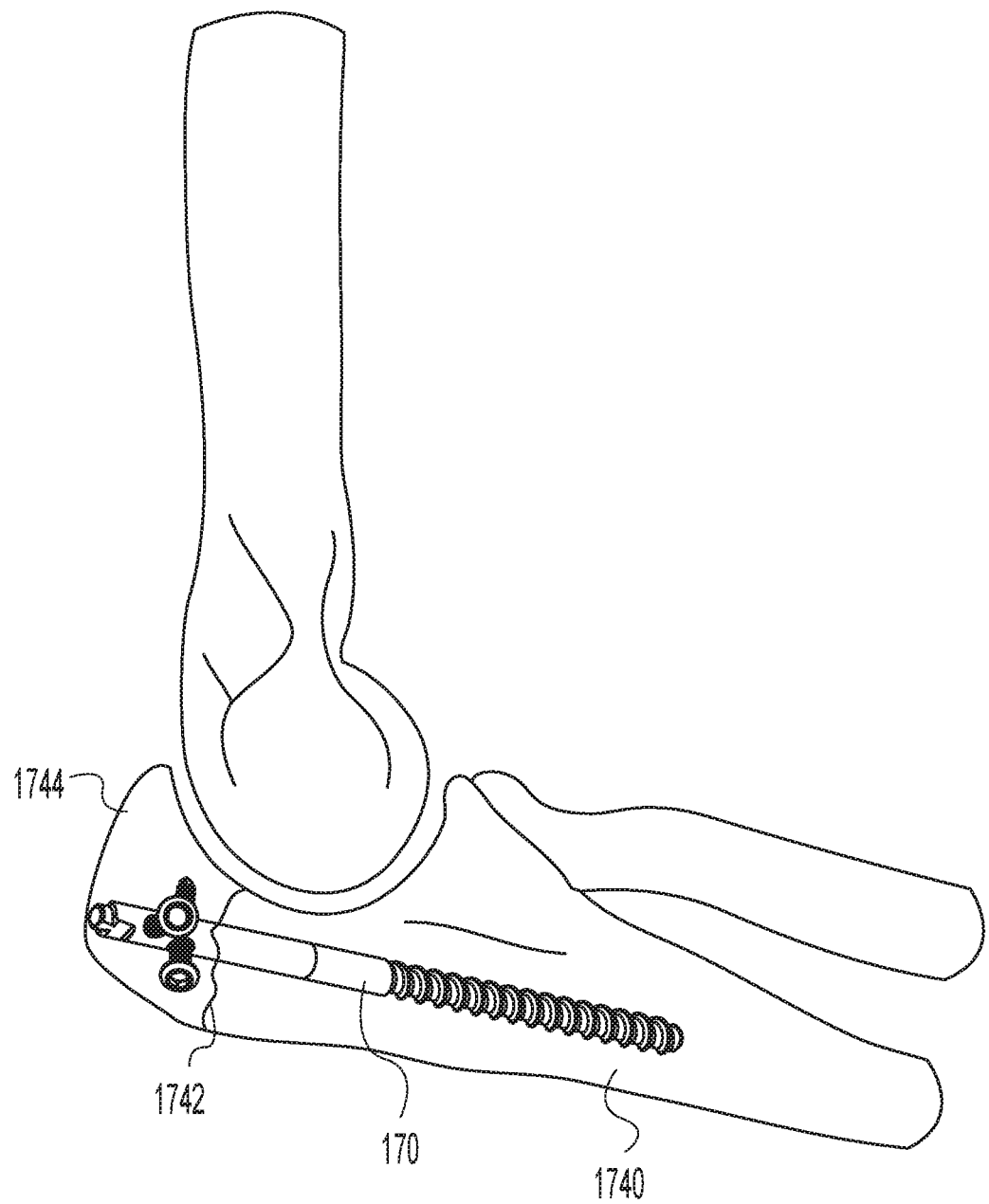
FIG. 82 is a plan view illustrating a method of fixating a fractured radius according to one example of the invention.

Referring to FIG. 82, the implant 170 of FIG. 8 is used to repair an olecranon fracture of an ulna 1740 having a fracture 1742 and a fragment 1744. The implant 170 is inserted through the fragment 1744 into the intramedullary canal of the ulna 1740. As the implant is rotated, the distal threaded portion engages the bone and pulls the proximal portion into the bone to a position bridging the fracture 722. The distal threaded portion bends to follow the curved path of the intramedullary canal. Bone screws are placed into the fragment and the holes of the implant 170 to secure the fragment.

Figure 83:
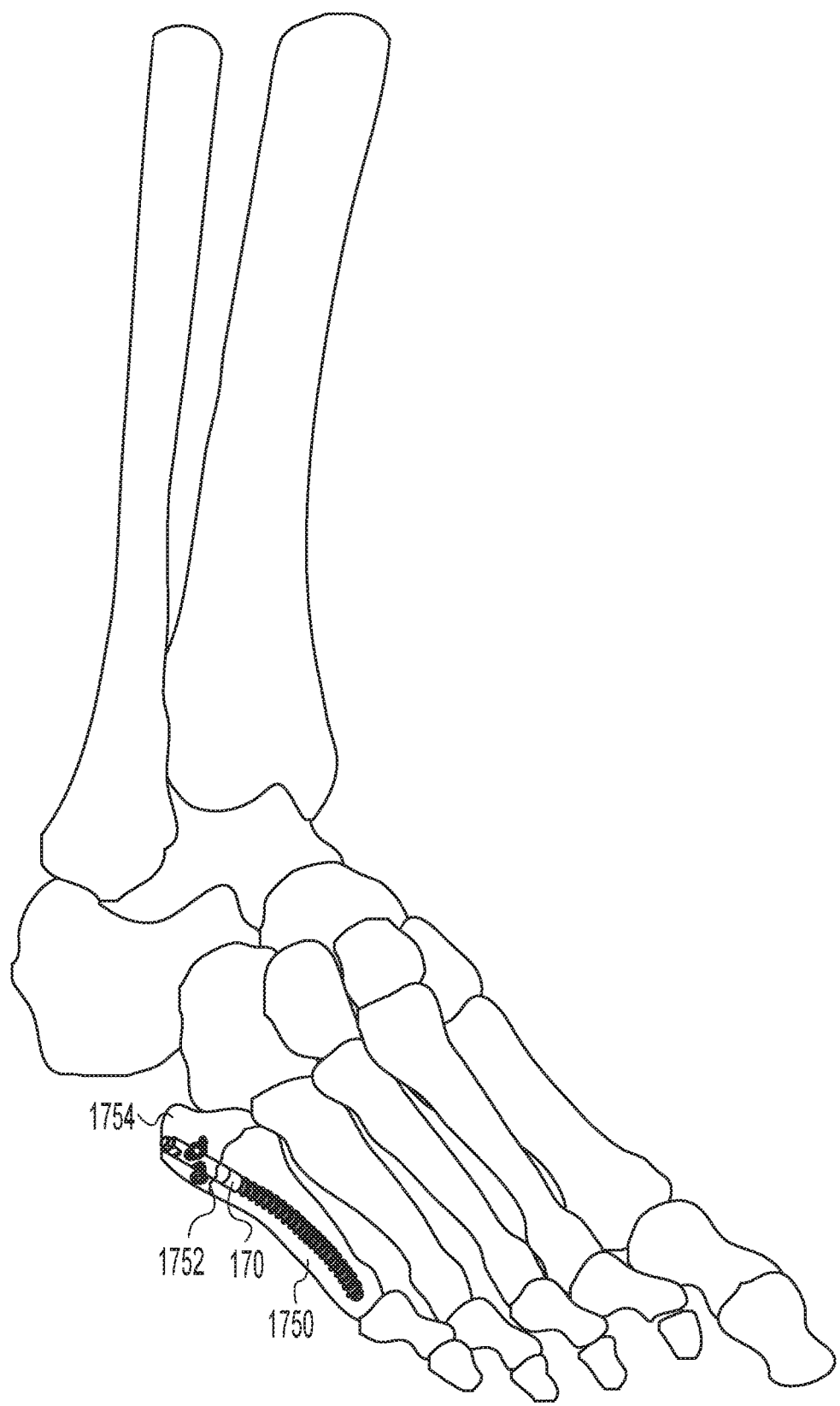
FIG. 83 is a perspective view illustrating a method fixating a fractured fifth metatarsal according to one example of the invention.

Referring to FIG. 83, the implant 170 of FIG. 8 is used to repair a Jones fracture of a fifth metatarsal 1750 having a fracture 1752 and a fragment 1754. The implant 170 is inserted through the fragment 1754 into the intramedullary canal of the fifth metatarsal. As the implant is rotated, the distal threaded portion engages the bone and pulls the proximal portion into the bone to a position bridging the fracture 1752. The distal threaded portion bends to follow the curved path of the intramedullary canal. Bone screws are placed into the fragment and the holes of the implant 170 to secure the fragment.

Various illustrative examples have been described. The various examples may be substituted and combined and other alterations made within the scope of the invention.

What is claimed is:

1. A method of fixating a first bone portion relative to a second bone portion, the method comprising:
    advancing a rigid drill to form a first bone hole from an outer surface of the first bone portion to a fracture site interposed between the first and second bone portions;
    advancing the rigid drill across the fracture site to form a second bone hole into the second bone portion;
    engaging a flexible drill with the second bone hole; and
    advancing the flexible drill to extend the second bone hole along a curved path.

2. The method of claim 1 further comprising:
    advancing a flexible tap in the second bone hole to form a helical thread along the curved path.

3. The method of claim 1 further comprising:
    driving a flexible threaded implant through the first bone hole, across the fracture site and into the second bone hole so that the threaded portion extends along the curved path.

4. The method of claim 3 further comprising:
    using a driver coupled to the flexible threaded implant to compress the first and second bone portions together.

5. The method of claim 4 wherein compressing the first and second bone portions together comprises pulling on the flexible threaded implant while pressing on a bone surface adjacent the first bone hole.

6. The method of claim 4 wherein compressing the first and second bone portions together comprises coupling the flexible threaded implant to the driver in axial force and torque transmitting relationship, abutting a portion of the driver against the first bone, and rotating the flexible threaded implant.

7. The method of claim 5 further comprising:
    displacing a sleeve coupled to a portion of the driver so that the sleeve presses against the bone surface adjacent the first bone hole.

8. The method of claim 7 wherein the sleeve threadably engages the driver, the method further comprising:
    rotating the sleeve to threadably drive the sleeve in a first direction and pull the flexible threaded implant in a second opposite direction.

9. The method of claim 3 further comprising:
    placing a fixation element transversely through the flexible threaded implant and into at least one of the first and second bone portions.

10. The method of claim 9 wherein placing a fixation element comprises placing the fixation element through a passage formed in a non-threaded first portion of the flexible threaded implant, the first portion being positioned within the first bone hole.

11. The method of claim 9 wherein placing a fixation element comprises engaging a modular guide assembly with a driver while the driver remains engaged with the flexible threaded implant and guiding the fixation element with the guide assembly.

12. The method of claim 9 wherein placing a fixation element comprises:
    engaging a modular guide assembly with a driver while the driver remains engaged with the flexible threaded implant;
    guiding a hole forming instrument with the modular guide through a passage formed in a non-threaded first portion of the flexible threaded implant, the first portion being positioned within the first bone hole;
    inserting a screw through the passage while the modular guide assembly remains engaged with the driver and the driver remains engaged with the flexible threaded implant.

13. The method of claim 3 wherein the first and second bone portions are medial and lateral fragments of a fractured clavicle, the method comprising inserting the flexible threaded implant so that a distal threaded portion of the implant is engaged with the intramedullary canal of the medial fragment and an unthreaded portion of the implant spans the fracture.

14. The method of claim 3 wherein the first and second bone portions are a lateral malleolus and shaft of a fractured fibula, the method comprising inserting the flexible threaded implant so that a distal threaded portion of the implant is engaged with the intramedullary canal of the fibular shaft and an unthreaded portion of the implant spans the fracture.

15. The method of claim 14 further comprising:
    inserting a first fixation member into a transverse passage through a portion of the flexible threaded implant lying within the lateral malleolus, the fixation member extending into the lateral malleolulus on opposite sides of the flexible threaded implant.

16. The method of claim 15 further comprising:
    inserting a second fixation member into a transverse passage through a portion of the flexible threaded implant, the second fixation member extending into the fibula on a first side of the flexible threaded implant and the second fixation member extending into a tibia on a second side of the flexible threaded implant opposite the first side.

17. The method of claim 3 wherein the first and second bone portions are an olecranon and shaft of a fractured ulna, the method comprising inserting the flexible threaded implant so that a distal threaded portion of the implant is engaged with the intramedullary canal of the ulnar shaft and an unthreaded portion of the implant spans the fracture.

18. The method of claim 3 wherein the first and second bone portions are proximal and distal fragments of a fracture metatarsal bone, the method comprising inserting the flexible threaded implant so that a distal threaded portion of the implant is engaged with the intramedullary canal of the distal metatarsal shaft and an unthreaded portion of the implant spans the fracture.

* * * * *